United States Patent
Hur et al.

(10) Patent No.: US 12,163,940 B2
(45) Date of Patent: Dec. 10, 2024

(54) CBRNE SENSORS AND SYSTEM FOR MONITORING AND DEPLOYING SAME

(71) Applicant: Design West Technologies, Inc., Tustin, CA (US)

(72) Inventors: Ryan Hur, Irvine, CA (US); Ramesh Palanisamy, Irvine, CA (US); Berwin Banares, Mission Viejo, CA (US); Maria E. Bauer, Irvine, CA (US); So Nguyen, Stanton, CA (US); Sam De La Torre, Riverside, CA (US); Xavier Ollat, Perris, CA (US)

(73) Assignee: Design West Technologies, Inc., Tustin, CA (US)

( * ) Notice: Subject to any disclaimer, the term of this patent is extended or adjusted under 35 U.S.C. 154(b) by 419 days.

(21) Appl. No.: 17/074,449

(22) Filed: Oct. 19, 2020

(65) Prior Publication Data
US 2021/0349067 A1    Nov. 11, 2021

Related U.S. Application Data

(60) Provisional application No. 62/937,701, filed on Nov. 19, 2019, provisional application No. 62/916,722, filed on Oct. 17, 2019.

(51) Int. Cl.
*G01N 33/00* (2006.01)
*B64D 1/02* (2006.01)
*B64U 101/35* (2023.01)

(52) U.S. Cl.
CPC ..... *G01N 33/0057* (2013.01); *G01N 33/0055* (2013.01); *B64D 1/02* (2013.01); *B64U 2101/35* (2023.01)

(58) Field of Classification Search
CPC .. G01N 33/0057; G01N 33/0055; B64D 1/08; B64D 1/14; B64D 1/12; B64D 1/22; B64D 1/02; B64D 1/04; B65G 1/02; B65G 1/023; B65G 1/026; B65G 1/0442; B65G 1/0478; B65G 1/07; B65G 1/10;
(Continued)

(56) References Cited

U.S. PATENT DOCUMENTS

| | | | | |
|---|---|---|---|---|
| 2,451,479 A | * | 10/1948 | Diehl | B64D 1/04 244/130 |
| 9,738,398 B1 | * | 8/2017 | Wang | G01S 1/725 |
| 10,293,936 B1 | * | 5/2019 | Conn | G05D 1/0027 |

(Continued)

FOREIGN PATENT DOCUMENTS

| | | | | | |
|---|---|---|---|---|---|
| CN | 108152460 A | * | 6/2018 | | |
| JP | 6453655 B2 | * | 1/2019 | | |
| KR | 20180000458 A | * | 1/2018 | | B64C 39/024 |

OTHER PUBLICATIONS

JP-6453655-B2-English (Year: 2019).*
CN-108152460-A-English (Year: 2018).*

*Primary Examiner* — Kristina M Deherrera
*Assistant Examiner* — Fatemeh Esfandiari Nia
(74) *Attorney, Agent, or Firm* — Inskeep IP Group, Inc.

(57) ABSTRACT

A sensor system is disclosed that includes a plurality of sensors, a deployment system for deploying the sensors, a control and charging system for receiving sensor data and optionally charging the batteries within the sensors, and one or more algorithms employed by the sensor system for processing, analyzing, and otherwise using data received by the plurality of sensors.

21 Claims, 40 Drawing Sheets

(58) Field of Classification Search
CPC ... B65G 1/14; B65G 1/18; B65G 1/20; B65G 3/04; B65G 1/00
See application file for complete search history.

(56) References Cited

U.S. PATENT DOCUMENTS

| | | | | |
|---|---|---|---|---|
| 2003/0218540 | A1* | 11/2003 | Cooper | G08B 21/10 340/870.01 |
| 2004/0233055 | A1* | 11/2004 | Canich | G08B 25/004 340/539.26 |
| 2005/0210656 | A1* | 9/2005 | Howard | G01N 33/0009 204/431 |
| 2006/0007009 | A1* | 1/2006 | Hess | G08B 17/113 340/628 |
| 2009/0243855 | A1* | 10/2009 | Prokopuk | G01S 13/825 340/572.1 |
| 2012/0268281 | A1* | 10/2012 | Hojmose | G08B 17/113 340/630 |
| 2014/0096590 | A1* | 4/2014 | Amin | H04W 4/029 73/23.34 |
| 2017/0222382 | A1* | 8/2017 | Peloquin | H01R 27/02 |
| 2018/0244401 | A1* | 8/2018 | Kilian | B64C 25/68 |
| 2019/0047707 | A1* | 2/2019 | Sopper | B65D 81/052 |
| 2019/0082015 | A1* | 3/2019 | Husain | G01S 1/00 |
| 2019/0265082 | A1* | 8/2019 | Zafar | H04Q 9/00 |
| 2019/0300290 | A1* | 10/2019 | Hofer | B65G 37/00 |
| 2019/0322495 | A1* | 10/2019 | Prager | B66F 19/00 |
| 2021/0032026 | A1* | 2/2021 | Lindbo | B65G 1/0464 |

* cited by examiner

CBRNE SENSORS AND SYSTEM FOR MONITORING AND DEPLOYING SAME

RELATED APPLICATIONS

This application claims benefit of and priority to U.S. Provisional Application Ser. No. 62/916,722 filed Oct. 17, 2019 entitled Disposable Sensor for Low Volatile Chemical Agents, and to U.S. Provisional Application Ser. No. 62/937, 701 filed Nov. 19, 2019 entitled UAV Release Mechanism, both of which are hereby incorporated herein by reference in their entireties.

BACKGROUND OF THE INVENTION

The present invention relates generally to the field of chemical, biological, radiological, nuclear, explosive (CBRNE) detection, pharmaceutical-based agents (PBA), non-traditional agents (NTA), and never-seen-before threats (referred generally as agents, toxic agents, or airborne agents, or CBRNE agents in this specification). More particularly, the present invention provides useful and novel systems and methods for detecting these agents.

Chemical and biological detection finds a wide variety of applications, such as detection of toxic warfare agents on a battlefield, in an area around an accidental chemical release, around industrial and manufacturing worksites, law enforcement and anti-terrorist efforts, and environmental and agricultural contamination monitoring.

Currently, chemical and/or biological detection in remote areas, especially on the ground, is primarily performed by deploying standalone sensor systems at predetermined locations. However, these sensor systems have drawbacks. For example, the sensors must be physically deployed by a user, in person, at a desired location. Therefore, if the deployment area already contains toxic agents, the user is immediately placed in jeopardy by performing the deployment. Additionally, any sensing is limited to only that particular location rather than a broader monitoring area. In another example, complex chemical and biological sensor systems tend to be relatively expensive and therefore are typically retrieved for later use. Hence, if the sensor becomes contaminated, damaged, lost, or is difficult to retrieve, it often must be abandoned and replaced with another sensor.

Hence, what is needed is an improved sensor and sensor system that helps address these previously-discussed and other drawbacks.

SUMMARY OF THE INVENTION

The present invention is generally directed to a sensor system that includes a plurality of sensors, a deployment system for deploying the sensors, a control and charging system for receiving sensor data and optionally charging the batteries within the sensors, and one or more algorithms employed by the sensor system for transmitting, processing, analyzing, and otherwise using data received by the plurality of sensors.

One aspect of the present invention is directed to an improved sensor device for CBRNE agents. As described in more detail below, the sensor device includes a number features that may result in improved performance when dropped in a target area, such as shock resistance (i.e., from physical impacts), improved air flow paths over the sensor components, low power communications, low and balanced air drag when dropped, and a center of balance configured to result in a specific orientation when dropped on the ground. Also, this orientation allows positioning the antenna to highest possible level within the sensor housing of the sensor device.

Another aspect of the present invention includes a storage assembly that can be used to retain a plurality of sensor devices for storage, charging, and deployment purposes. In one embodiment, the storage assembly comprises an elongated tube that has a diameter that is roughly the same (or slightly larger) as the sensor device (i.e., the diameter across the widest portion of the housing). In that respect, a plurality of sensor devices 100 can be stacked on top of each other within the tube.

Another aspect of the present invention includes a deployment assembly for the sensor devices. The present embodiment of the deployment assembly may be particularly suitable for arial vehicles such as unmanned arial vehicles (UAVs) but may also be connected to a wide variety of ground vehicles. In this respect, the vehicles can move to a desired target area and then drop one or more sensor devices within the target area. The deployment assembly may removably connect to one or more sensor storage assemblies which allows a plurality of sensors devices to easily be removed or added to the vehicle.

Another aspect of the present invention is directed to a method of deploying a plurality of sensor devices, forming a mesh network with the sensor devices, and relaying data back to a remote, control station.

Another aspect of the present invention is directed to a method of analyzing sensor data from a plurality of deployed sensors and using the sensor data to increase confidence of detection and/or detect the presence of an airborne agent that none of the plurality of deployed sensors are specifically configured to sense. A method is also disclosed of reducing false alarms, increasing the probability of detection, and providing higher accuracy.

Another aspect of the present invention is directed to a method of determining a deployed position of a sensor device by sensing a unique identification of the sensor (e.g., RFID), sensing GPS coordinates at a location with equipment on a deployment system that is not contained within the sensor device, and deploying the sensor device at the location. As a function of time, alarm strength and location of the sensor device, an airborne threat agent movement can be monitored and reported.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
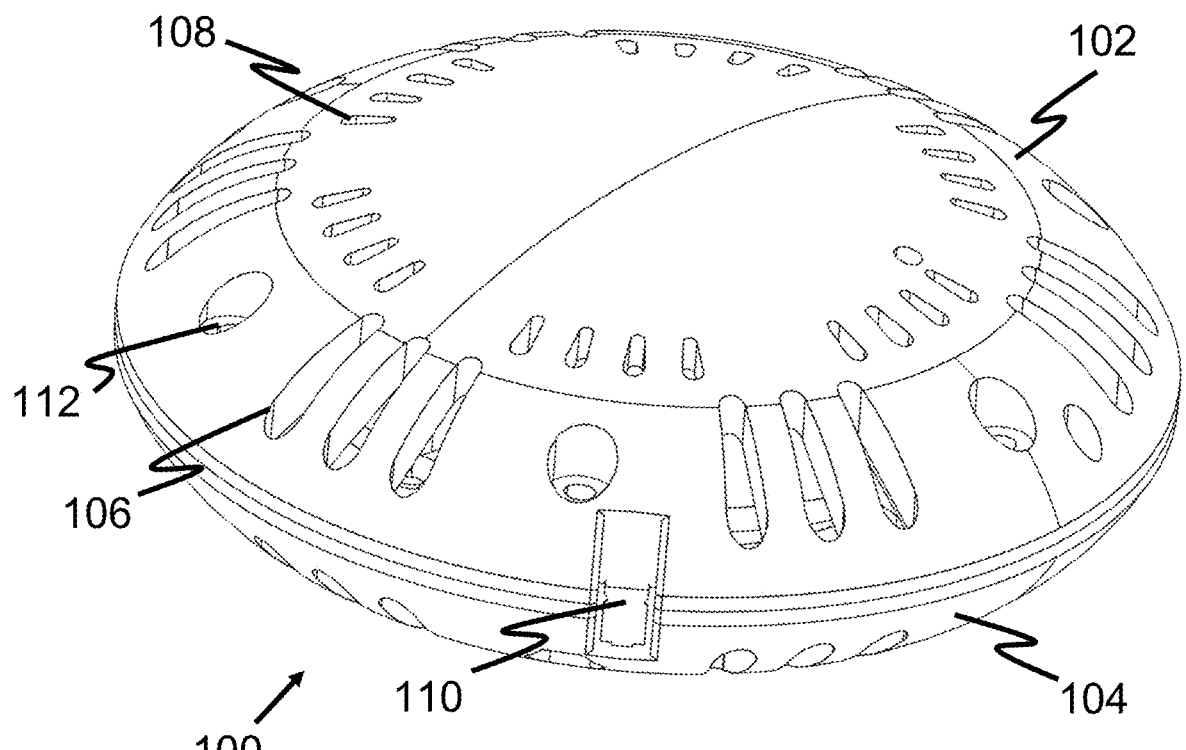
FIG. 1 is a perspective view of a portable sensor device according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements. While different embodiments are described, features of each embodiment can be used interchangeably with other described embodiments. In other words, any of the features of each of the embodiments can be mixed and matched with each other, and embodiments should not necessarily be rigidly interpreted to only include the features shown or described.

The present invention is generally directed to a sensor system that includes a plurality of sensors, a deployment system for deploying the sensors, a control and charging system for receiving sensor data and optionally charging the batteries within the sensors, and one or more algorithms employed by the sensor system for transmitting, processing, analyzing, and otherwise using data received by the plurality of sensors.

One aspect of the present invention is directed to an improved sensor device 100 for chemical and/or biological agents. As described in more detail below, the sensor device 100 includes a number features that may result in improved performance when dropped in a target area, such as shock resistance (i.e., from physical impacts), improved air flow paths over the sensor components, low power communications, low and balanced air drag when dropped, and a center of balance configured to result in a specific orientation when dropped on the ground.

Figure 2:
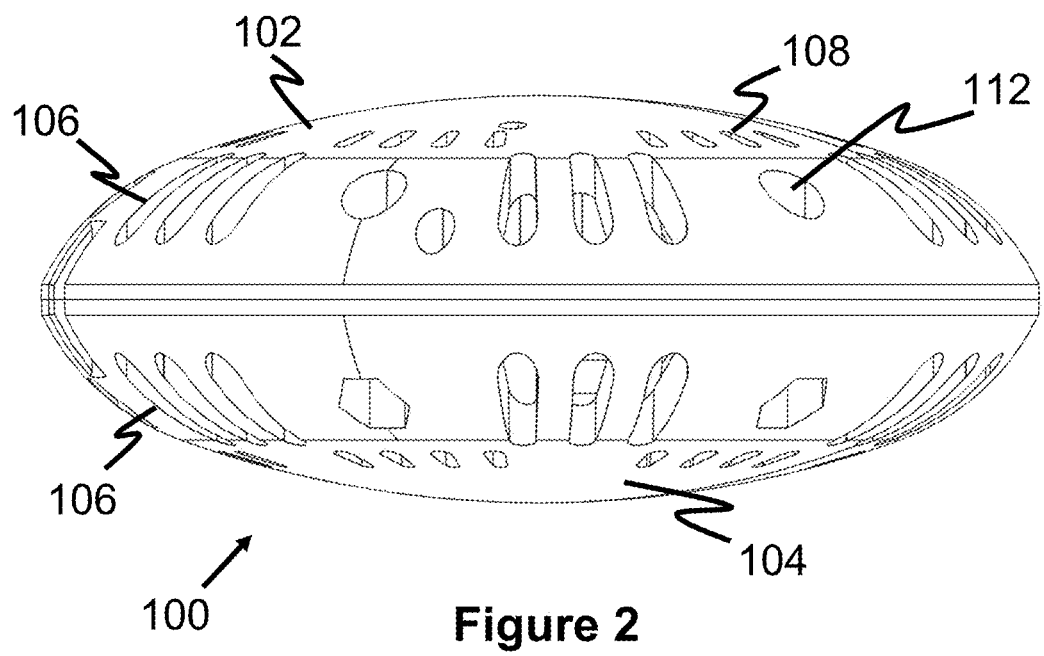
FIG. 2 is a side view of a portable sensor device according to one embodiment of the present invention.
Figure 3:
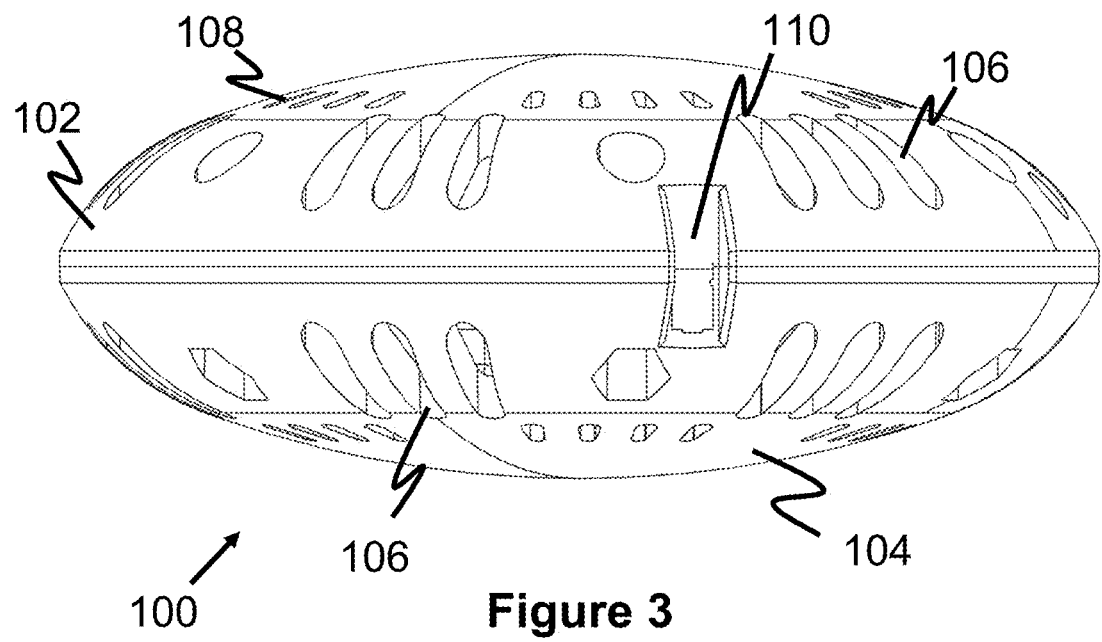
FIG. 3 is a side view of a portable sensor device according to one embodiment of the present invention.
Figure 4:
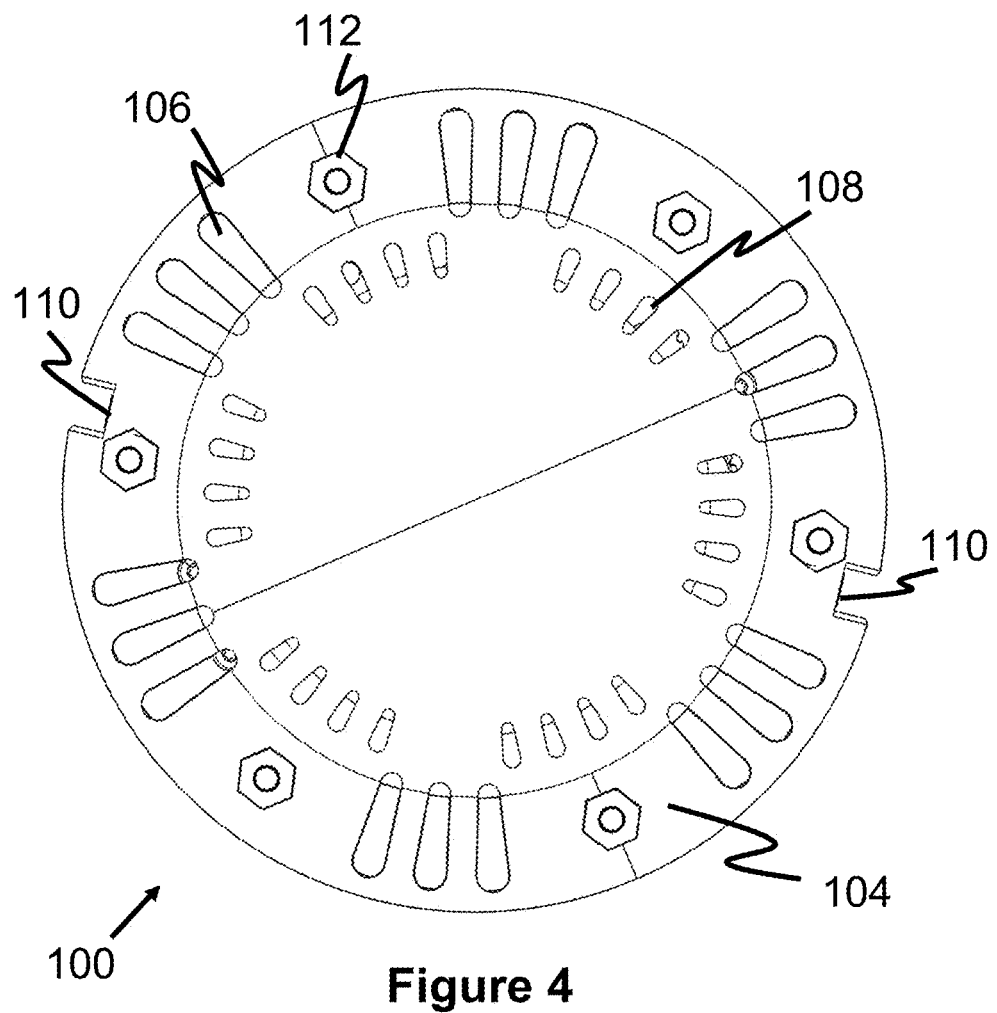
FIG. 4 is a bottom view of a portable sensor device according to one embodiment of the present invention.
Figure 5:
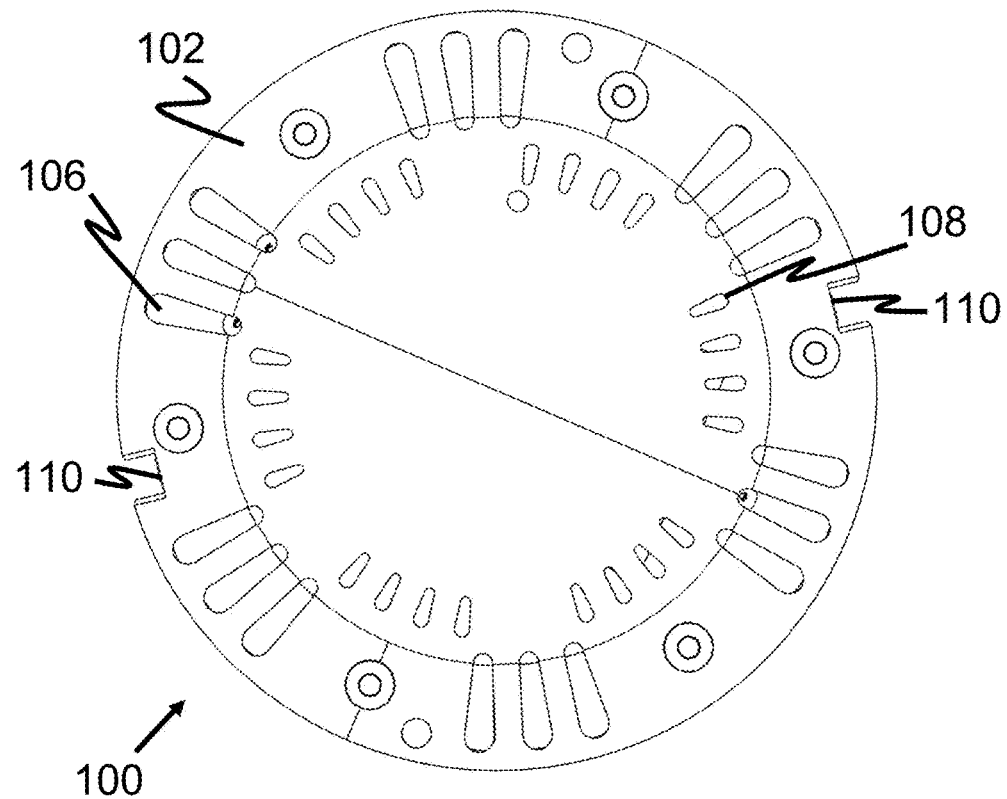
FIG. 5 is a top view of a portable sensor device according to one embodiment of the present invention.
Figure 6:
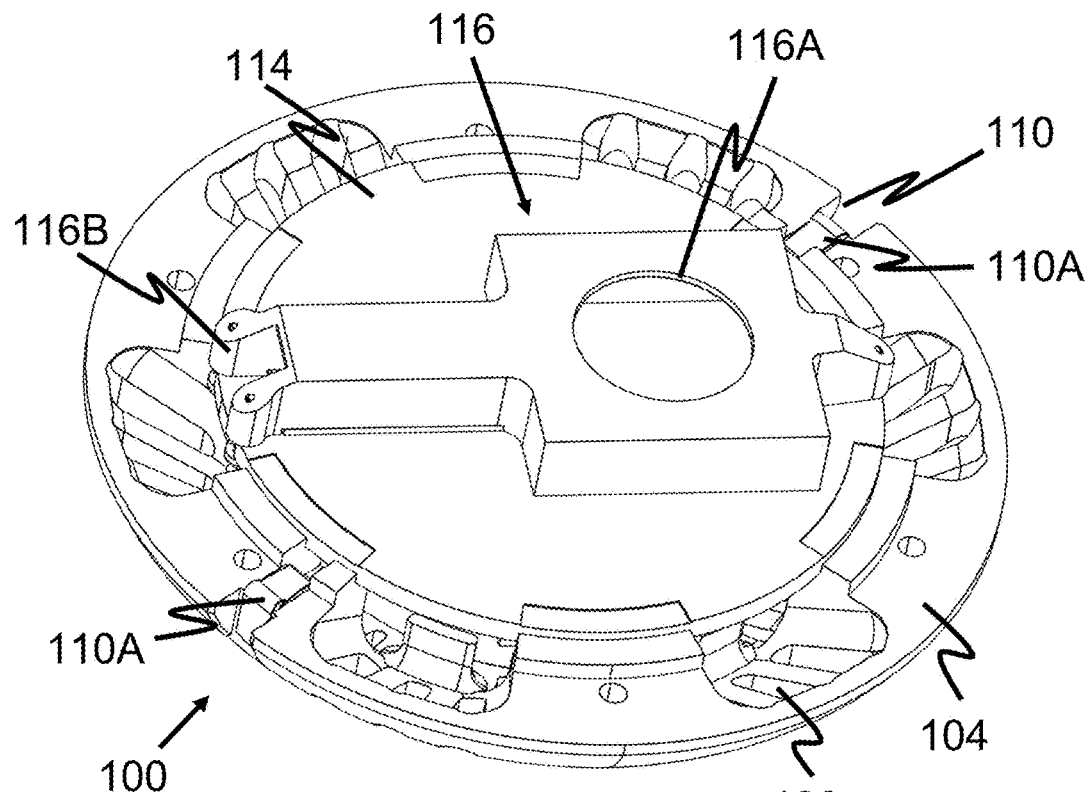
FIG. 6 is an interior view of a portable sensor device according to one embodiment of the present invention.
Figure 7:
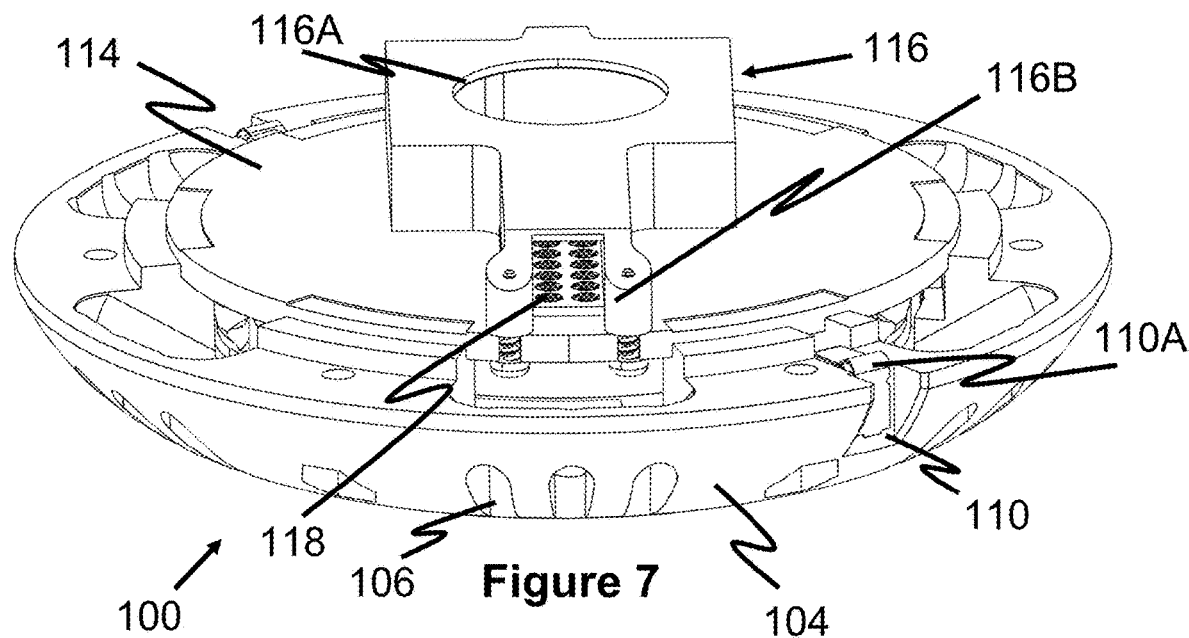
FIG. 7 is an interior view of a portable sensor device according to one embodiment of the present invention.
Figure 8:
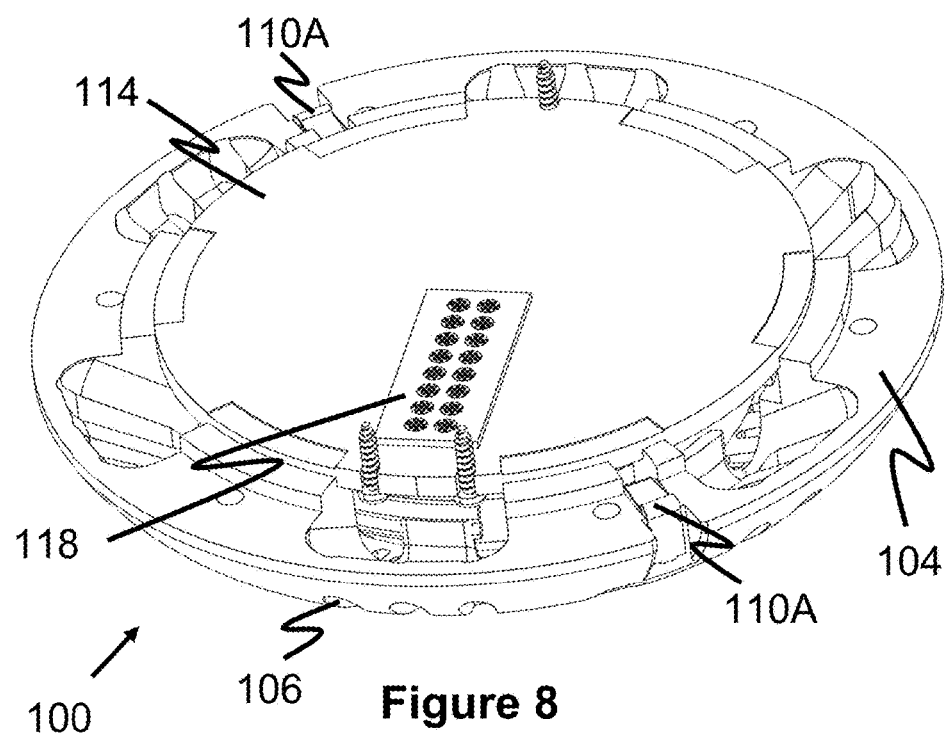
FIG. 8 is an interior view of a portable sensor device according to one embodiment of the present invention.

FIGS. 1-5 illustrate various views of an exterior of the sensor device 100. In one embodiment, the sensor device 100 has a generally circular shape when viewed from the top (FIG. 5) or the bottom (FIG. 4), and an oval shape when viewed from a side perspective (FIGS. 2 and 3). Put another way, the device 100 has a circular disc shape with a symmetrically curved top and bottom surface that are angled downward toward the sides.

Preferably, the shape of the sensor device 100 is such that it lacks corners or hard edges that may create an area of excess stress on the housing when dropped, reducing impact shock on the housing. In that regard, other shapes without corners or dramatically angled edges are also contemplated, such as oval shapes (e.g., similar to a rugby ball). Additionally, while the top and bottom of the sensor device is shown as being relatively symmetrical in shape, asymmetry between the top and bottom is also possible. For example, the bottom may have a more rounded shape and the top may have a relatively flatter shape.

The housing of the sensor device 100 can be composed of a top housing member 102 and a bottom housing member 104 that each makeup about half of the entire housing shape.

In an alternate embodiment, the housing can be composed of two side housing members (i.e., that form a seam that splits down the flatter top/bottom of the device 100). In another alternate embodiment, the housing can be composed of a single housing member that has been entirely formed around the interior components (e.g., injection molded around the electrical components). While the illustrated embodiment has a plurality of screws and screw apertures 112 to allow disassembly, a unitary housing would not otherwise have a user accessible interior. In one embodiment, the housing has a diameter within a range of about 2 to 4 inches (e.g., 2.4 inches) and a height in a range of about 0.75 to 1.5 inches (e.g., about 0.75 inches).

The top and bottom housing members 102, 104 may be composed of a relatively soft and/or elastomeric material, such a thermoplastic elastomer like Santoprene TPV. In one example, the elastomeric material has a Shore hardness between about 80-100, and more preferably a Shore hardness of about 90.

The sensor device 100 also includes a plurality of openings or apertures that open into an interior of the sensor device 100. For example, a plurality of relatively larger, elongated apertures 106 can be positioned around upper and lower surfaces of the device, adjacent to seam between the housing members 102, 104 (i.e., the circumference or "equator" of the device 100). In one example, these apertures 106 are about 0.32 to 0.5 inch long (e.g., about 0.32 inches) by about 0.75 to 0.1 inch wide (e.g., about 0.1 inches). A plurality of smaller openings or apertures 108 can also be included in a similar circular pattern on the top and bottom of the housing, closer to the center of the device 100. In one example, these apertures 108 are about 0.1 to 0.15 inch long (e.g., about 0.13 inches) by about 0.025 to 0.075 inch wide (e.g., about 0.0.5 inches). While 18 apertures 106 and 24 smaller apertures 108 are shown, the number of apertures can vary and scale, depending on the size of the sensor device 100.

Some or all of the apertures 106, 108 can be located at symmetrical positions and have identical or near identical shapes and sizes. In the present embodiment of FIGS. 1-5, all apertures 106, 108 on the top housing member 102 have symmetrically corresponding apertures 106, 108 on the bottom housing member 104. Additionally, the apertures 106, 108 can be located such that they are not directly over or under the electrical components within the device 100, which helps keep water from contacting these electrical components.

These symmetrically corresponding apertures 106, 108 can provide several benefits. First, in the event of dust, rain, snow, or similar precipitation during deployment, much of the water falling into the apertures 106, 108 within the top housing member 102 falls through the interior of the device and out the opposing aperture in the bottom housing member 104. Hence, less water will accumulate within the interior of the device 100.

Additionally, the apertures 106, 108 perform a similar function with air when dropped from an aerial vehicle (e.g., an unmanned arial vehicle or UAV). Specifically, the air passes into the apertures 106, 108 on the bottom housing member 104, through the interior, and out the apertures 106, 108 on the top housing member 102. Since the air can pass directly through the apertures 106, 108, the device 100 may create less drag in the air and therefore more likely to drop evenly and in a desired orientation (e.g., with the top housing member 102 facing upwards). Additionally, these apertures 106, 108 reduce the surface area of the device 100 which also reduces the amount of force gusts of wind may create on the device, again helping to ensure the device 100 lands in a desired orientation.

In an alternate embodiment, the apertures 106, 108 may be offset or asymmetrical from each other on the top and bottom of the device 100. In another embodiment, the apertures 106, 108 may be configured in either their location, size, or shape to help create movement, such as rotation, that may increase the stability of the device as it falls. For example, the sides of each apertures 106, 108 may be "biased" or angled relative to the surface of the housing such that air passing through the apertures 106, 108 is directed slightly to the side (a non-perpendicular direction) to cause the device 100 to spin. The spinning may provide gyroscopic stability.

In another alternate embodiment, the sensor device 100 may include a mechanism to help it move across terrain a short distance as it falls so that it can sense its position while dropping and make adjustments to land in a more desirable area. For example, the sensor device 100 may include one or more movable fins located between opposite apertures 106, 108 that can be used to direct air and therefore the device 100 in a desired lateral direction as it is dropped. In another example, the sensor device 100 may include an external fin, wing, or parachute that is adjustable while the sensor device 100 is dropped. In that respect, the sensor device 100 (or a device controlling it) may be programmed with precise coordinates for landing and then guide itself to that location after being released from an aircraft.

Sensor device 100 may comprise of a parachute via telescoping or foldable antenna. Air opens parachute and extends the anetenna, antenna locks in position at extended position. Once on the floor parachute acts as umbrella while the extended antenna increases the range. In the example of a parachute, such a parachute can be opened by air pressure as it falls or by a timer that deploys and detaches the parachute just prior to landing. The parachute may also be composed of breathable cloth, especially in it remains connected to the sensor device 100 after landing, to allow airflow into the sensor device 100. The slow descent and/or controlled trajectory allows threat mapping in the Z direction in addition to the X-Y plane to provide further information on plume movement modelling.

FIGS. 6-14 illustrate various views of the interior of the sensor device 100. The interior preferably includes a circuit board 114 having a sensor assembly 118 (FIGS. 7 and 8), a microprocessor (or microcontroller) 114A and a wireless transceiver 114B, among other components. In one embodiment, the circuit board 114 further includes a GPS sensing chip that can determine the position of the sensor device 100 based on GPS satellites.

Figure 14:
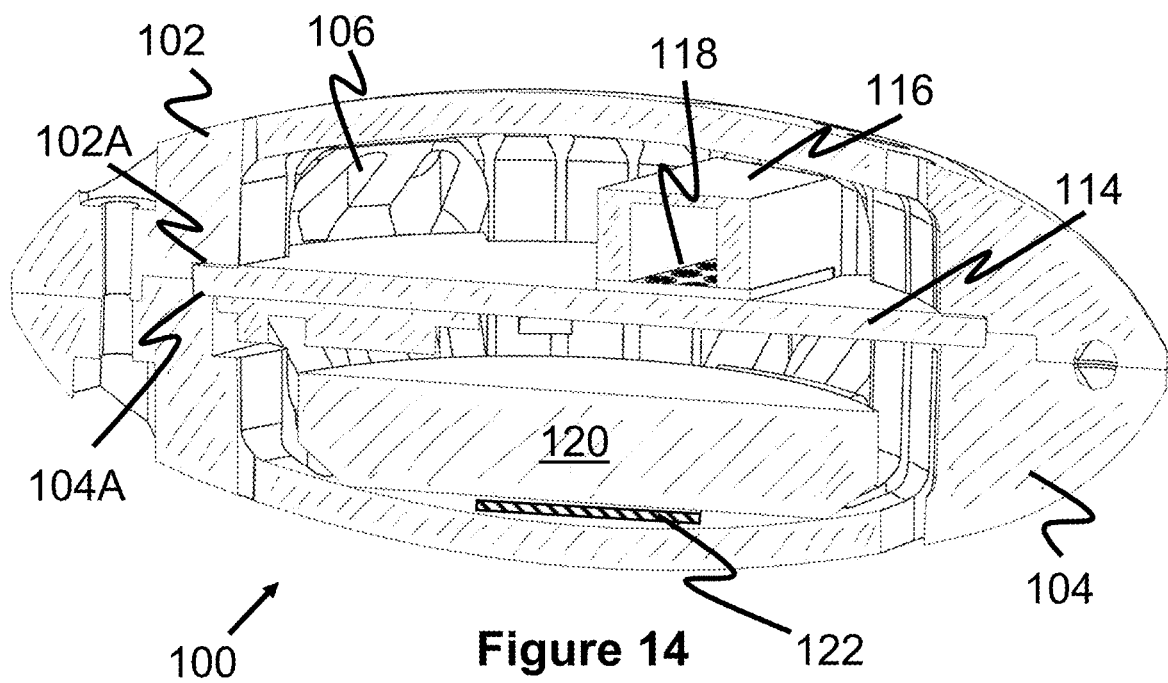
FIG. 14 is a cross sectional view of a portable sensor device according to one embodiment of the present invention.

In one embodiment, the circuit board 114 has a circular shape and is mounted between a gap created by circular recesses 102A and 104A (seen best in FIG. 14). This allows the circuit board 114 to be suspended in the middle of the device 100 and distributes any force it receives upon impact to thereby reduce shock to the components on the board.

The circuit board 114 and its components can all be waterproofed. For example, a PCB conformal coating or layer can be place over the entire circuit board 114 and components, preventing water from interfering with the circuits.

The software of the circuit board 114 (i.e., stored in memory and executed by the processor) can be configured to self-erase and/or self-destruct when a low battery level is sensed, at an end of service life, or when instructed from a base station. Tampering the sensor device 100 may activate the self-erase and/or self-destruct functionality. The self-destruct functionality can be achieved by directing relatively high current to burn-off the critical electronic features. For example, the circuit board may have a component such as a capacitor that is configured to store current and release a relatively high burst of current into components that are not otherwise designed to hand such current.

The circuit board 114 may also have a blower or fan that is part of a collection and concentration assembly 116 (FIGS. 6 and 7) that helps collect/concentrate air by blowing and/or causing evaporation to allow the sensor assembly 118 to better detect chemical or biological agents in the air. In one embodiment, the collection and concentration assembly 116 includes an air inlet 116A which opens to a blower that blows air over the sensor assembly 118 and out the outlet 116B. As seen on the interior surface of the top housing member 102 in FIG. 13, a wall 102B can extend around the assembly 116, helping separate the inlet 116A from the outlet 116B to reduce backflow of air from the outlet 116B back into the inlet 116A. The blower and flow path dimensions are not limited to the discussed drawings but can be modified to shallow flow path for higher flow rate. The fan blower is mounted on circuit board to save space and includes an electromagnetic shielding.

The flow path of the concentration assembly 116 relies on the use of a micro blower which allows the assembly 116 to collect a large number of molecules in a short amount of time. This is furthermore achieved through a shallow flow path (e.g., about 1 mm), increasing the flow velocity in contact with the adsorbent materials in the sensor assembly 118, reducing the distance for diffusion from the bulk to the sensor surface and increasing the concentration during sensing of desorbed analytes through decreased overall volume. To protect the sensor assembly 118 and improve its lifespan as well as to support the containment of molecules within the channel during the sensing event, passive valves can be used at inlet and outlet of the channel. These valves can be comprised of a flexible membrane which is opened through the static pressure supplied by the blower when the latter is turned on. If the blower is off, the valves remain closed. Further protection from dust/dirt/water droplets and other larger contaminants is provided by a barrier consisting of either an open cell sponge material or of a hydrophobic membrane at the air inlet/and outlet openings.

The sensor assembly may include a plurality of sensor elements that are configured to sense one or more of chemical, biological, radiological, nuclear, explosive detection, pharmaceutical-based agents (PBA), non-traditional agents (NTA), and never-seen-before threats (referred generally as agents, toxic agents, or airborne agents, or CBRNE agents in this specification). These can be generally referred to as CBRNE sensors. In one example, these sensors can include Chemical Warfare Agent (CWA) CWA-G nerve agent series, CWA-V nerve agent series, CWA-H blister agent series, CWA Blood Agent series, CWA Chocking Agent series or TICs (e.g. DHS top priority [TIC] toxic industrial chemicals ("TIC" or "TICs") such as Hydrogen Sulfide, Ammonia, Chlorine Sulfur Dioxide, Nitric Oxide, Nitrogen Dioxide, Ethylene Oxide, Carbon Monoxide, Methane, Carbon Dioxide, Phosphine, Methyl Bromide and Hydrogen Cyanide, Hydrogen Chloride but not limited to the said TICs). The sensor assembly may also include IP54 membrane to prevent dust and water on one or more sensors. Additional details about the sensor assembly 118, sensor types, and related components can be found in U.S. Pat. Nos. 9,804,109 and 10,330,617; and U.S. Publication 2018-0028846, the contents of which are hereby incorporated by reference. In addition to the blower within the concentration assembly 116, additional mechanisms may be included to enhance sensing of agents in a low power manner.

Figure 58:
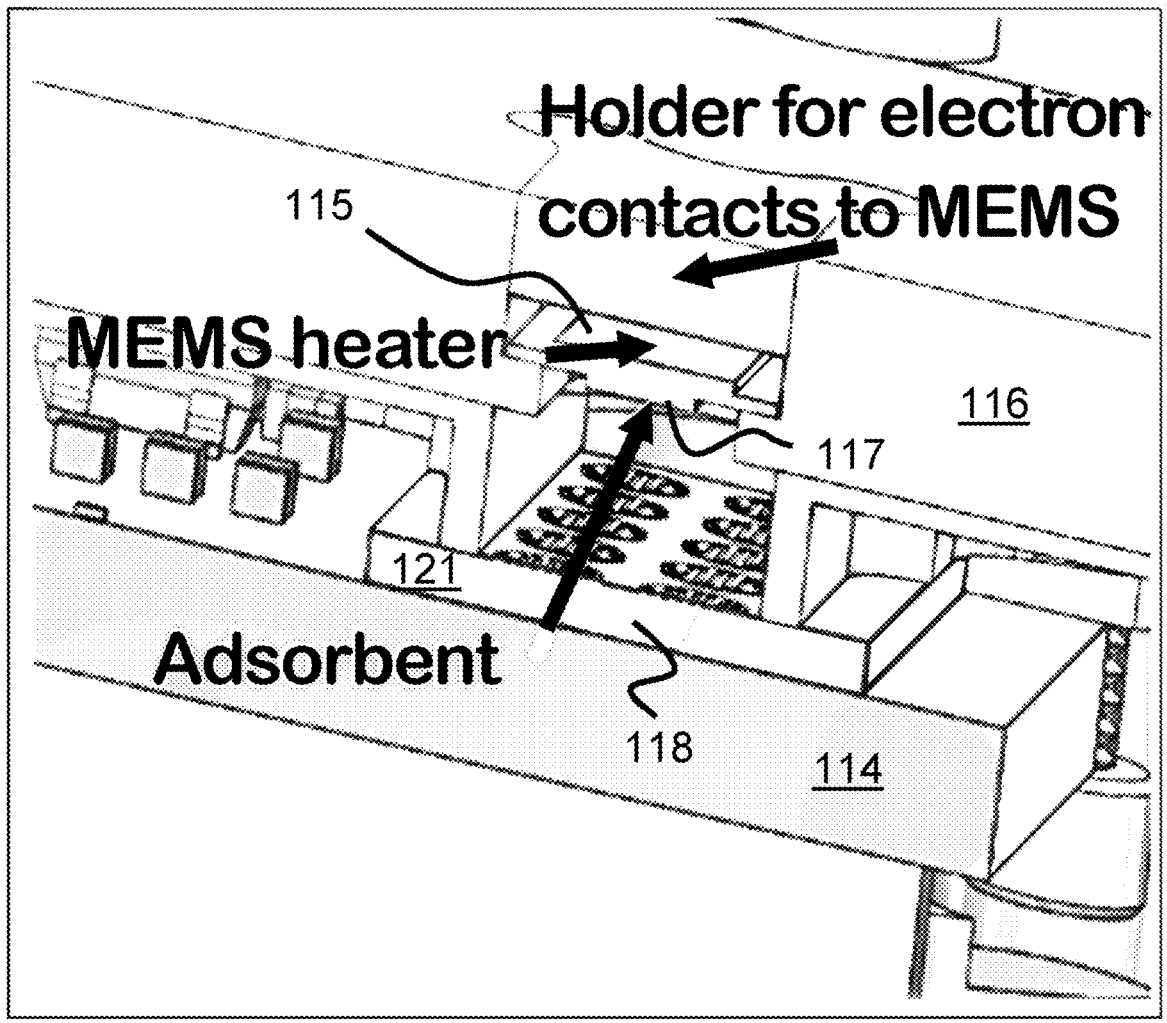
FIG. 58 is a view of a preconcentration devices according to one embodiment of the present invention.
Figure 59:
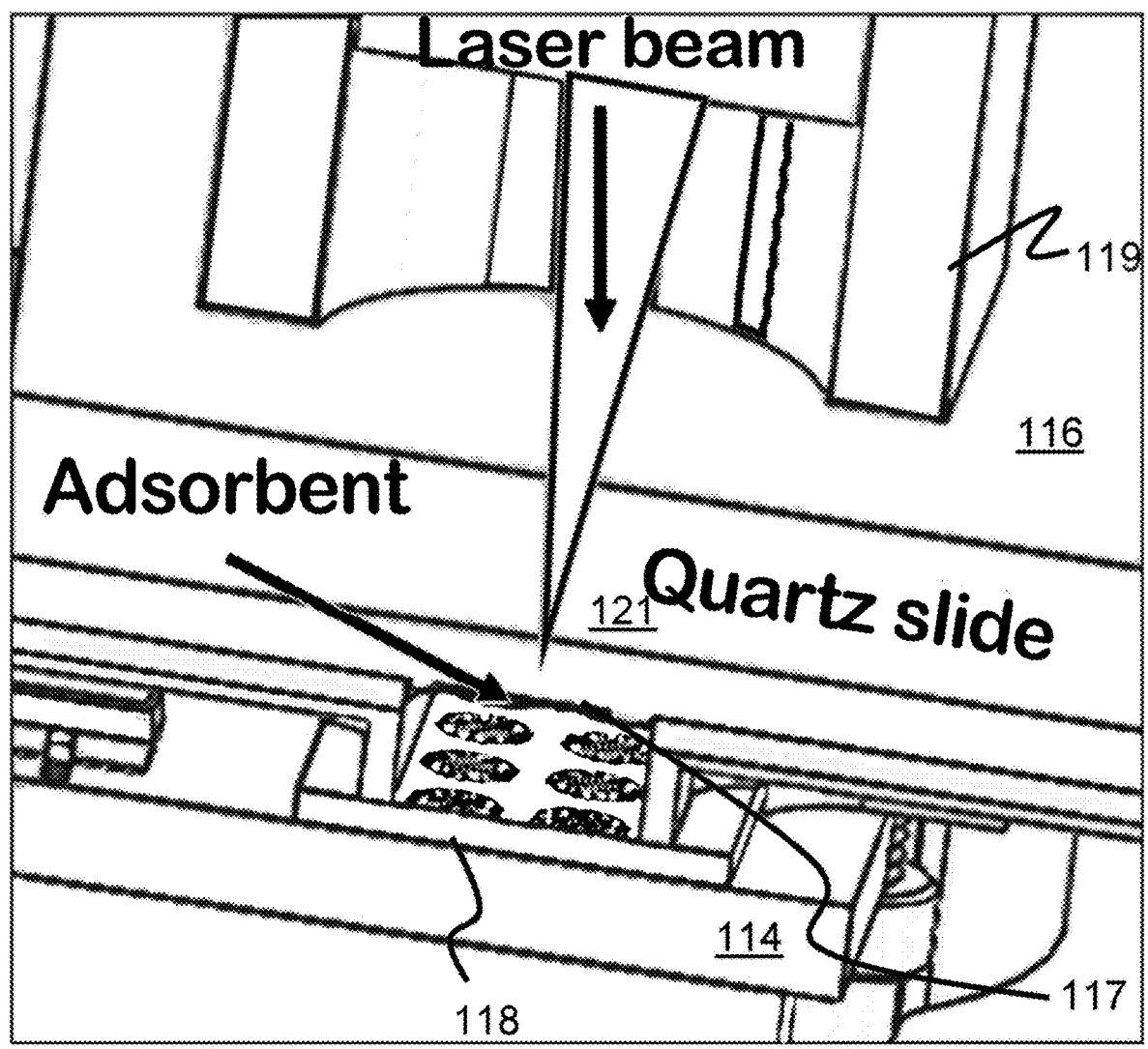
FIG. 59 is a view of a preconcentration devices according to one embodiment of the present invention.
Figure 60:
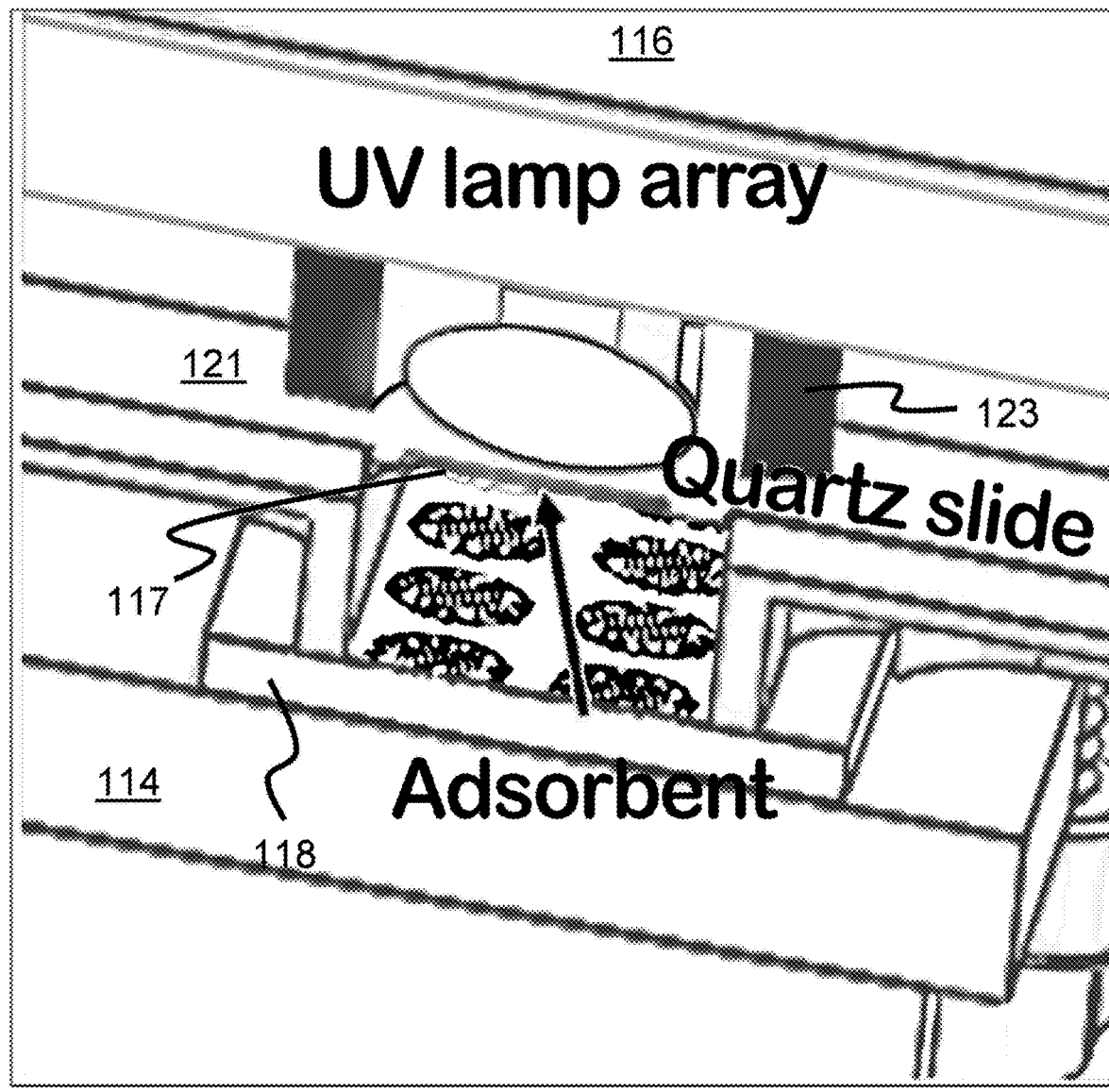
FIG. 60 is a view of a preconcentration devices according to one embodiment of the present invention.
Figure 61:
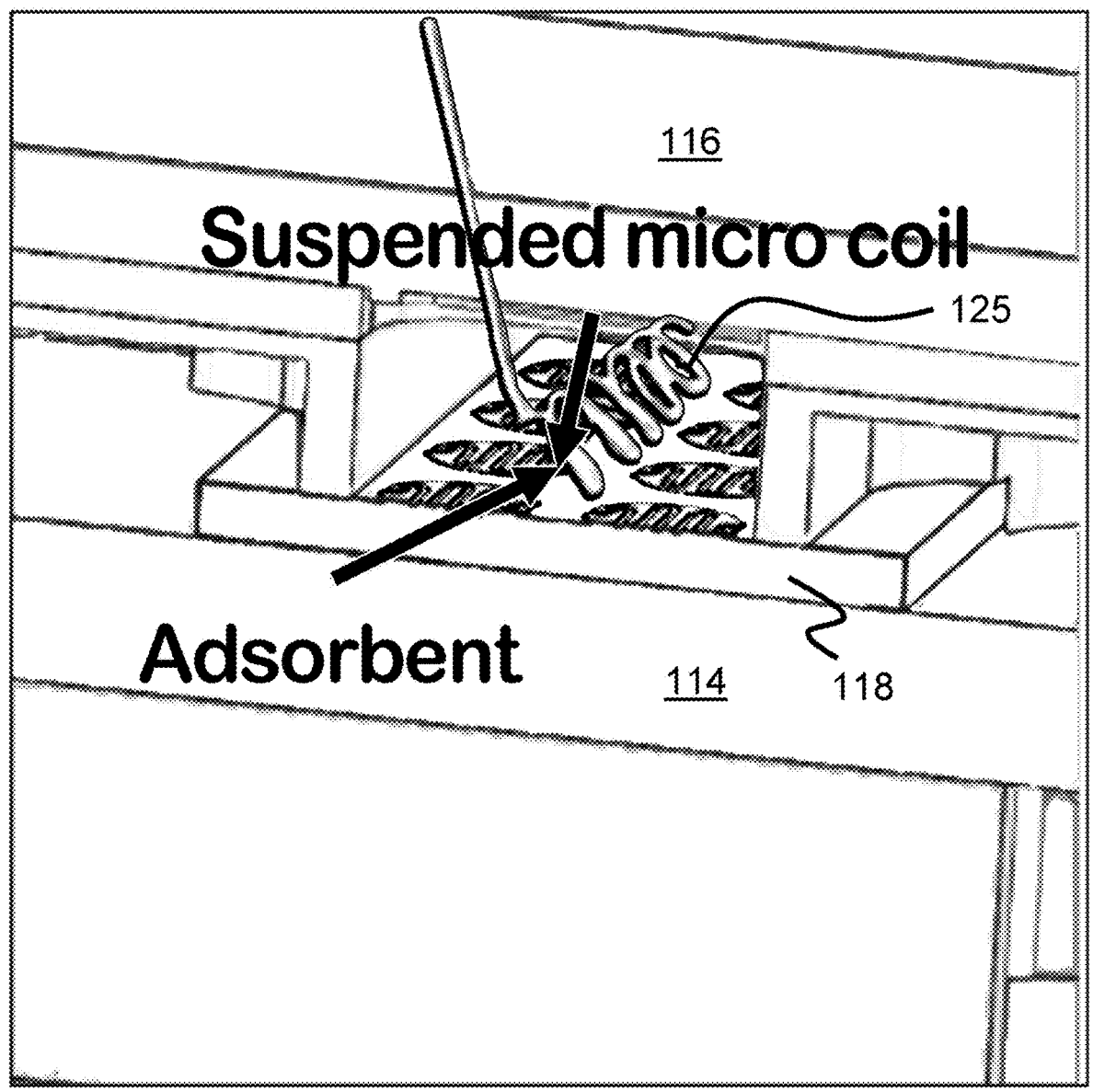
FIG. 61 is a view of a preconcentration devices according to one embodiment of the present invention.

The first approach is illustrated in FIG. 58 and includes a microelectromechanical systems (MEMS) chip 115 which contains a conductive trace through which current flows to generate heat. In one embodiment, the chip 115 can be fixed above the sensor assembly 118. In this approach heat energy transfer is performed by conduction. In close proximity to this trace, either on the backside of the chip or separated from the trace through a thin layer, is a specific adsorbent material 117 which acts to accumulate chemical agents while the adsorbent is at ambient conditions. Once current flows through the MEMS trace, the adsorbent material is heated and releases the chemical agent molecules which can then be sensed at a surface of the sensor assembly 118 (e.g., carbon nanotube sensor surface). To achieve the highest concentrations while reducing cycle times, the time to ramp up the temperature to about 250° C. is reduced and the blower is turned off. Transport of molecules from the adsorbent material to the sensor surface relies on diffusion and is accelerated through temperature gradients between the heater and sensor surface. Typically, MEMS chips 115 are etches or traces are deposited on very thin chips to reduce heated mass and speed up cycle times.

The second approach is comprised of a laser device 119 shining through a transparent material such as a quartz slide 121 and focusing onto the adsorbent coating 117 on the opposed surface if this quartz slide 121. In this method, energy is transferred by photons. Because the adsorbent material 117 is black, it absorbs the laser energy and is rapidly heated, thus releasing any adsorbed molecules towards the sensor assembly 118. As in the case of the MEMS heater 115, the molecules reach the sensor surface based on diffusion and are there detected.

The third approach is based on utilization of one or more UV lamps 123 which are mounted as an array of lights on a circuit board 114 in the ceiling of the flow channel assembly 116, separated either with a quartz slide 121 which is coated with adsorbent material 117 or the UV-lamps 123 are directly coated with adsorbent material (no quartz slide in this case). The energy supplied by the UV lamps enables desorption and diffusion moves molecules to sensors. In this case the energy level is so high that a chemical bond can be broken which helps to release chemisorbed chemical agents from the absorbent materials. The energy is optimized to break van der Waals bond, hydrogen bond and weak $\pi$-$\pi$ bonds and does not break the $\sigma$ bonds.

In a fourth approach, a suspended micro coil 125 of about 40 mm uncoiled total length is coated with adsorbent material 117 and for desorption is applied a current to generate heat, thereby releasing materials towards the sensor assembly 118. As with the other approaches, the coil can be located in the flow path of the concentration assembly 116.

Figure 15:
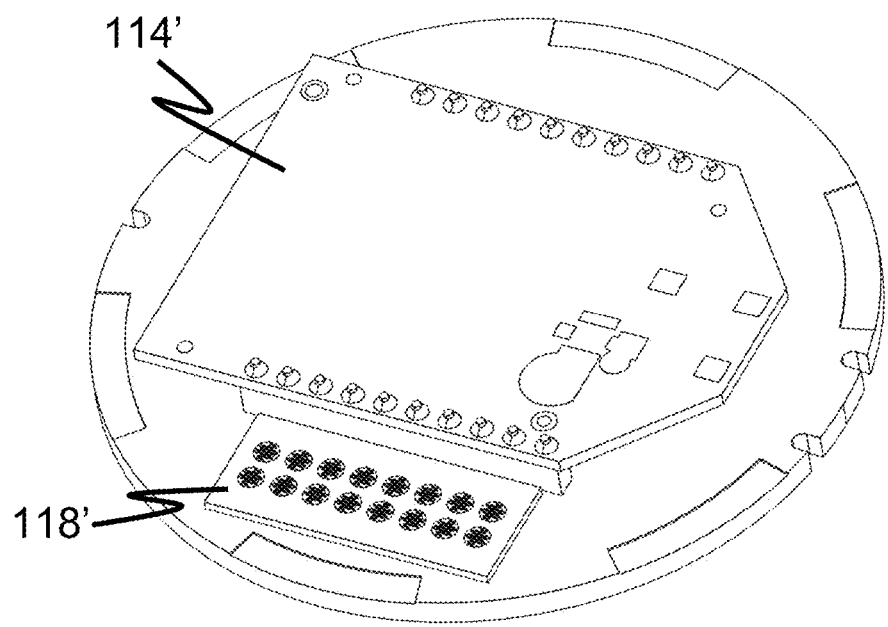
FIG. 15 a view of circuit board of a portable sensor device according to one embodiment of the present invention.
Figure 16:
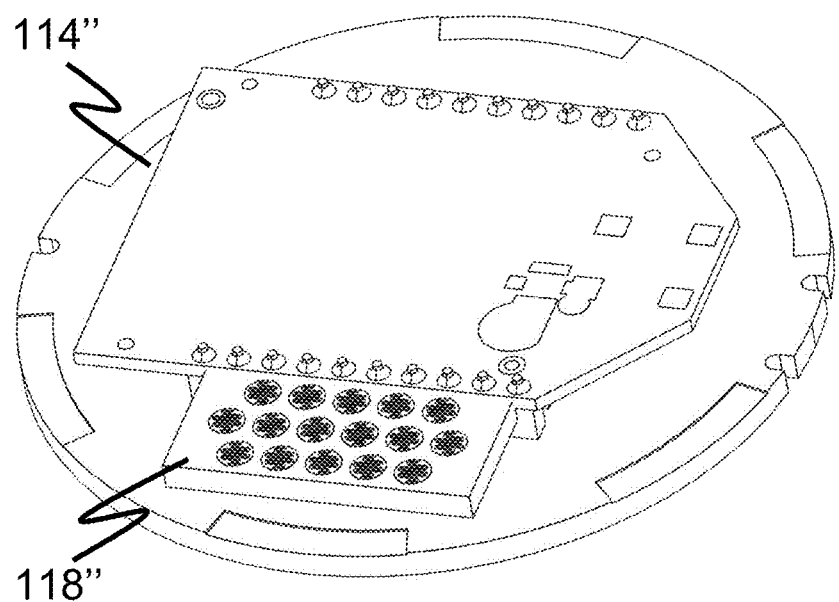
FIG. 16 a view of circuit board of a portable sensor device according to one embodiment of the present invention.

In the alternate circuit board embodiments 114' and 114" shown in FIGS. 15 and 16, a concentration assembly may not be present and the sensor assemblies 118; and 118" can allow ambient contact with outside air without any type of concentration. Additionally, the sensor assembly (i.e., the array of several different sensors) can be of different sizes (e.g., 118' vs 118") and located in different positions on the board 114', 114" vs board 114. For example, the sensor assemblies may each include several identical rows of sensor elements (e.g., 2 or 3) that allows redundancy within a sensor.

The microcontroller 114A is configured to control the operation of the sensor 100 and its components, and primarily record and transmit sensor data. The wireless transmitter 114B is connected to an antenna which is preferably located near the top of the internal cavity of the sensor 100 (e.g., can be adhered to the top surface of the top housing member 102 or can be embedded via the molded design of the top housing member 102). The antenna can be formed into a spiral, wheel, or star shaped pattern of RF wire. In another embodiment, the antenna can be configured to telescope out of the housing over deployment. The wireless transmitter 114B can transmit on any known frequency, such as 900 mhz. The wireless transmitter 114B and microprocessor 114A may also transmit according to any known protocols but may be especially effective utilizing a mesh network protocol. In that regard, each sensor device 100 can both transmit its own data/messages and repeat those of nearby sensor devices 100. In that regard, some sensor devices 100 can be configured to have a more powerful wireless transceiver and battery (as well as memory storage) so that it can collect data from other sensor units 100 and then relay all of that data to a base receiver unit that is a relatively larger distance away. To further conserve battery life in a mesh network, the mesh protocol can be configured to have periods of low power (no communication) and time windows of communication. All or selected sensor devices 100 in a mesh network can be instructed to sleep or wake synchronously to route alarms through mesh. The top housing 102 can embed the antenna by molding a spiral, wheel, or star shaped pattern of RF wire, or the parachute can act as an antenna where the antenna can be deployed at drop by air filling the parachute. The parachute and/or telescope antenna can be opened by air pressure as it falls. Or by a timer that deploys the antenna and may detach the parachute as it descends, prior to landing.

Figure 9:
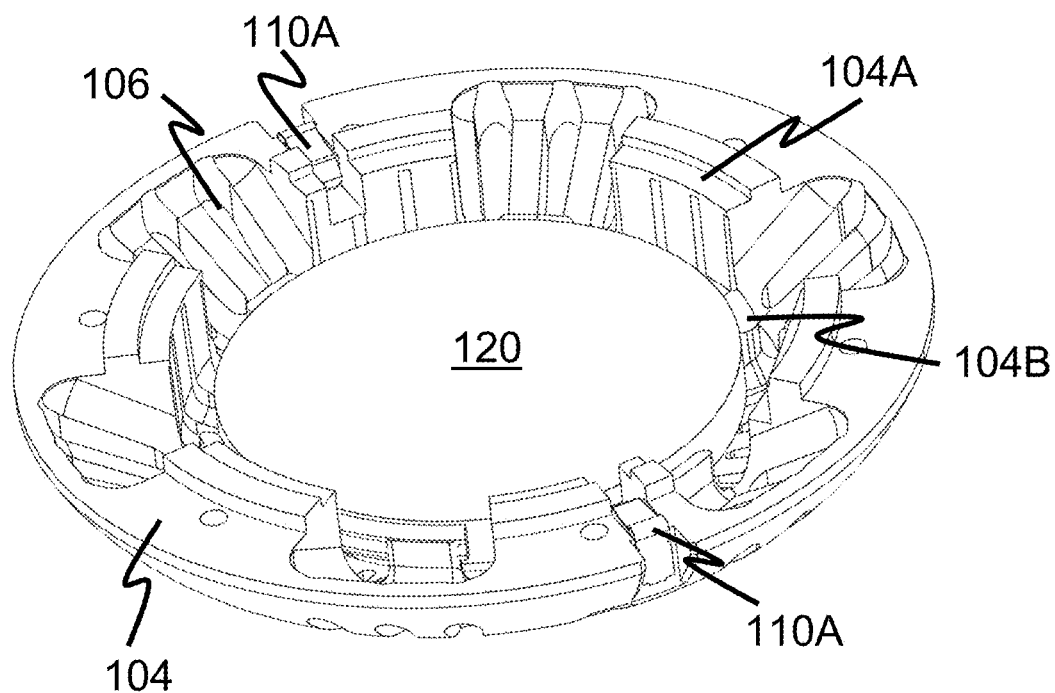
FIG. 9 is an interior view of a portable sensor device according to one embodiment of the present invention.
Figure 10:
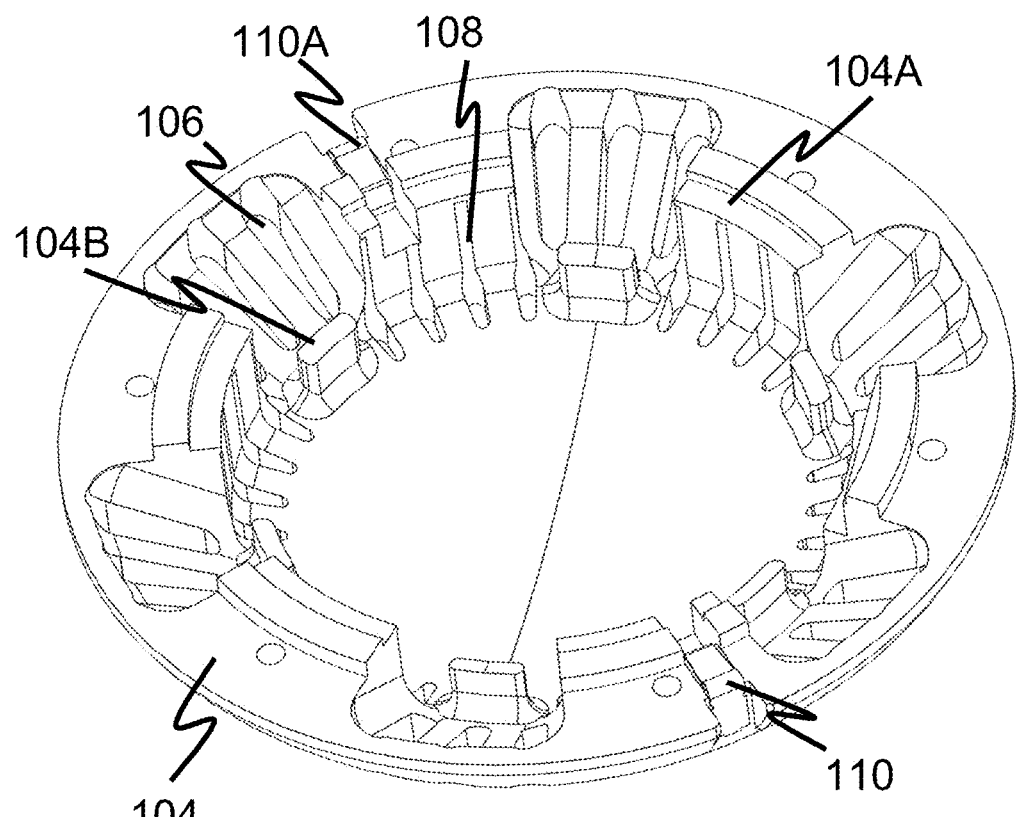
FIG. 10 is an interior view of a portable sensor device according to one embodiment of the present invention.
Figure 11:
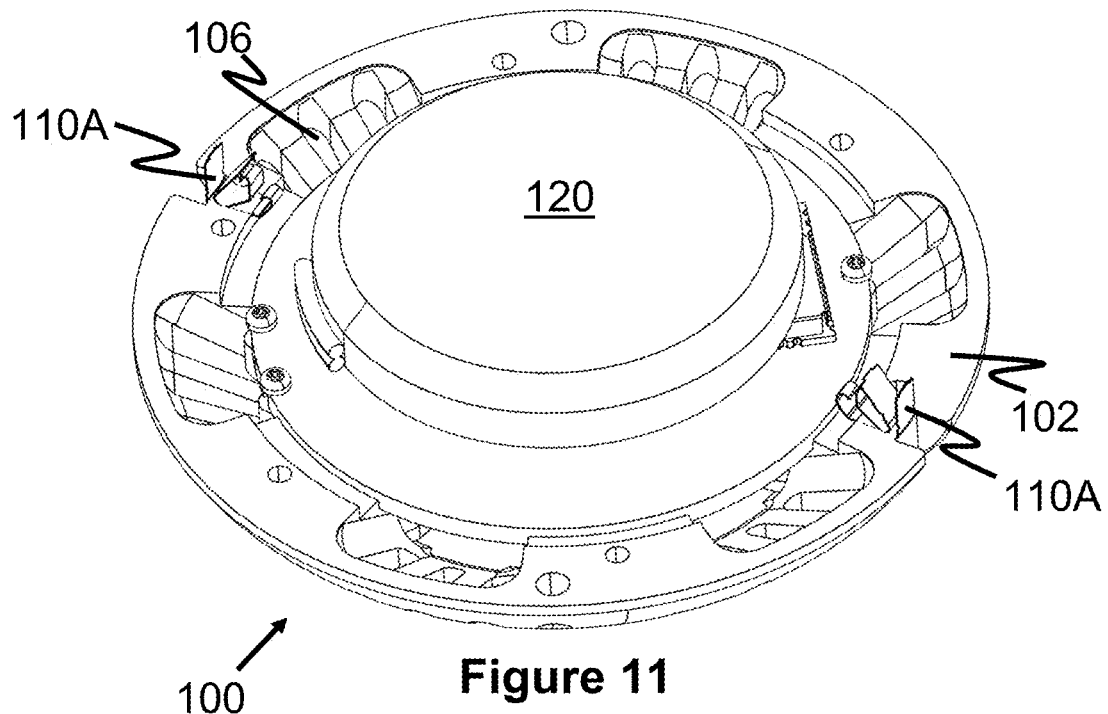
FIG. 11 is an interior view of a portable sensor device according to one embodiment of the present invention.
Figure 12:
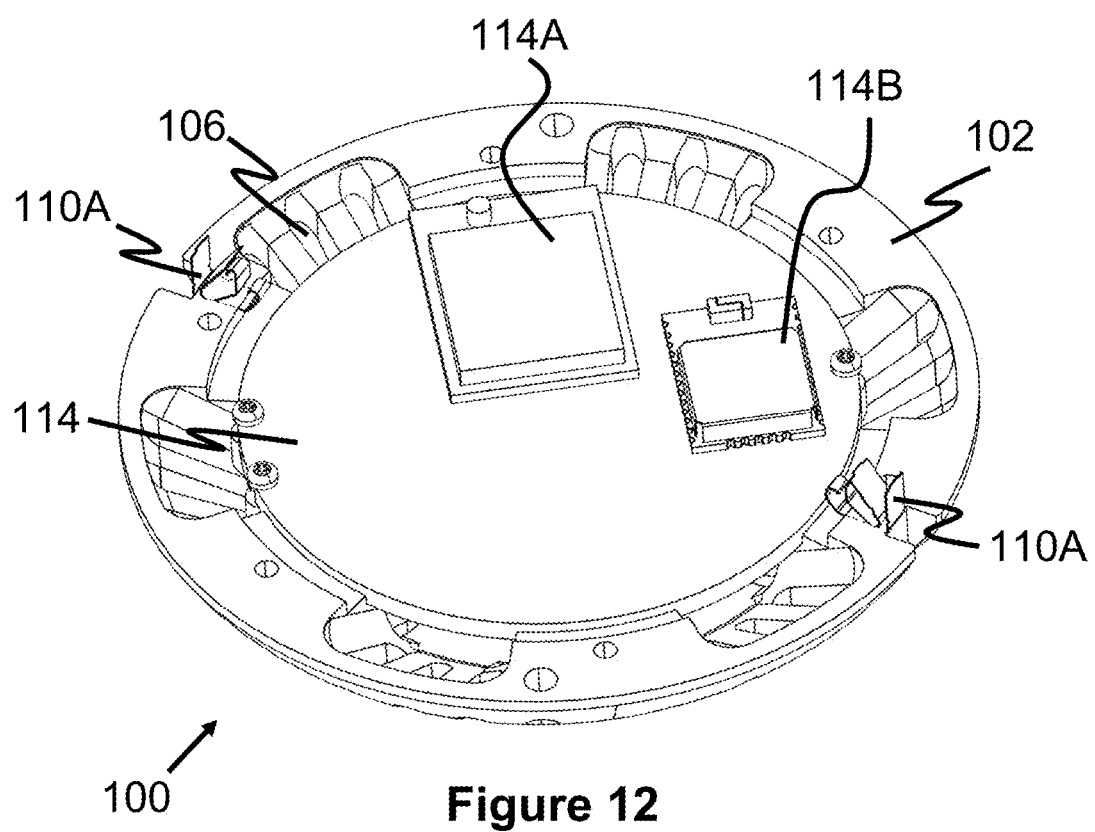
FIG. 12 is an interior view of a portable sensor device according to one embodiment of the present invention.
Figure 13:
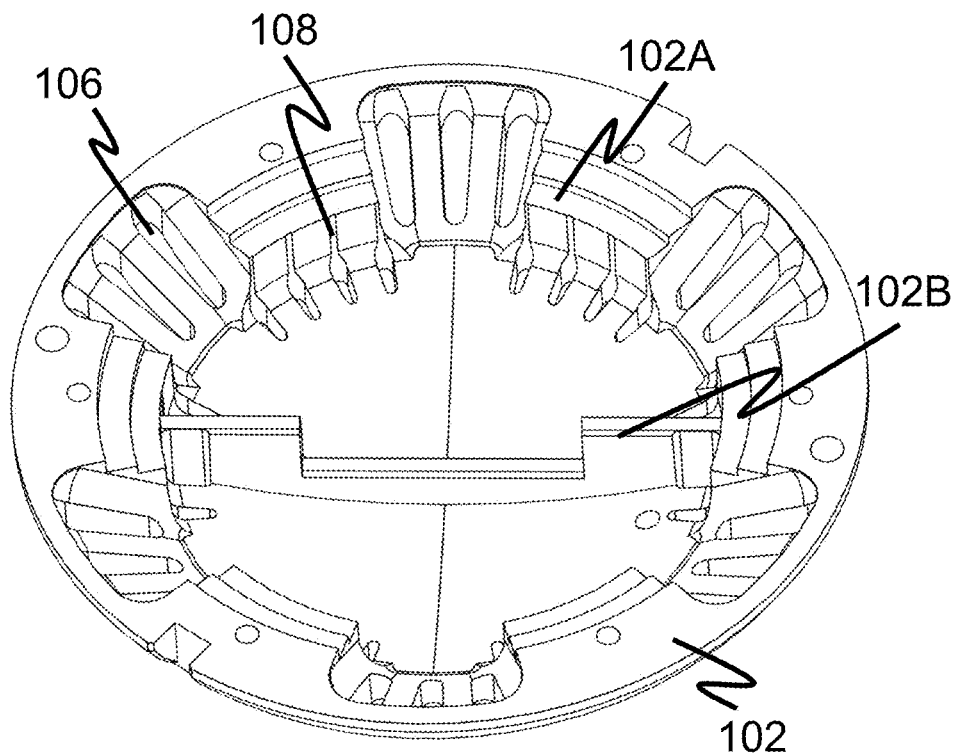
FIG. 13 is an interior view of a portable sensor device according to one embodiment of the present invention.

As best seen in FIGS. 9, 10, and 14, the sensor unit 100 includes a battery 120 that can be engaged against the underside of the bottom housing member 104. In one embodiment, the bottom housing member includes a plurality of legs or raised shapes 1048 that engage the sides of the battery and help keep it in place. The raised shapes 104B and/or the lower surface of lower housing member 104 can be adhered to the battery 120. As seen in FIG. 14, a resilient or compressible pad (e.g., neoprene foam) can be located between the lower side of the battery 120 and the lower surface of the lower housing member 104 to help reduce any shock or jarring force when the sensor device 100 impacts the ground. As also seen in FIG. 14, the battery 120 is fixed at a distance from the circuit board 114 above it to further prevent any small movement by the battery 120 from damaging the circuit board 114.

Since the battery 120 is the heaviest component of the sensor device 100, fixing it at a position along the bottom of lower housing member 104 creates a center of balance towards the bottom of the sensor device 100. In this respect, the senso device 100 tends to fall through the air with its bottom facing downward toward the ground. Additionally, as the sensor device 100 contacts the ground and bounces or rolls, the offset battery position also tends to cause the sensor device 100 to orient itself with its upper housing member 102 directed upwards and its bottom housing member 104 oriented downward towards the ground. Hence, more predictable air flow paths and the highest possible antenna positions can typically be achieved.

As seen in FIGS. 1-14, the upper housing member 102 and lower housing member 104 form two vertical channels 110 having a conducting electrodes 110A that are connected to a charging circuit on the circuit board 114 and ultimately the battery 120. As described in more detail later in this specification, these channels 110 can be used to engage charging electrodes for charging the battery. In an alternate embodiment, the sensor device 100 may not include the charging channels 110, instead having a non-rechargeable battery within it. In such an arrangement, the sensor unit 100 may include a mechanism that interrupts the electrical connection between the battery 120 and the circuit board 114 until removed. For example, the sensor device 100 may include a plastic strip interrupting an electrical pathway to a primary, non-rechargeable battery and which can be pulled out from the device to cause the electrical pathway to the battery 120 to be completed and thereby activate the sensor device 100. This can be achieved by anchoring the plastic strips inside the base station or in the storage assembly 150. In another embodiment, the sensor device 100 may include a solar panel on its top surface for charging the battery 120. This solar panel may be used in addition to the charging channels 110 or as an alternate approach.

FIGS. 17-24 illustrate various views of a storage assembly 150 that can be used to retain a plurality of sensor devices 100 for storage, charging, and deployment purposes. In one embodiment, the storage assembly 150 comprises an elongated tube 152 that has a diameter that is roughly the same (or slightly larger) as the sensor device 100 (i.e., the diameter across the widest portion of the housing). In that respect, a plurality of sensor devices 100 can be stacked on top of each other within the tube 152.

The tube 152 is composed of a rigid material, such as metal or plastic. In one embodiment, the tube includes a plurality of apertures 152A along the length of the tube 152. The apertures 152A preferably are relatively large but also in a manner and shape that prevents the sensor devices 100 from falling out. Put another way, the tube 152 has a relatively high porosity or aperture-to-material ratio so as to maximize exposure of the plurality of sensor devices 100. This exposure can allow the sensor devices 100 to begin actively sensing prior to their final deployment, such as while they are traveling to a destination via ground or air transportation, as discussed later. In one example, the tube 152 has a length within a range of about 5-15 inches (e.g., 10.5 inches), a diameter within a range of 1-5 inches (e.g., 2.5 inches), and a plurality of apertures 152A having a length of about 2-4 inches (e.g., 2.5 inches) and a width of about 0.25-0.75 inch (e.g., 0.75 inches). The apertures 152 can be oval, circular, rectangular, square, or almost any similar shape. These example dimensions can be changed and scaled accordingly.

Figure 17:
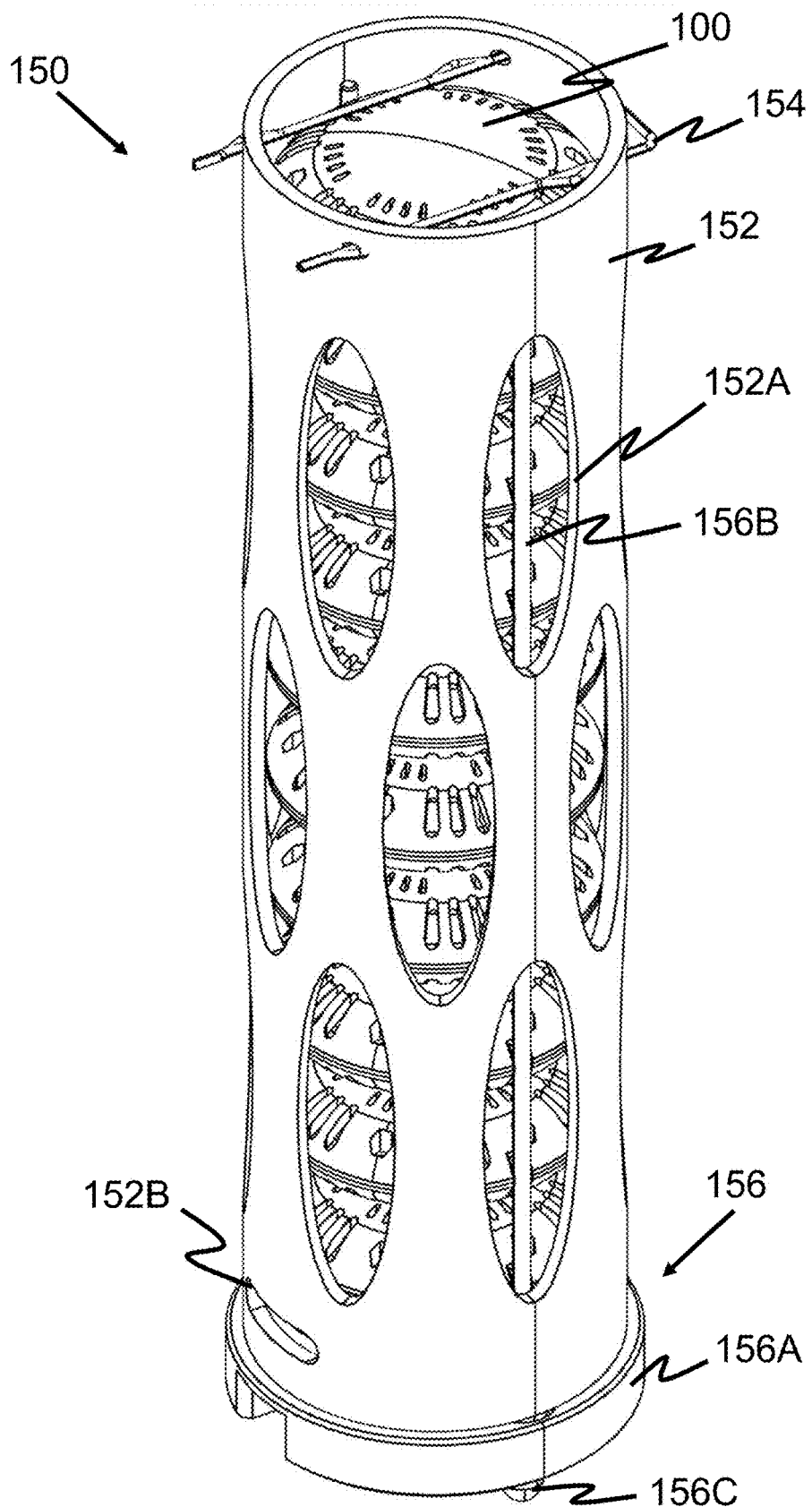
FIG. 17 is a perspective view of a storage container for a plurality of portable sensor devices according to one embodiment of the present invention.
Figure 18:
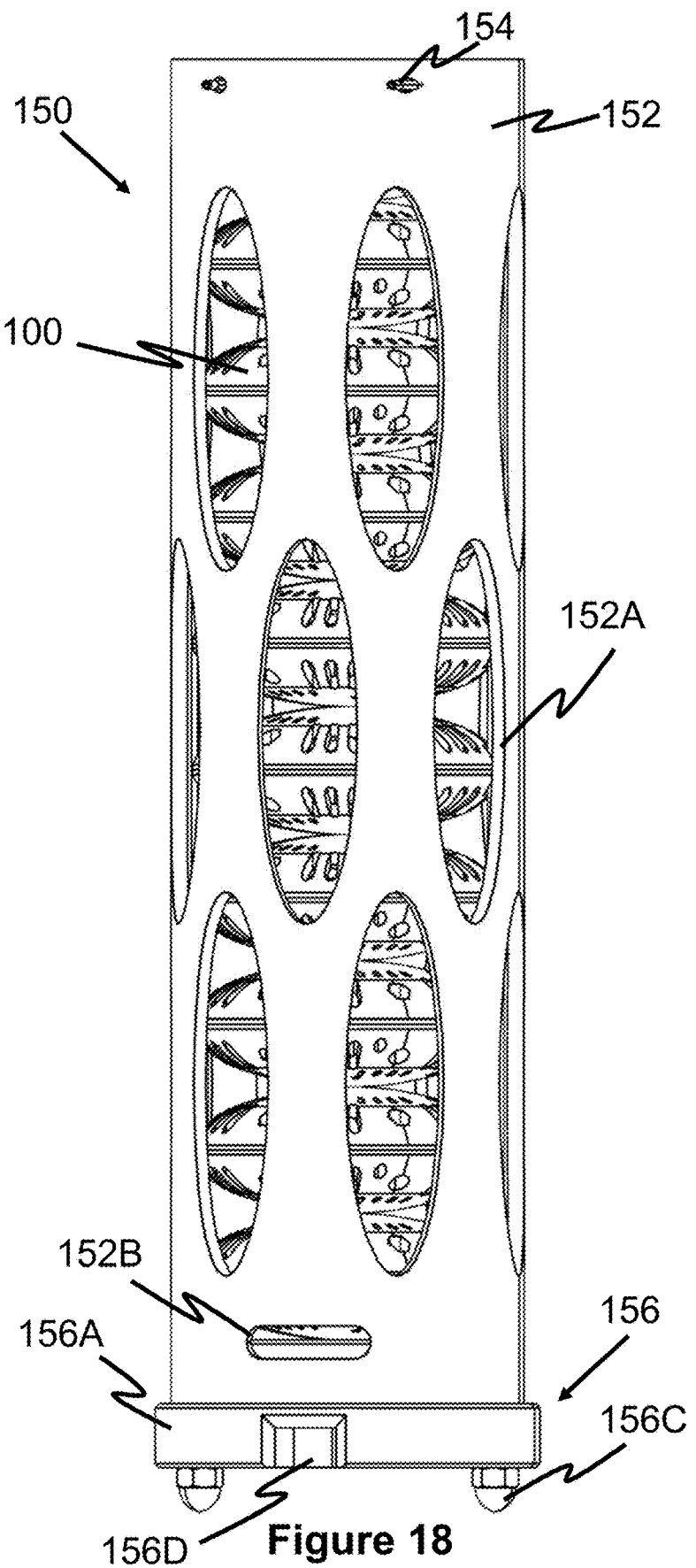
FIG. 18 is a side view of a storage container for a plurality of portable sensor devices according to one embodiment of the present invention.
Figure 19:
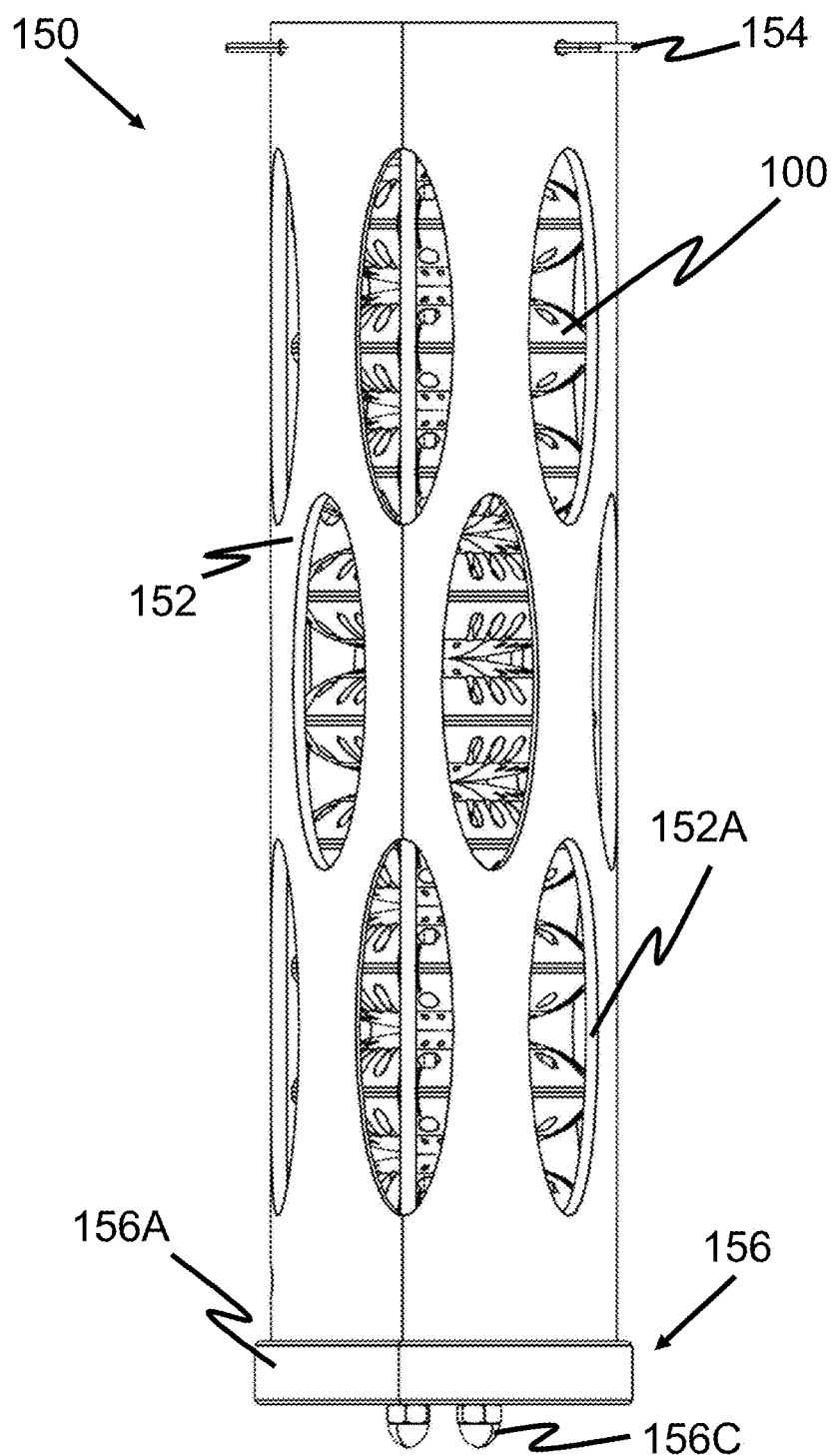
FIG. 19 is a side view of a storage container for a plurality of portable sensor devices according to one embodiment of the present invention.
Figure 20:
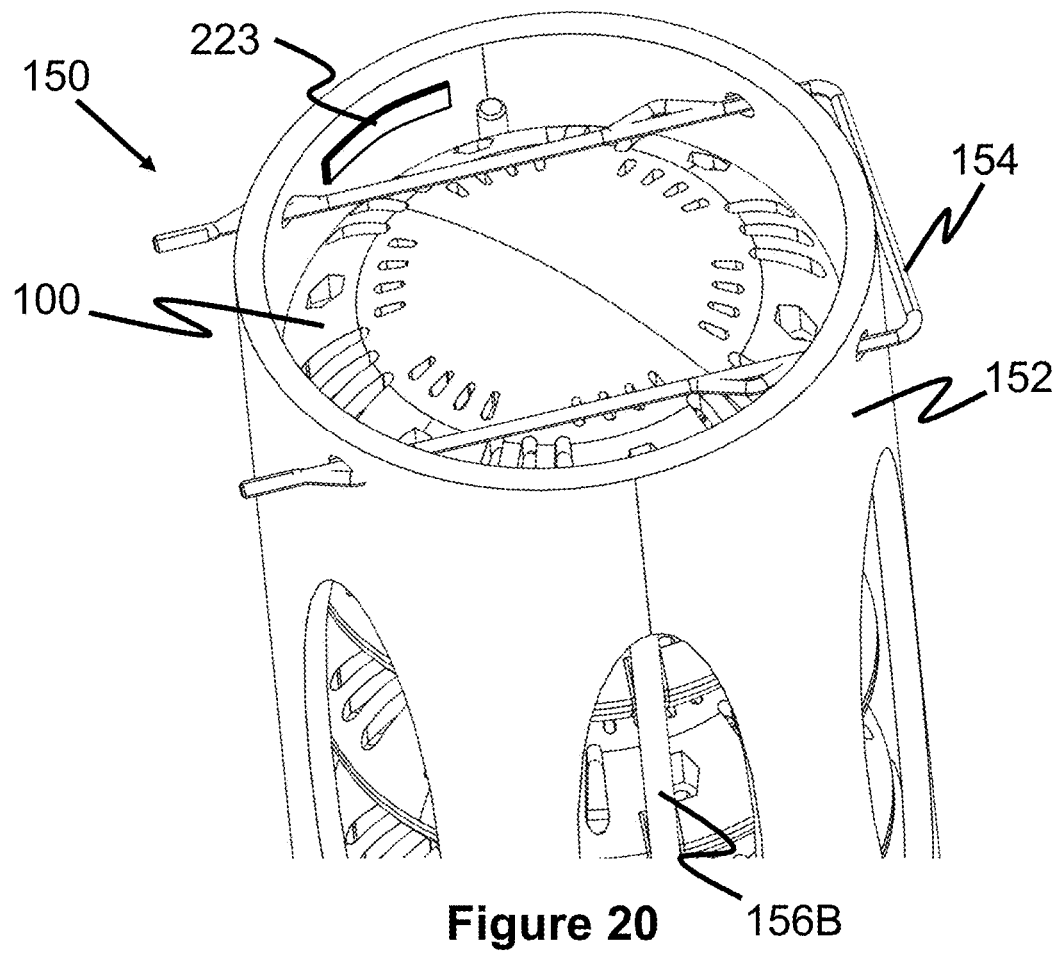
FIG. 20 is a bottom perspective view of a storage container for a plurality of portable sensor devices according to one embodiment of the present invention.
Figure 21:
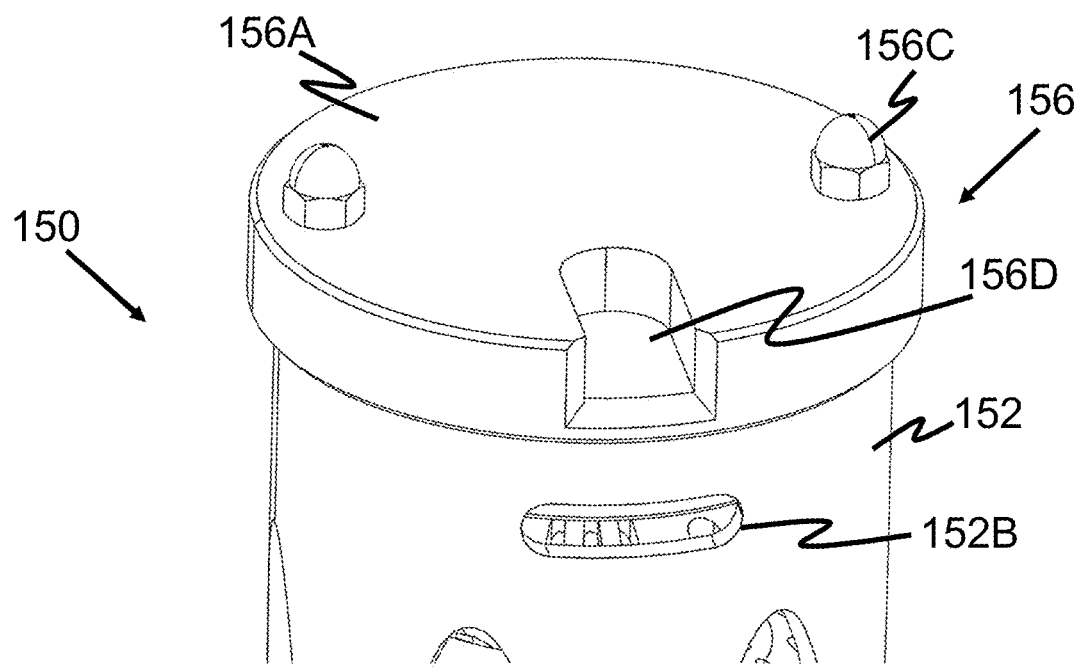
FIG. 21 is a top perspective view of a storage container for a plurality of portable sensor devices according to one embodiment of the present invention.
Figure 22:
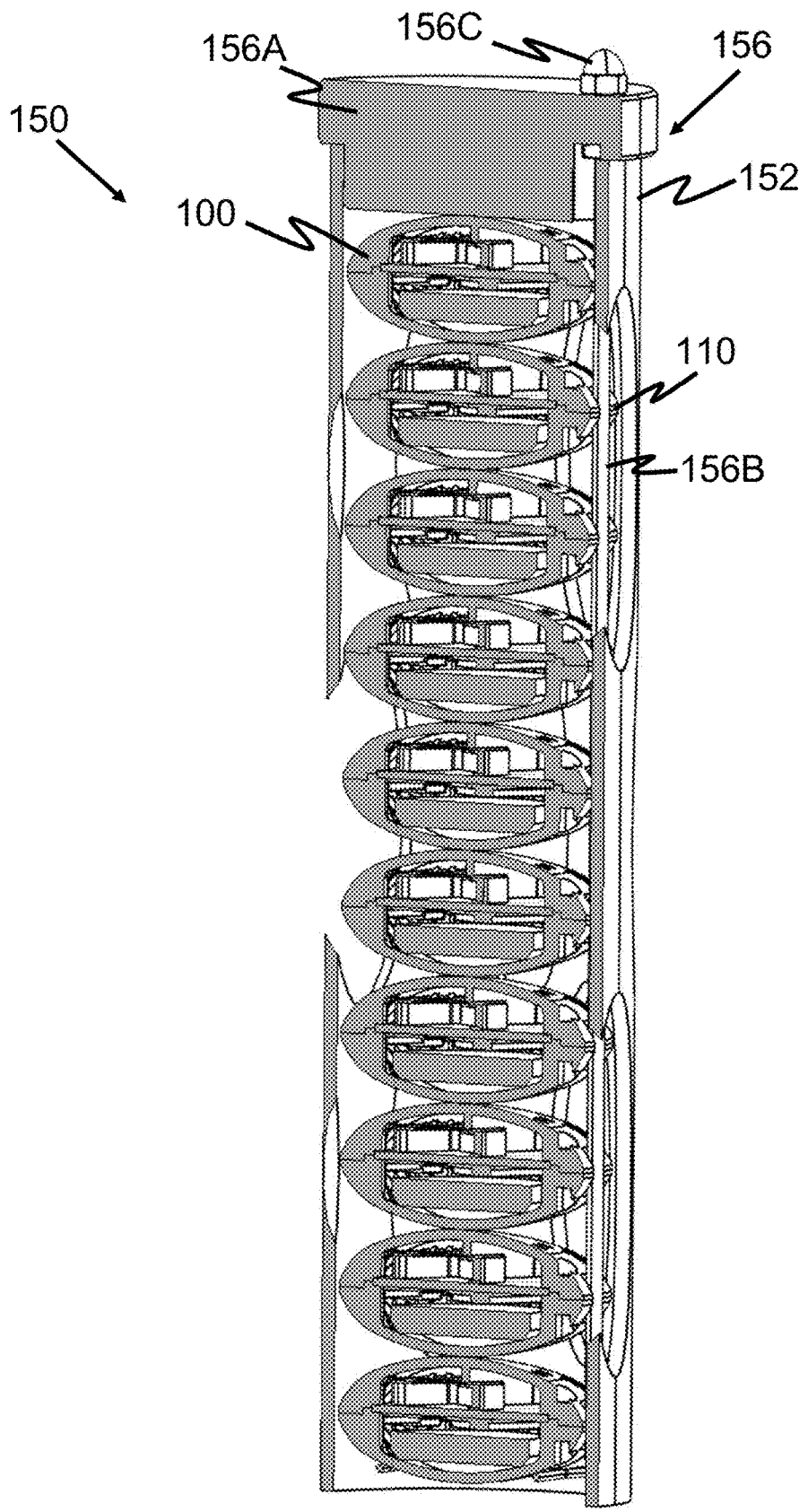
FIG. 22 is a cross sectional view of a storage container for a plurality of portable sensor devices according to one embodiment of the present invention.
Figure 23:
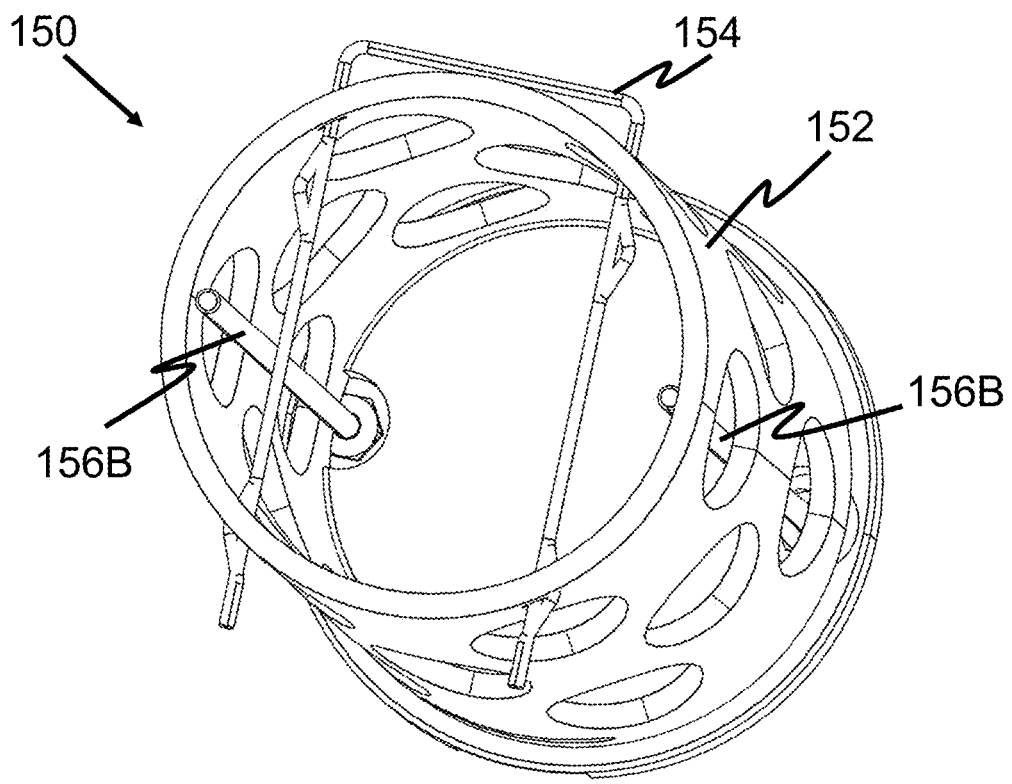
FIG. 23 is a bottom perspective view of a storage container for a plurality of portable sensor devices according to one embodiment of the present invention.
Figure 24:
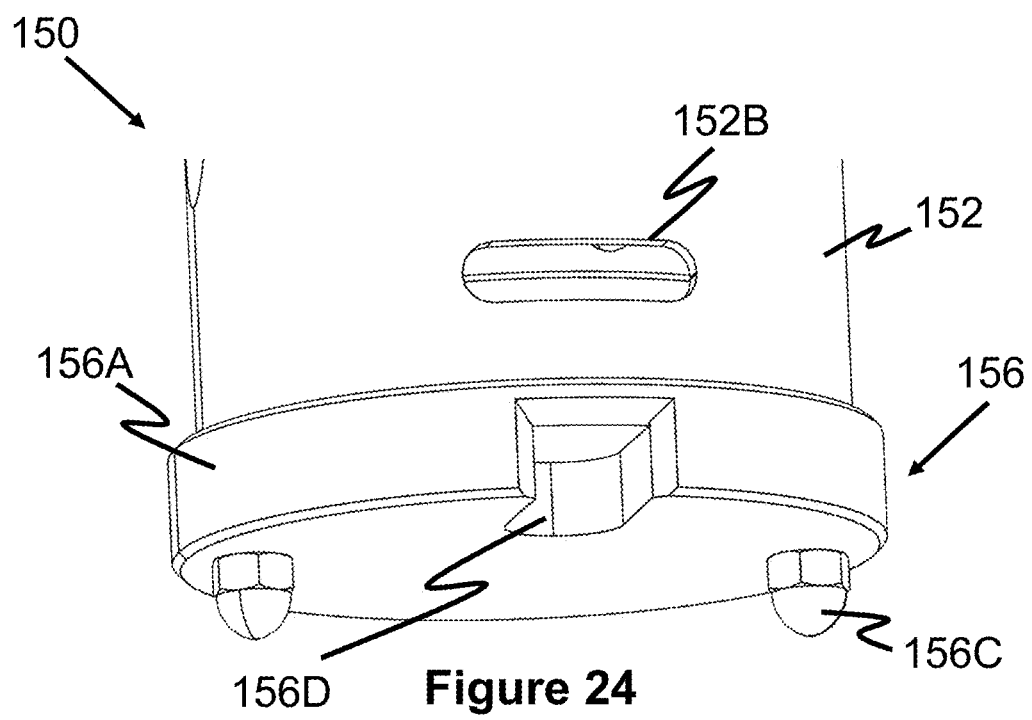
FIG. 24 is a top perspective view of a storage container for a plurality of portable sensor devices according to one embodiment of the present invention.

As seen best in FIGS. 17 and 20, the bottom end of the tube 152 includes a removable stop member 154 that prevents the sensor devices 100 from falling out of the bottom of the tube 152. When the tube 152 is connected to the deployment mechanism described later, the stop member 154 can be removed, allowing the sensor devices 100 to be removed from the tube 152 and deployed. Note that FIGS. 17 and 20 illustrate the tube 152 in an upside down position to clearly show the stop member 154, however this end with the stop member 154 is generally pointed downwards during use and when installed on the deployment mechanism, discussed later. In one embodiment, the stop member is a "C" shaped wire that two straight regions that each passthrough apposing apertures in the tube 152 as seen in FIG. 20. The straight portions may further include wider portions that act as detents to help the stop 154 remain locked in the tube 152.

The storage assembly 150 may further include a charging assembly 156 supplying one or more (and preferably all) of the sensor units 100 with power to charge their batteries 120. In one embodiment, the charging assembly 156 may include a cap portion 156A disposed on a top end of the tube 150. Two electrically conductive rods 156B are positioned on opposite sides within the tube 150 and are connected to the cap portion 156A. The top surface of the cap portion 156A includes two external electrodes which are in electrical communication with the conductive rods 156B. These electrodes can take the form of nuts 156C screwed on an end of the rods 156B (FIG. 21), can be exposed end portions of the rods 156B themselves, or a similar arrangement.

When the sensor devices 100 are placed into the tube 150, they are rotationally oriented so that their channels 110 (and hence their electrodes 110A or charging clips) are each engaged with or mate with one of the conductive rods 156B. Hence, when current is applied to the nuts 156C, it passes through the rods 156B, into the electrodes 110A, and into each of the batteries 120 of the sensor units. Alternatively, the charging contacts can be the top and bottom of the sensor device 100 so that adjacent sensor units 100 contact adjacent charging contacts, creating a large charging circuit and thereby eliminating the need for the conductive rods 156B.

It should be appreciated that the charging assembly 156 should provide consistent polarity on the conductive rods 156B (i.e., one rod should always have positive polarity and the other should always have negative polarity). In this regard, the cap 156A has a notch 156D that allows the cap 156A and the nuts 156C to only engage the charging structure (discussed below) in one orientation. This allows the charging assembly 156 to consistently engage the charging structure in the same position and orientation, and thereby receive positive and negative polarity current in a consistent manner.

Similarly, it may be desirable to include a feature within the tube 152 that allows the sensor devices 100 only one orientation in which they can slide into the tube 152 so that their positive and negative channels 110 consistently engage with corresponding positive and negative conductive rods 156B. For example, one rod 156B and one channel 110 may have a larger diameter or different shapes (e.g., circular and square diameter), thereby only allowing a single orientation for the sensor devices 100. Preferably, this orientation is also configured so that the top housing members 102 are oriented upward and the bottom housing members 104 are oriented downward.

Figure 25:
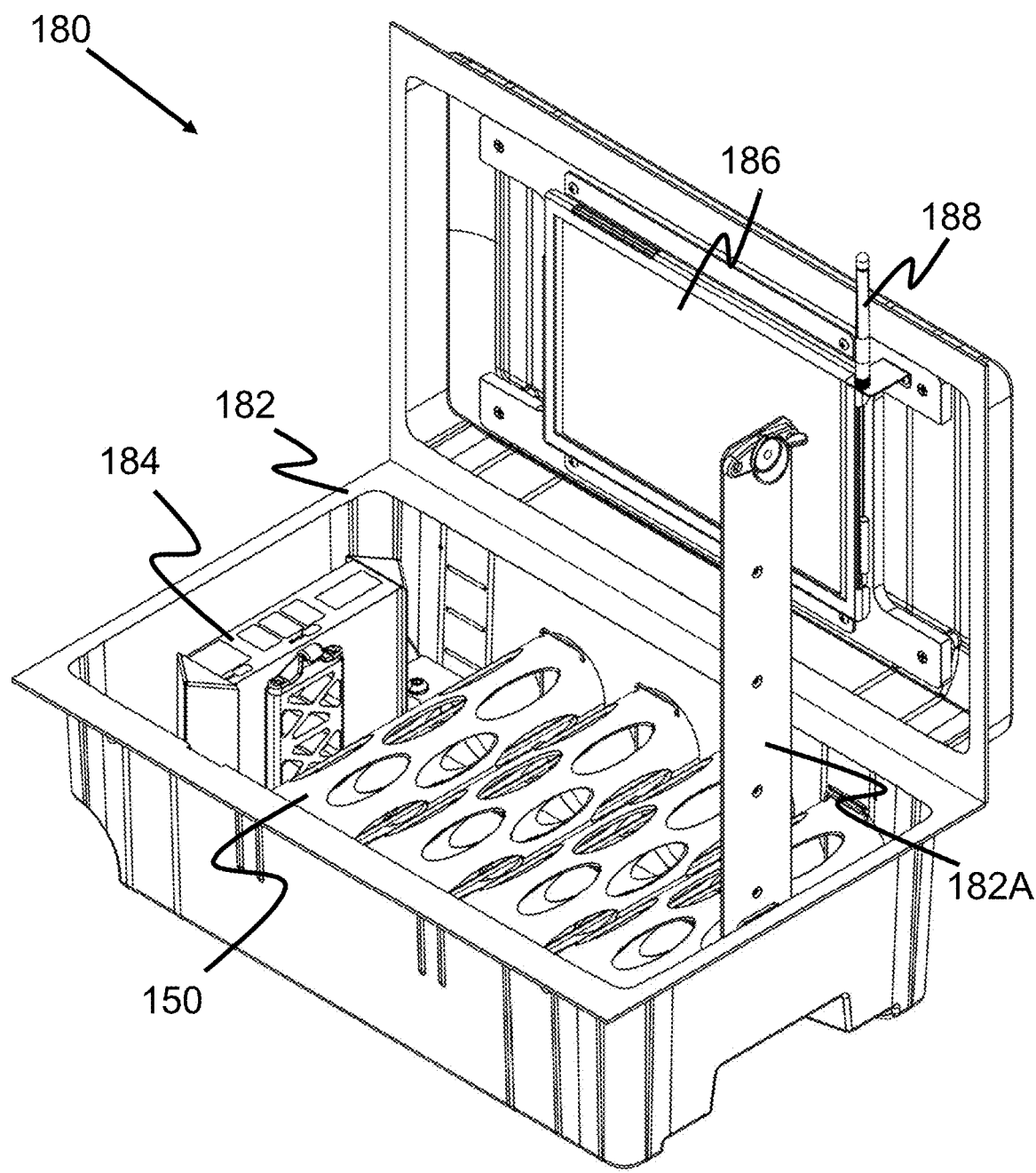
FIG. 25 is a top perspective view of a charging and control container for a plurality of portable sensor devices according to one embodiment of the present invention.
Figure 26:
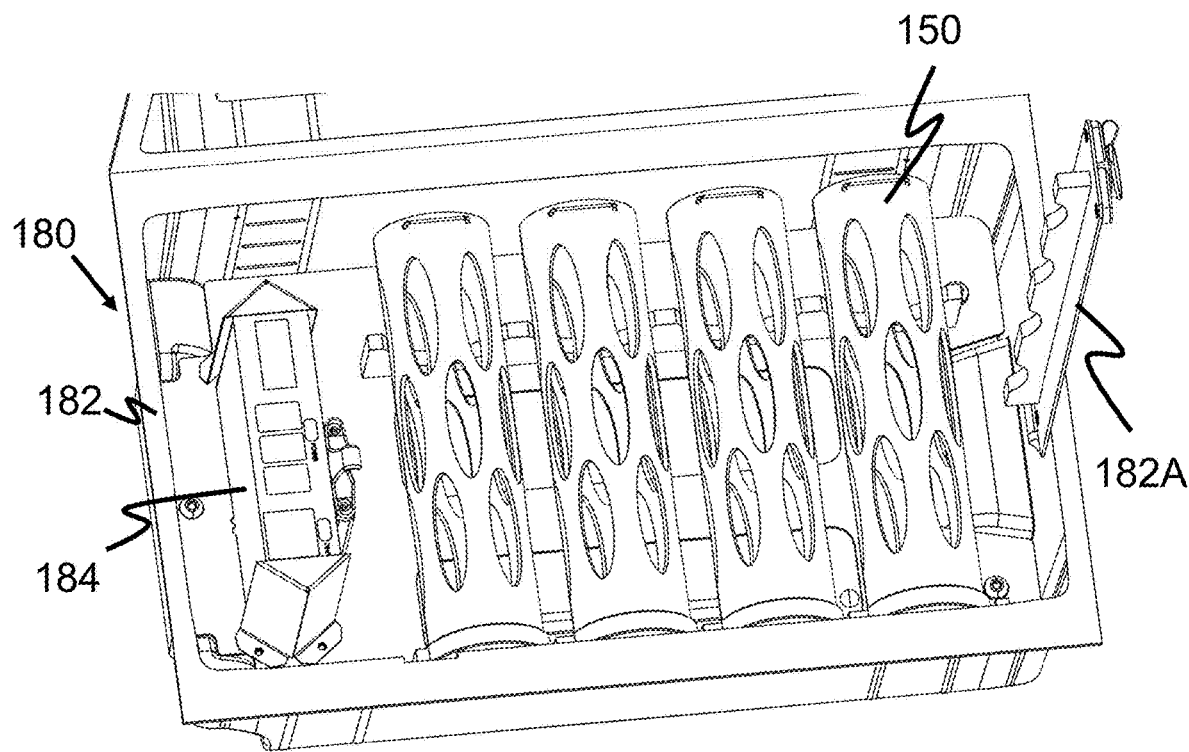
FIG. 26 is a top view of a charging and control container for a plurality of portable sensor devices according to one embodiment of the present invention.
Figure 27:
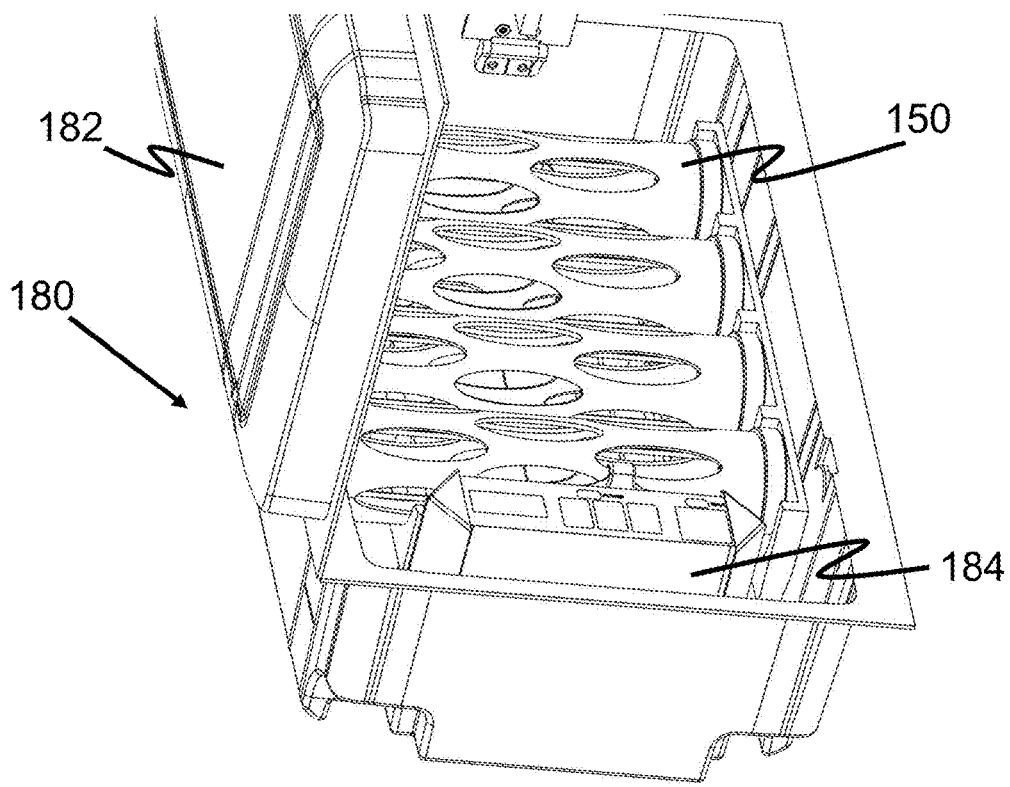
FIG. 27 is a top perspective view of a charging and control container for a plurality of portable sensor devices according to one embodiment of the present invention.

FIGS. 25-25 illustrate one embodiment of charging and control assembly 180 that can charge the batteries 120 of one or more sensor devices 100, as well as send and received data with the sensor devices 100. In this embodiment, the charging and control assembly 180 is located in a trunk, case, or portable housing 182 having a closable lid to facilitate its transport near a desired target area (e.g., battlefield). However, the charging and control assembly 180 may also be integrated into other housings or areas, such as being built into a vehicle. Additionally, it is possible for the data control components and the charging components to be in separate housings from each other (i.e., a dedicated control system and a dedicated charging system).

The assembly 180 may include a control system 184 comprising a small computer (e.g., processor, ram, storage drive, video output) and a charging circuit that controls and regulates charging to one or more storage assemblies 150. The computer (e.g., computer, tablet computing device, phone) can operate the display 186 that is fixed (or detachable) to the lid of the housing 182, as well as the wireless antenna 188 that is configured to send and received wireless signals with the plurality of sensor units 100 in either their deployed or non-deployed state. The computer includes software configured to operate a plurality of different sensor algorithms with incoming data from the sensor units 100, as will be discussed later in this specification.

Figure 29:
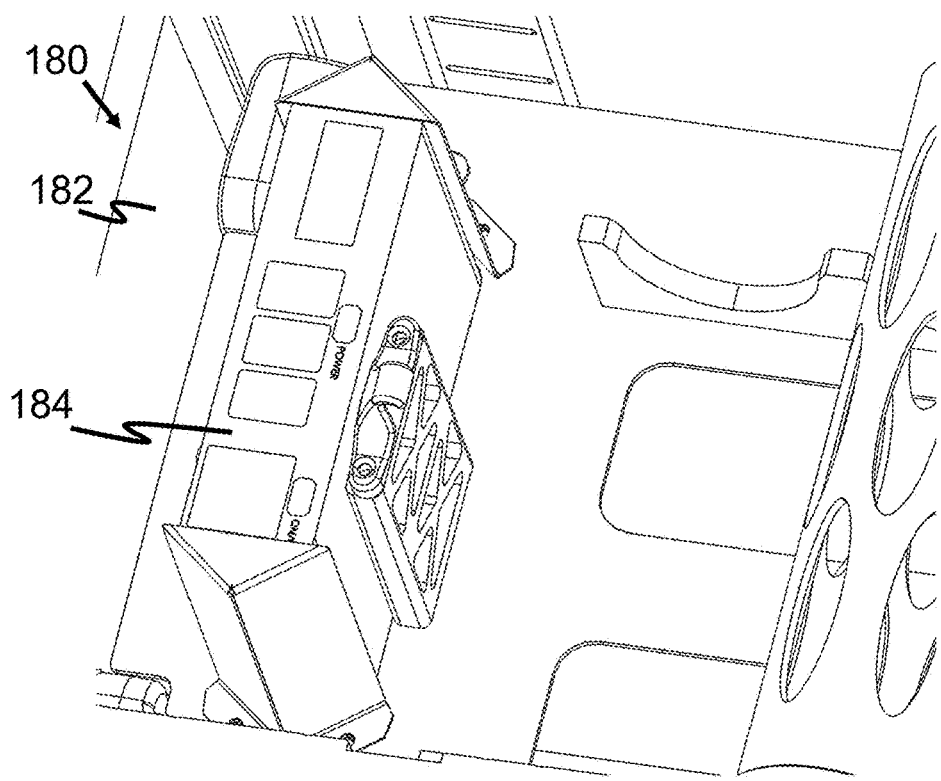
FIG. 29 is a view of a charging and control container for a plurality of portable sensor devices according to one embodiment of the present invention.
Figure 30:
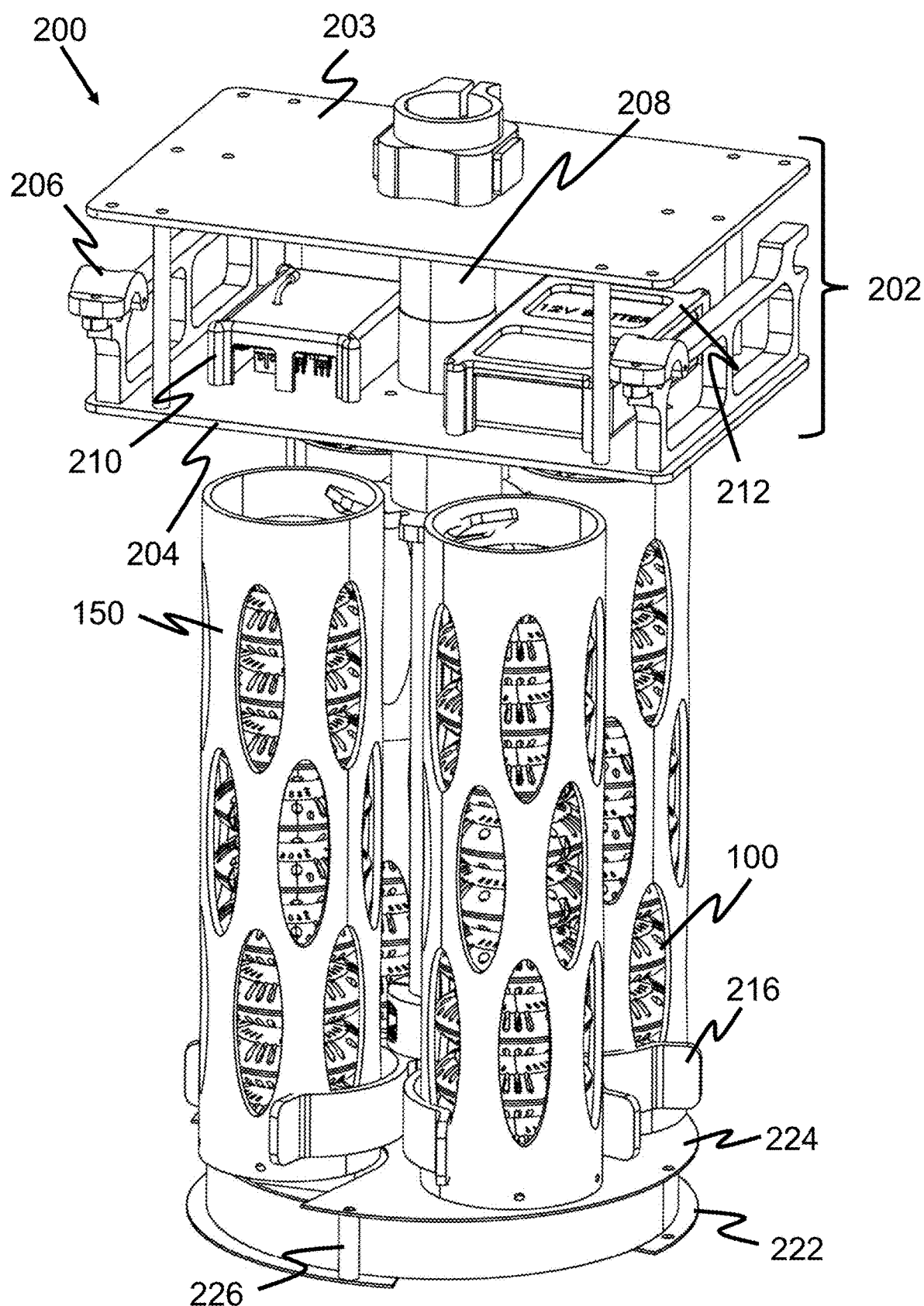
FIG. 30 is a view of a deployment assembly for a plurality of portable sensor devices according to one embodiment of the present invention.
Figure 31:
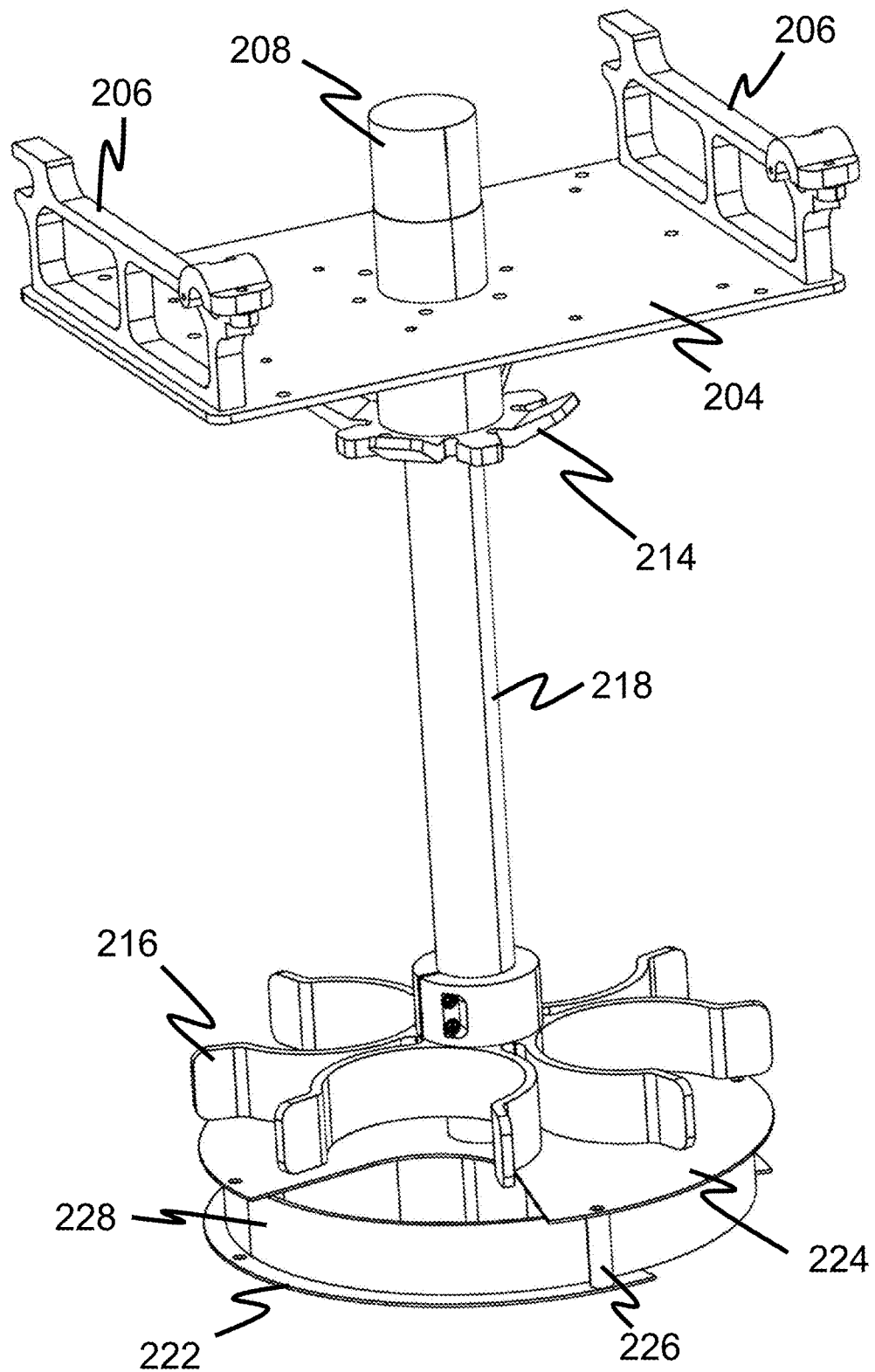
FIG. 31 is a view of a deployment assembly for a plurality of portable sensor devices according to one embodiment of the present invention.
Figure 32:
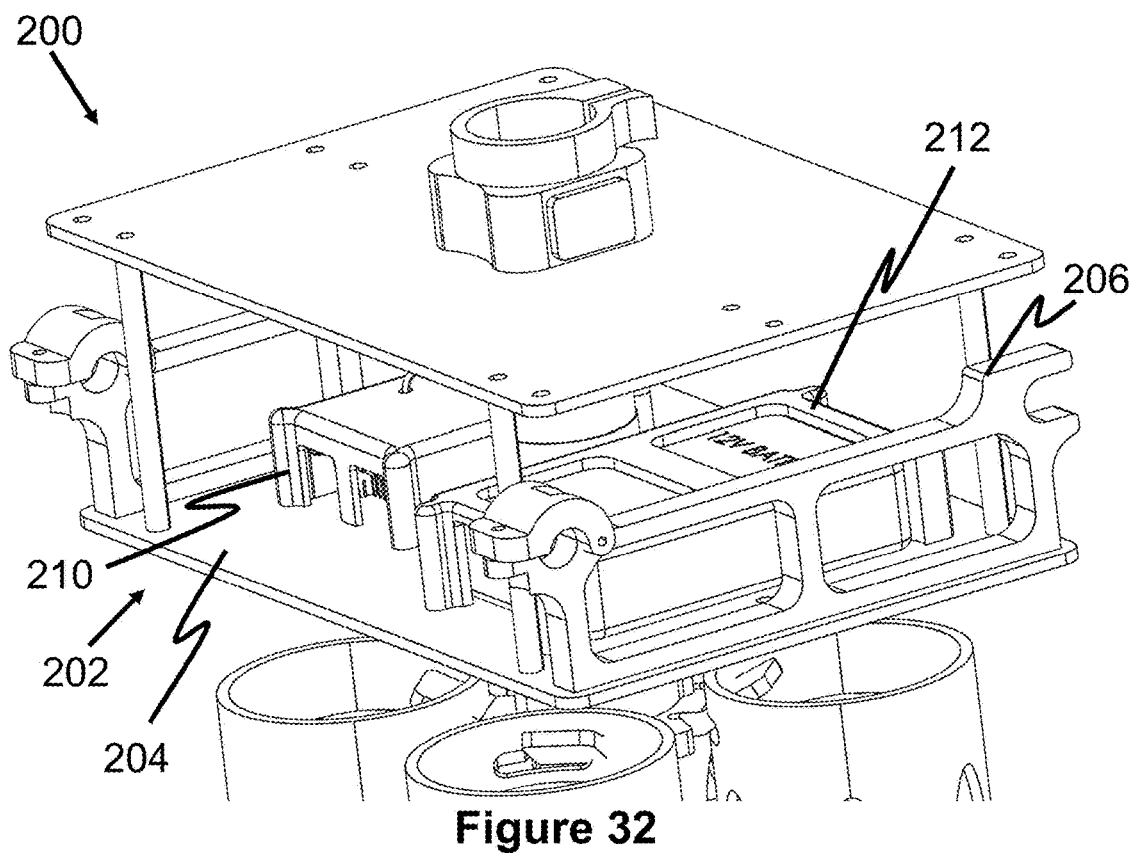
FIG. 32 is a view of a deployment assembly for a plurality of portable sensor devices according to one embodiment of the present invention.
Figure 33:
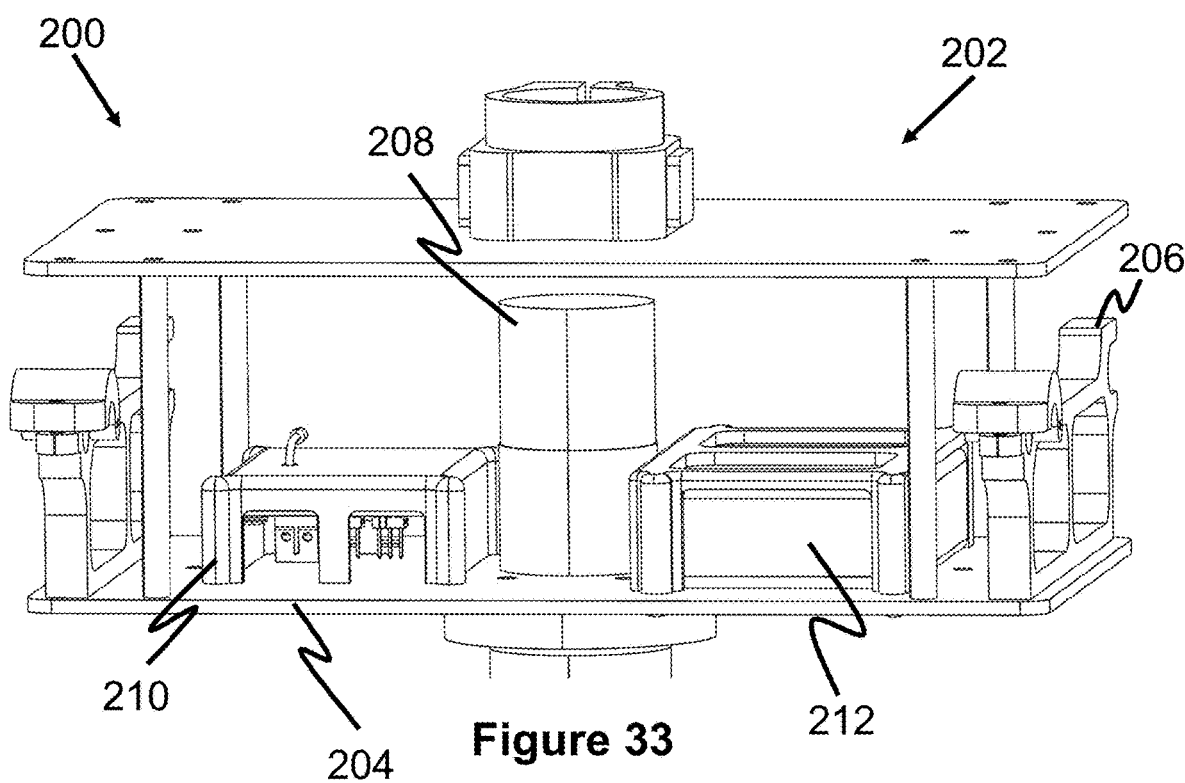
FIG. 33 is a view of a deployment assembly for a plurality of portable sensor devices according to one embodiment of the present invention.

In one embodiment, the housing 182 is configured to have portions of the case shaped to engage the plurality of storage assemblies 150 and maintain their position within the housing 182. For example, the housing 182 may include a plurality of curved portions (FIG. 29) shaped to engage the underside of the storage assemblies 150 and a movable top strap or bracket 182A that is positioned over the top side surfaces of the storage assemblies 150 and removably latch to another location in the housing 182. This prevents the storage assemblies 150 from moving around in the housing 182 during transport.

Figure 28:
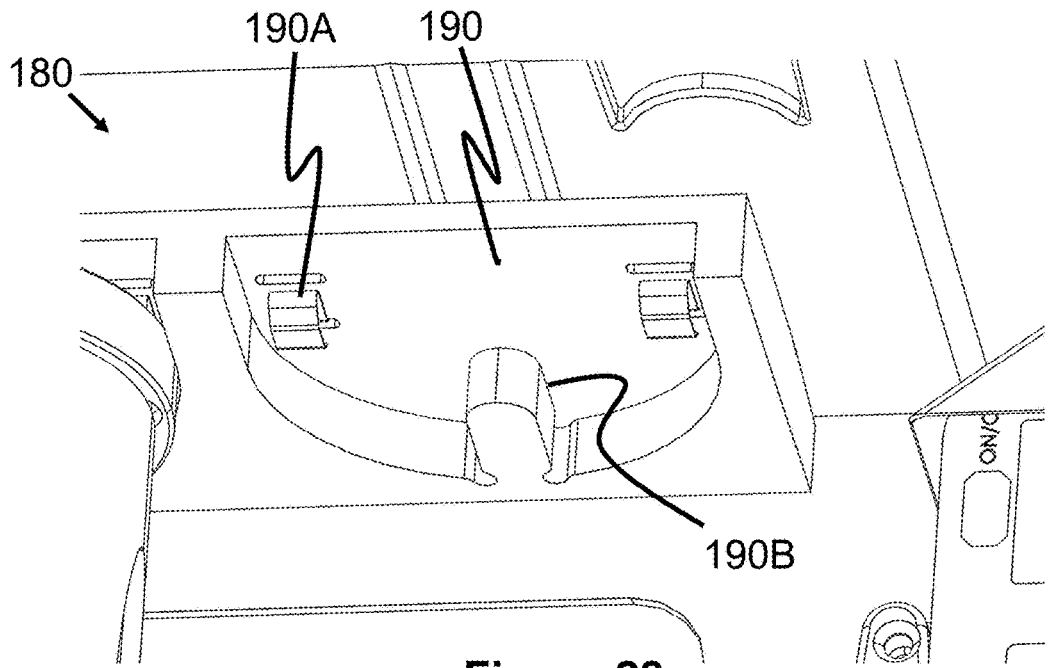
FIG. 28 is a view of a charging and control container for a plurality of portable sensor devices according to one embodiment of the present invention.

As seen best in FIG. 28, the housing 182 further includes a charging area 190 that is shaped and configured to engage the charging assembly 156 to charge the sensor devices 100. Specifically, the charging area 190 may include two electrodes 190A that are spaced and configured to contact the nuts 156C on the cap 156A. To ensure that the correct polarity current is delivered to each nut 156C, the charging area 190 includes a raised feature that is sized and shaped to mate with notch 156D on the cap 156A. This ensures that the electrodes 190A can be contacted by the nuts 156C in only one rotational orientation. However, it should be understood that other shapes and methods of enforcing a specific rotational position are also possible.

Figure 44:
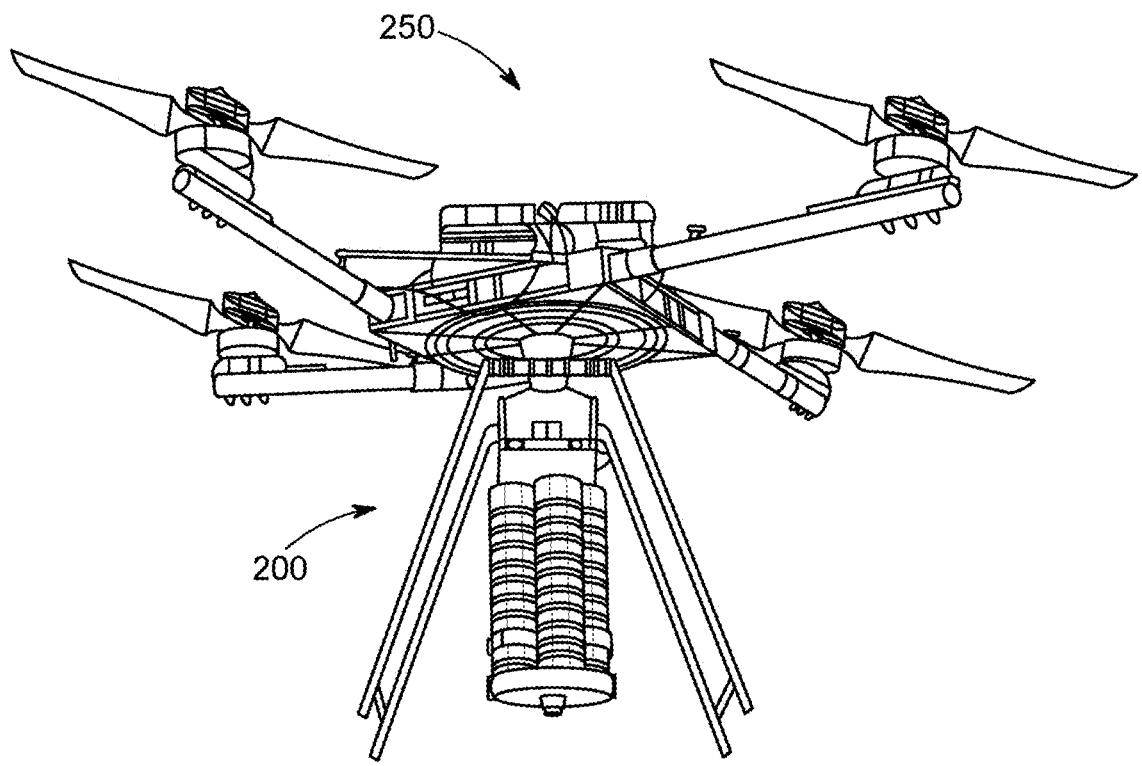
FIG. 44 is a view of an unmanned arial vehicle attached to a deployment assembly according to one embodiment of the present invention.
Figure 45:
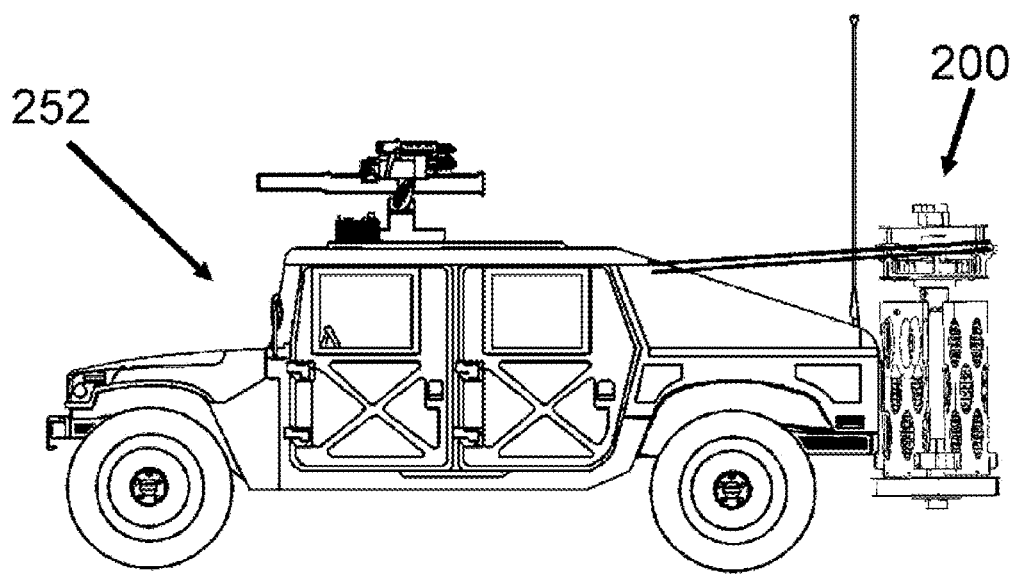
FIG. 45 is a view of ground vehicle attached to a deployment assembly according to one embodiment of the present invention.

FIGS. 30-42 illustrate various aspects of a deployment assembly 200 for the sensor devices 100. In one embodiment, the deployment assembly 200 is composed of lightweight materials such as a carbon fiber composite. The present embodiment of the deployment assembly 200 may be particularly suitable for arial vehicles such as unmanned arial vehicles (UAVs) 250 (FIG. 44) but may also be connected to a wide variety of ground vehicles 252 (FIG. 45). In this respect, the vehicles 250, 252 can move to a desired target area or perimeter fence around an area and then drop one or more sensor devices 100 within the target area or along a line of interest. The deployment of sensor device 100 is not limited to assembly 200 but can also be deployed by hand (e.g., throwing), emplaced in PPE, within the exterior/interior of vehicles, tents and temporary installations or buildings.

Figure 34:
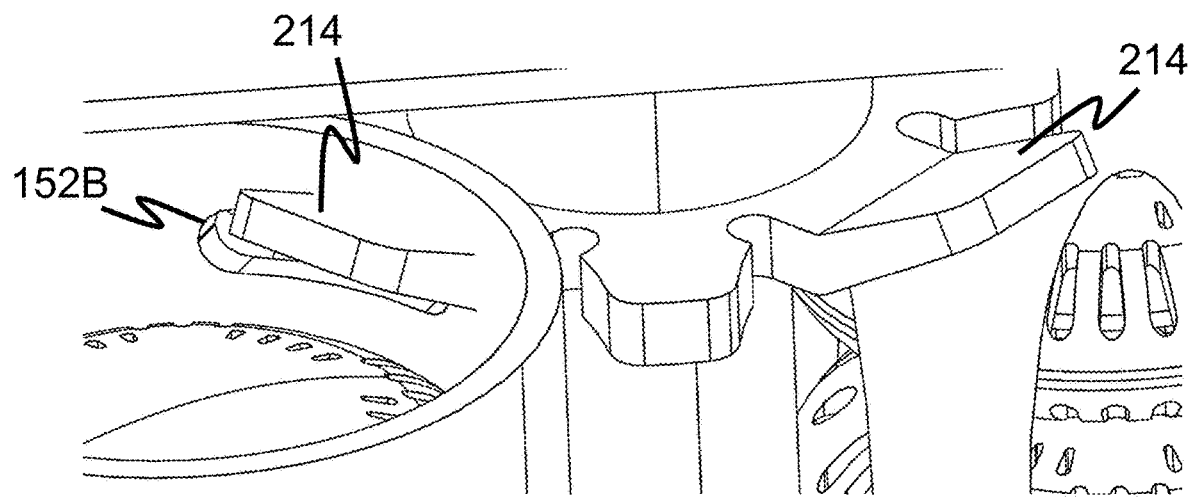
FIG. 34 is a view of a deployment assembly for a plurality of portable sensor devices according to one embodiment of the present invention.
Figure 35:
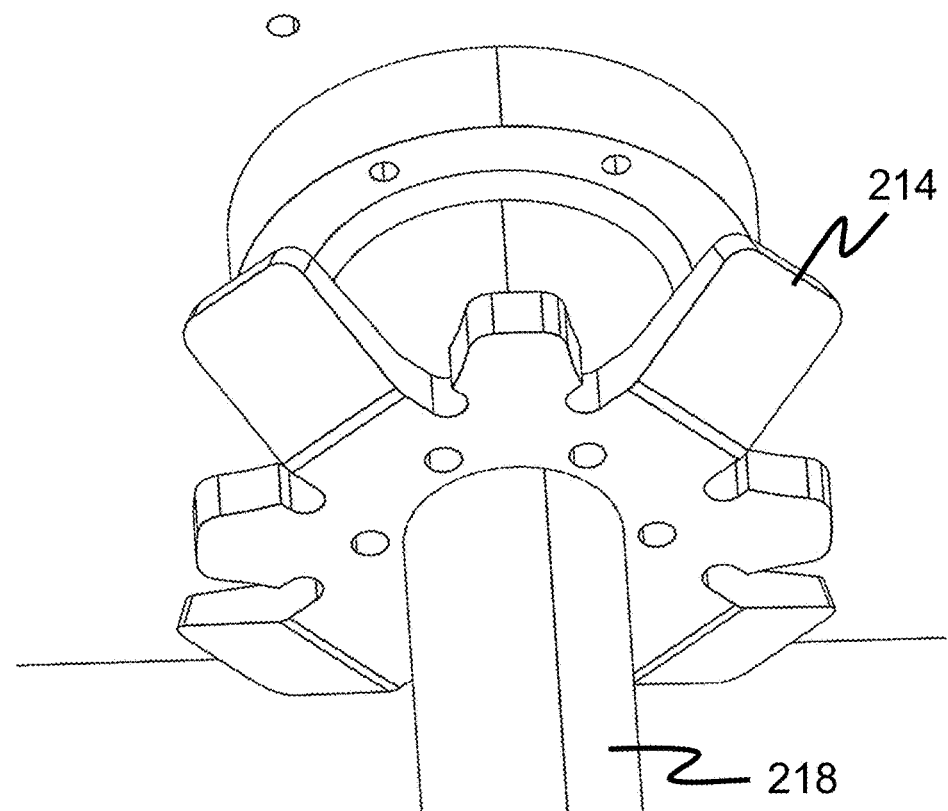
FIG. 35 is a view of a deployment assembly for a plurality of portable sensor devices according to one embodiment of the present invention.
Figure 36:
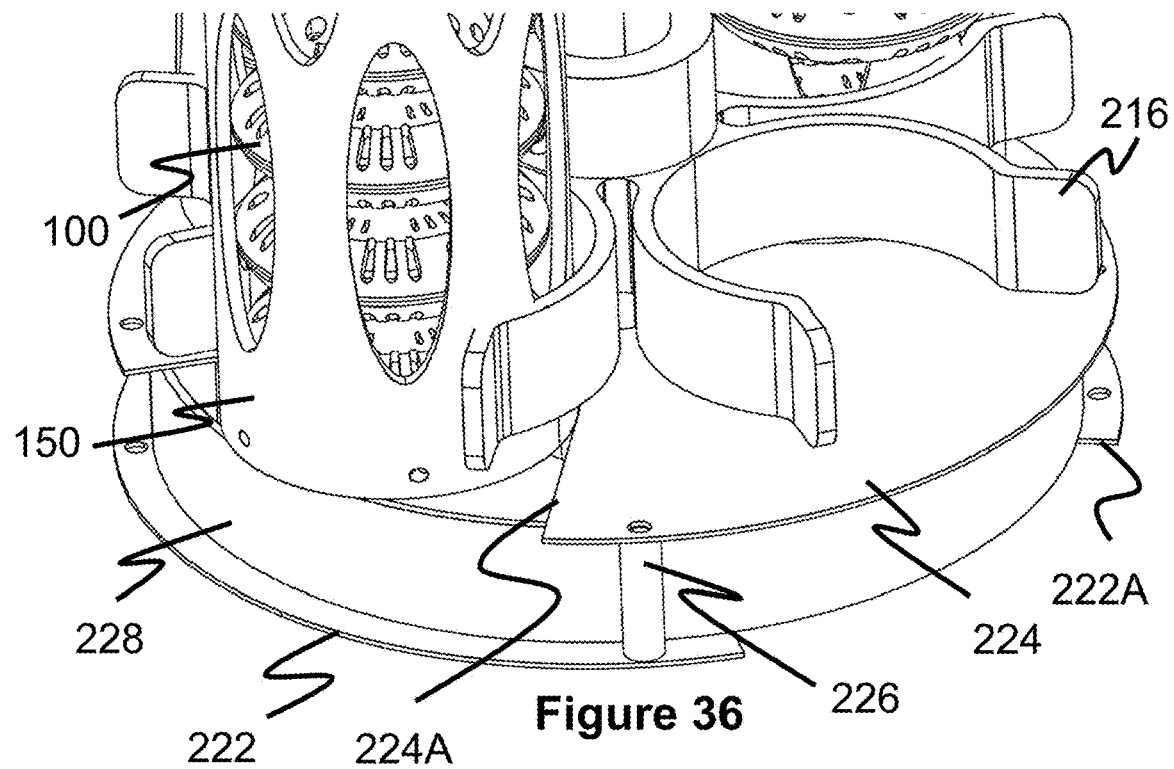
FIG. 36 is a view of a deployment assembly for a plurality of portable sensor devices according to one embodiment of the present invention.
Figure 37:
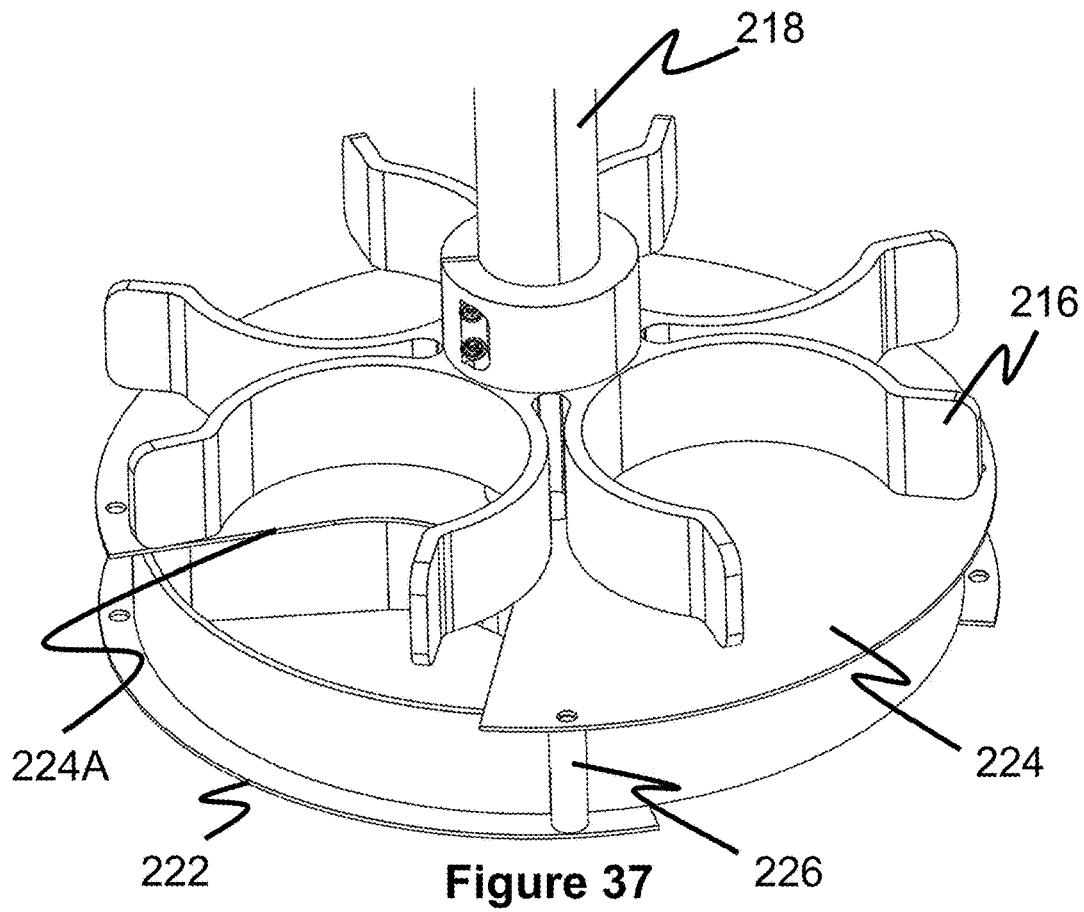
FIG. 37 is a view of a deployment assembly for a plurality of portable sensor devices according to one embodiment of the present invention.
Figure 38:
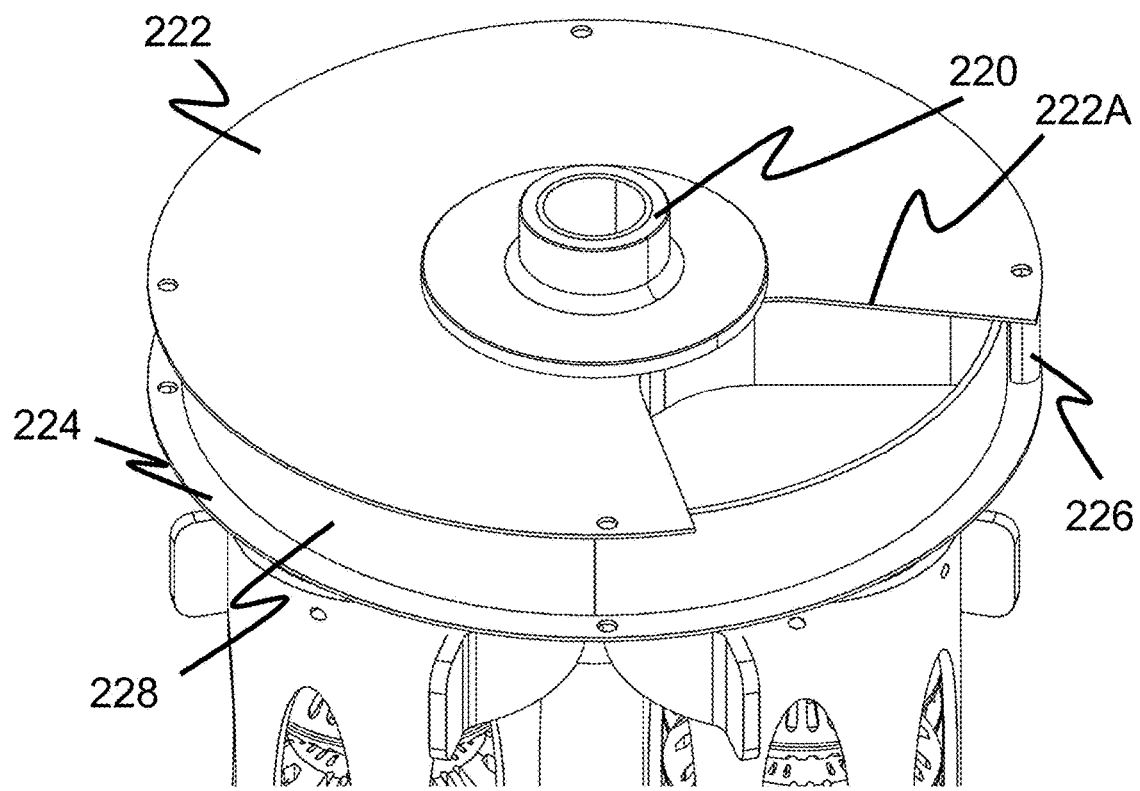
FIG. 38 is a view of a deployment assembly for a plurality of portable sensor devices according to one embodiment of the present invention.

To load the storage assemblies 150 on to the deployment assembly 200, a horizontal slot 1526 at the top of the tube 152 is moved over one of a plurality of flat hooks 214 located at an upper area of the deployment assembly 200 (FIGS. 34 and 35). A bottom portion of the storage assembly 150 is engaged by a "C" shaped bracket 216 (FIGS. 36 and 37) to help minimize any movement of the storage assemblies 150 during transit or deployment. In order to help reduce weight, the charging assembly 156 (including the cap 156A and rods 156B) can be removed from storage assembly 150 prior to installation on the deployment assembly 200. After the storage assembly 150 has been installed, the user can remove the removable stop member 154 from the bottom end of the tube 152, which then allows the sensor units 100 to be deployed by the deployment assembly 200.

Figure 39:
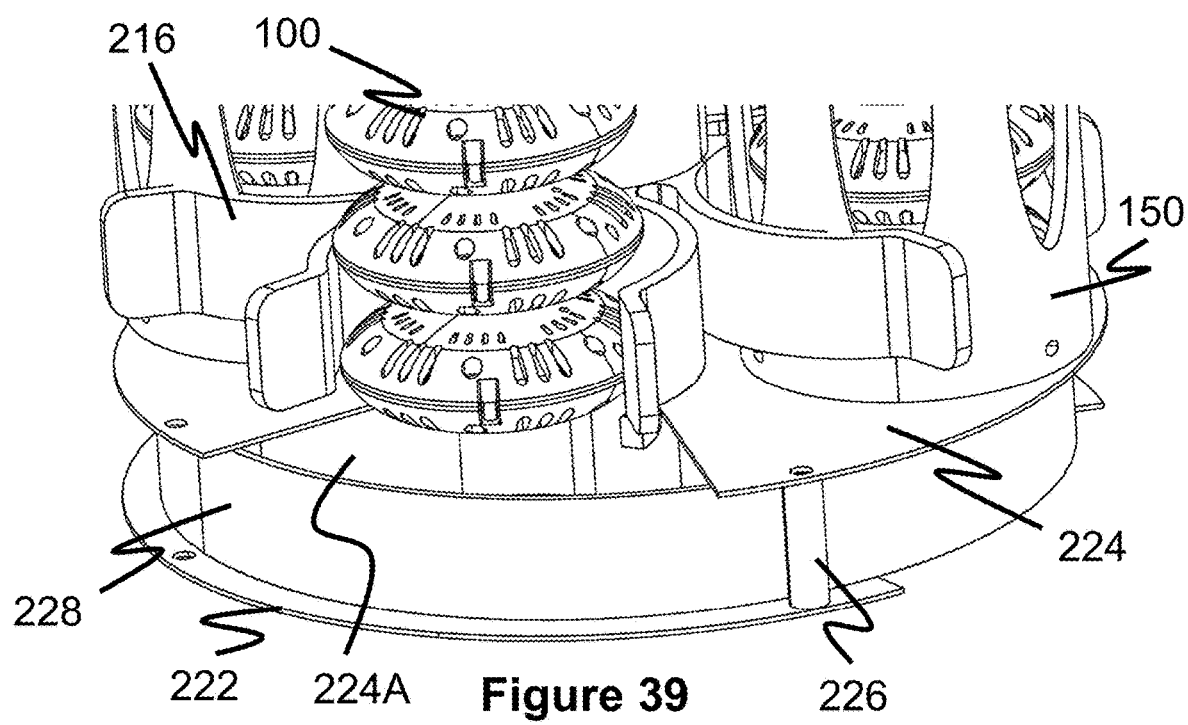
FIG. 39 is a view of a deployment assembly for a plurality of portable sensor devices according to one embodiment of the present invention.
Figure 40:
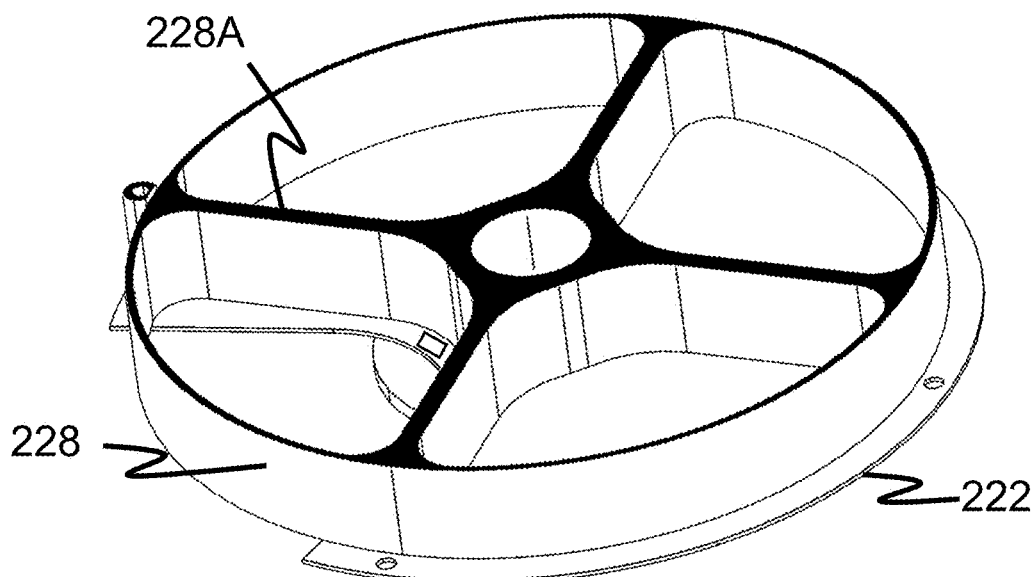
FIG. 40 is a view of a deployment assembly for a plurality of portable sensor devices according to one embodiment of the present invention.

As best seen in FIGS. 36-42, the bottom portion of the deployment assembly 200 includes a circular upper plate 224 and a circular lower plate 222, both of which are fixed or connected to each other via posts 226 to that both plates 222, 224 rotate in unison with each other. The upper plate 224 and lower plate 224 are positioned on the top and bottom, respectively, of a circular divider 228 (FIG. 40). The divider has a plurality of walls 228A including a circular outer wall and several radial walls, that form several compartments with plates 222, 224.

The top plate 224 further includes a top opening 224A which is sized to expose all of or at least a portion of one of the compartments formed by the circular divider 228. Similarly, the bottom plate 222 includes a bottom opening 222A which is sized to expose all of or at least a portion of one of the compartments formed by the circular divider 228. Preferably, the top opening 224A is radially offset from the bottom opening 222A so that only one of these openings is positioned over/under one of the compartments at any time. Put another way, both openings 222A, 224A are not positioned directly above/below each other. In one embodiment, the openings 222A, 224A are positioned to uncover laterally adjacent compartments, however, the openings 122A, 224A can be placed at any locations as long as they do not directly overlap each other.

The top and bottom plates 222, 224 are configured to rotate in unison relative to the storage assemblies 150 above them while the divider 228 is configured to remain in place with no rotation. As seen in FIG. 39 (shown without the tube 152 for clarity), when the top opening 224A is move underneath one of the storage assemblies 150, one of the sensor devices 100 falls into the compartment below. Preferably, the divider 228 has a height that is only slightly larger than that of the sensor device 100, allowing only one to fall into a compartment at a time. As the top and bottom plates 222, 224 are rotated, the top opening 224A moves underneath another storage assembly 150, allowing another sensor device 100 to fall into an adjacent compartment. Once the bottom opening 122A rotates underneath a compartment containing a sensor device 100, the sensor device 100 is released, dropping downward.

Figure 41:
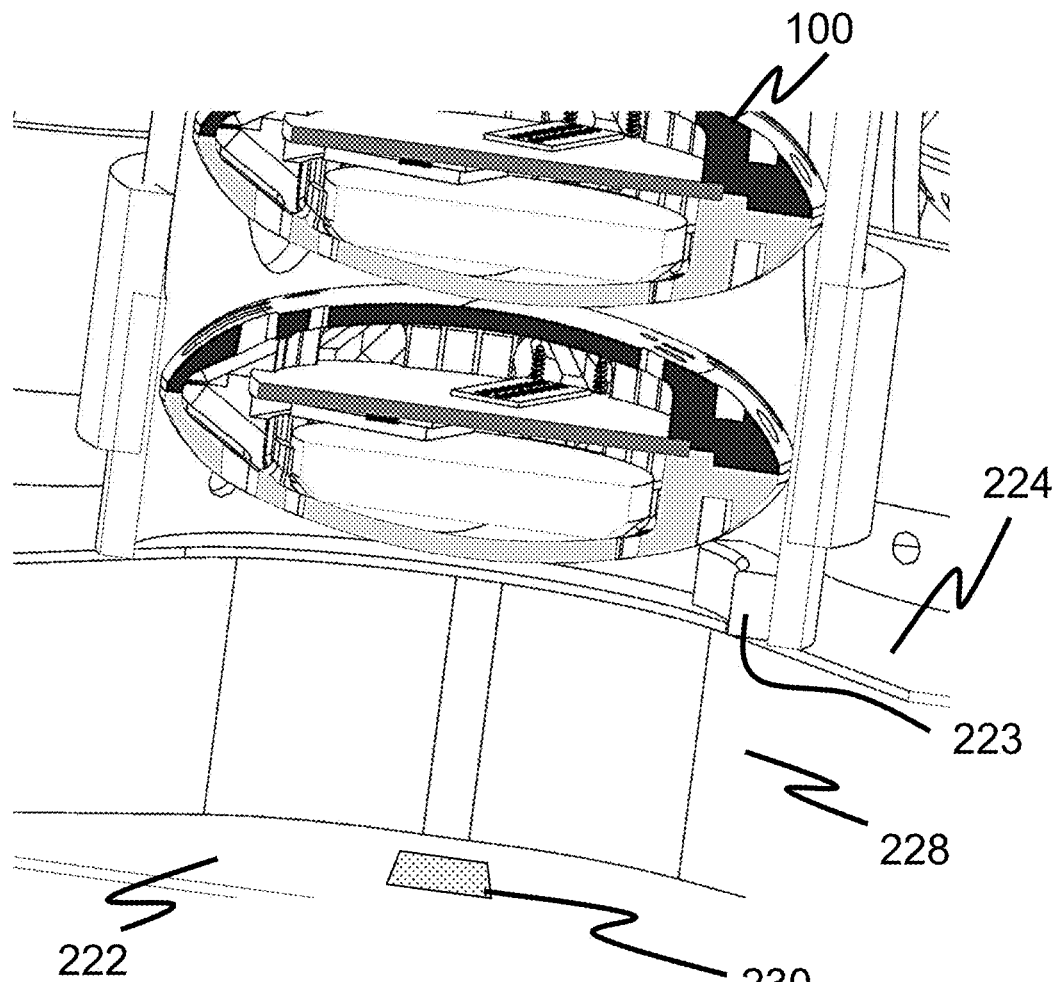
FIG. 41 is a view of a deployment assembly for a plurality of portable sensor devices according to one embodiment of the present invention.

As seen in FIGS. 20 and 41, the tube 152 can include a raised lip or block 223 near its bottom opening. This block 223 extends radially inward only a short distance (e.g., 0.5 inch) so as to "catch" an edge of the sensor device 100 and allow it to pass through the top opening 224A at a slight angle and not completely flat. This angled entry may better prevent the sensor device 100 from become stuck or wedged, especially in the case of accumulation of dirt, snow, ice, or similar elements.

A sensor system can further be used to monitor the position of the top and bottom plates 222, 224. For example, a Hall effect sensor or a mechanical switch can be used to monitor magnets or other physical features on the top and bottom plates 222, 224.

Figure 42:
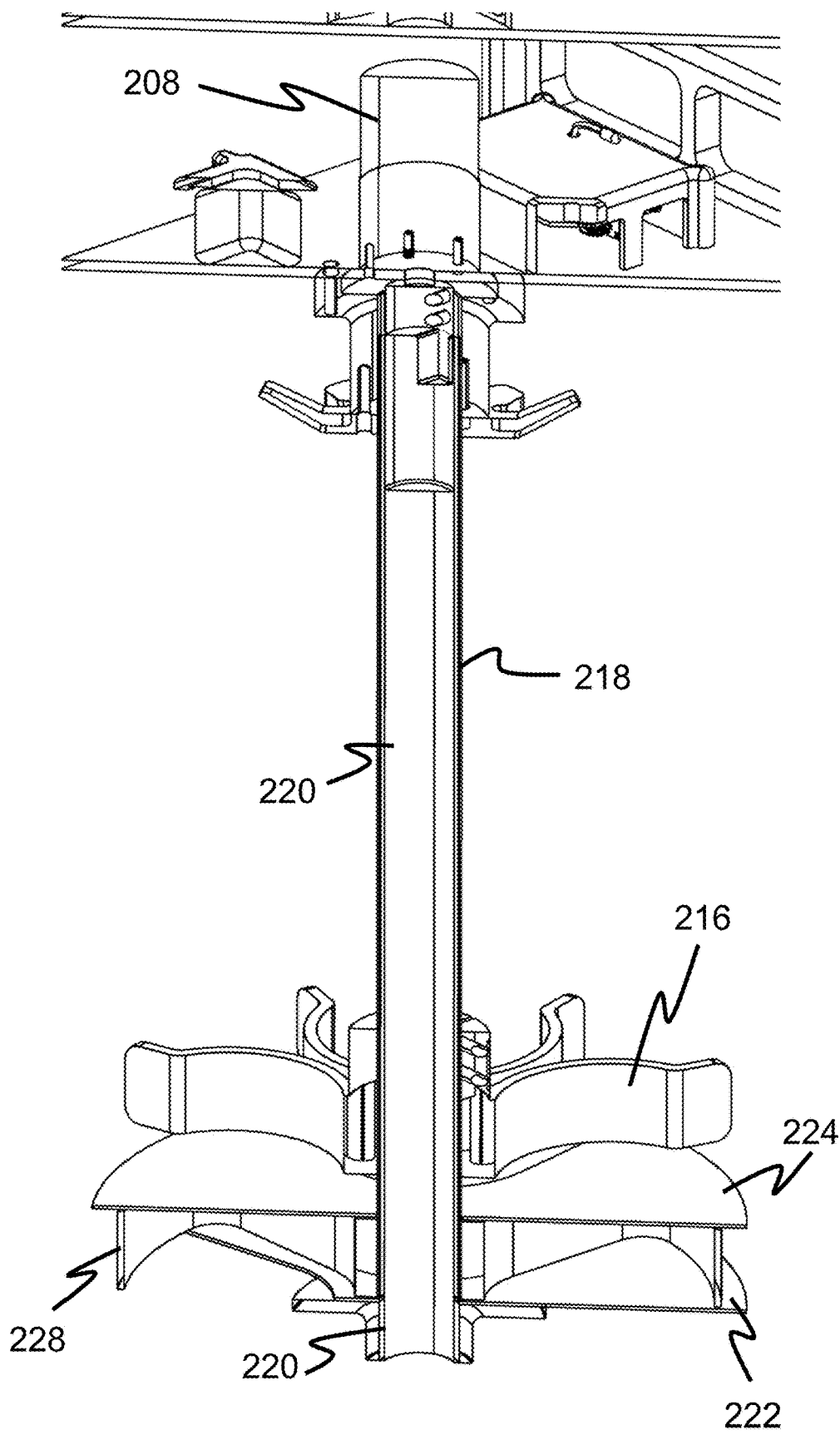
FIG. 42 is a view of a deployment assembly for a plurality of portable sensor devices according to one embodiment of the present invention.

As seen best seen in FIG. 42, the movement of the plates 222, 224 can be actuated by a motor 208 located in an upper portion 202 of the deployment assembly 200. The motor is connected to an inner rotating shaft 220 that is positioned within an outer stationary sleeve 218. The lower end of the shaft is connected to the lower plate 222, which causes the lower plate 222 and the attached upper plate 224 to rotate. The divider 228 can be attached to the non-rotating outer sleeve 218, so that it is prevented from rotation relative to the other components.

The upper portion 202 of the deployment assembly 200 can include upper and lower plates 203, 204 that are attached to each other and support additional components. Alternately, the upper portion 202 may comprise a fully or partially enclosed housing. In one embodiment, the upper portion 202 includes mounting brackets 206 on each side that can be configured to connect to portions of a vehicle (e.g., a UAV).

The upper portion also may include a controller 210 that is powered by a battery 212, and which powers and controls the motor 208 and position sensor (e.g., Hall effect sensor). The controller 210 may be a computer or similar processing device (e.g., processor, storage device, and software) that has a wireless transceiver and antenna for communicating with both the sensor devices 100 and the charging and control assembly 180. The controller 210 also monitors the position of the openings 122A, 124B via the Hall effect sensor so that it is aware of which storage assemblies 150 it is deploying sensor devices 100 from. Additional sensors can be used to alert the controller 210 as to how many storage assemblies 150 are present on the deployment assembly 200 and how many sensor devices 100 are in each storage assembly 150.

In this respect, the controller 210 can deploy individual sensor devices 100 when it receives instructions to do so from the charging and control assembly 180. Alternately, the controller 210 may include a GPS chip configured to provide it location information. In this manner, a user may send one or more coordinates (e.g., latitude and longitude) to the controller 210 which then deploys a sensor device 100 at each of the locations when the vehicle (e.g., UAV) reaches or draws near to each of the predetermined coordinates.

Further to this point, in the case of an arial vehicle, the controller 210 may transmit the coordinates for a specific target site to a specific sensor unit 100. If the sensor unit 100 includes its own GPS chip and mechanism for in-flight movement (e.g., movable fins), the sensor unit 100 can help guide itself to its predetermined coordinates.

If GPS chips are not included in the sensor devices 100 (e.g., to maintain lower manufacturing costs), other systems can be used to track the locations of individual sensor devices 100. For example, each sensor device may include an RFID sensor tag (e.g., on the circuit board or disposed on an interior or exterior of the housing) with a unique identification registered with the charging and control assembly 180 and/or controller 210 at drop. An RFID sensor 230 (FIG. 41) can be positioned at a location to sense or register the RFID sensor tag from a sensor device 100 that is about to be released. For example, the RFID sensor 230 may be located on the bottom plate 222. When the sensor tag is sensed by the RFID sensor 230 (which is connected to the controller 210, the controller 210 uses its own GPS chip to determine the location of the entire deployment assembly 200 and stores that data with the RFID from the RFID tag. This information can be transmitted to the charging and control system 180, providing an estimated location of the individual sensor device 100.

Figure 46:
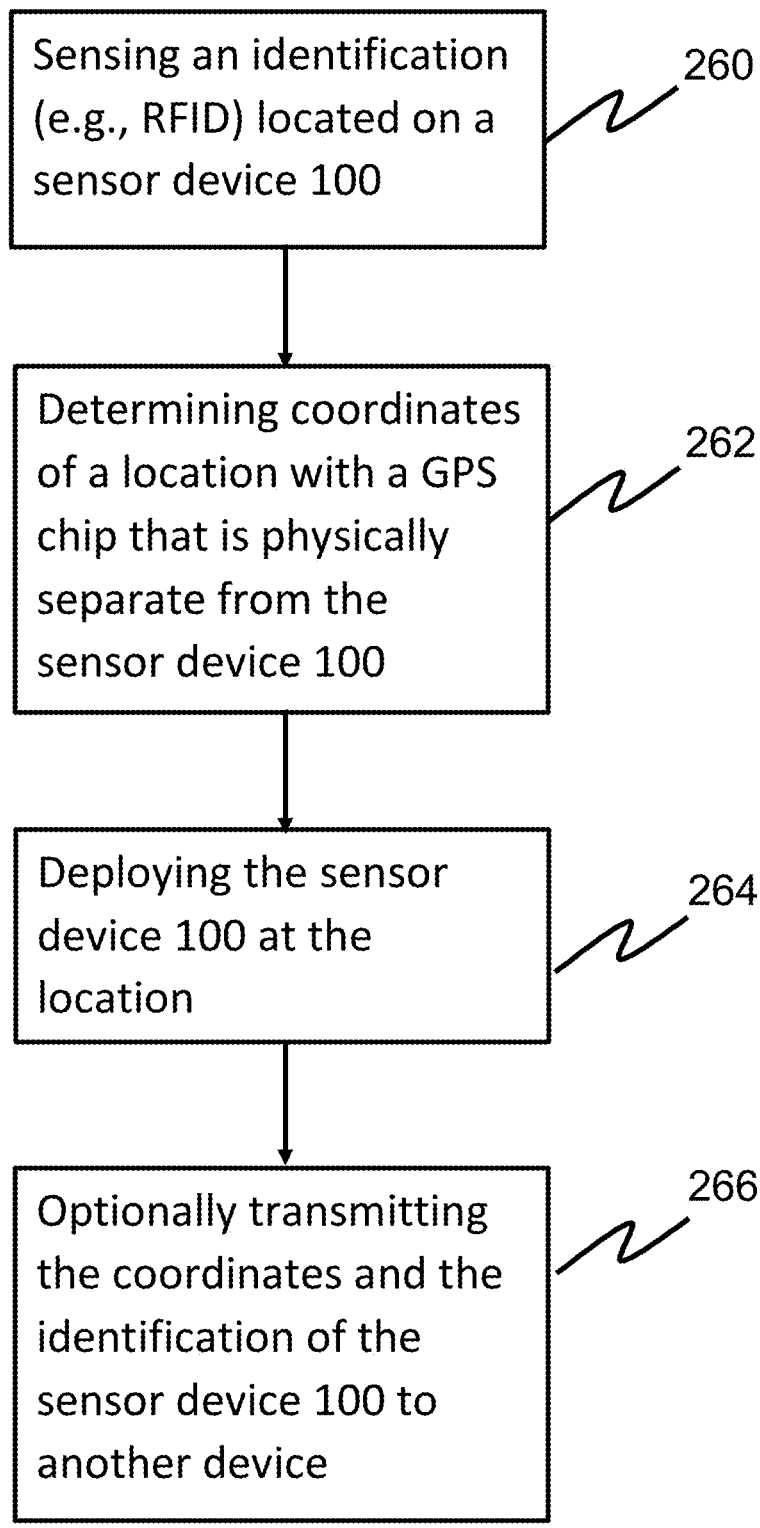
FIG. 46 is method of recording a position of a sensor at deployment according to one embodiment of the present invention.

In that respect, the present invention also includes a method of tracking a location of a sensor, shown in FIG. 46, which includes sensing an identification (e.g., RFID) located on a sensor device 100 (step 260), determining coordinates of a location with a GPS chip that is physically separate from the sensor device 100, such as in a controller 210 (step 262), deploying the sensor device 100 at the location (step 264), and then optionally transmitting the coordinates and the identification of the sensor device 100 to another device (step 266), such as the charging and control assembly 180.

Figure 43:
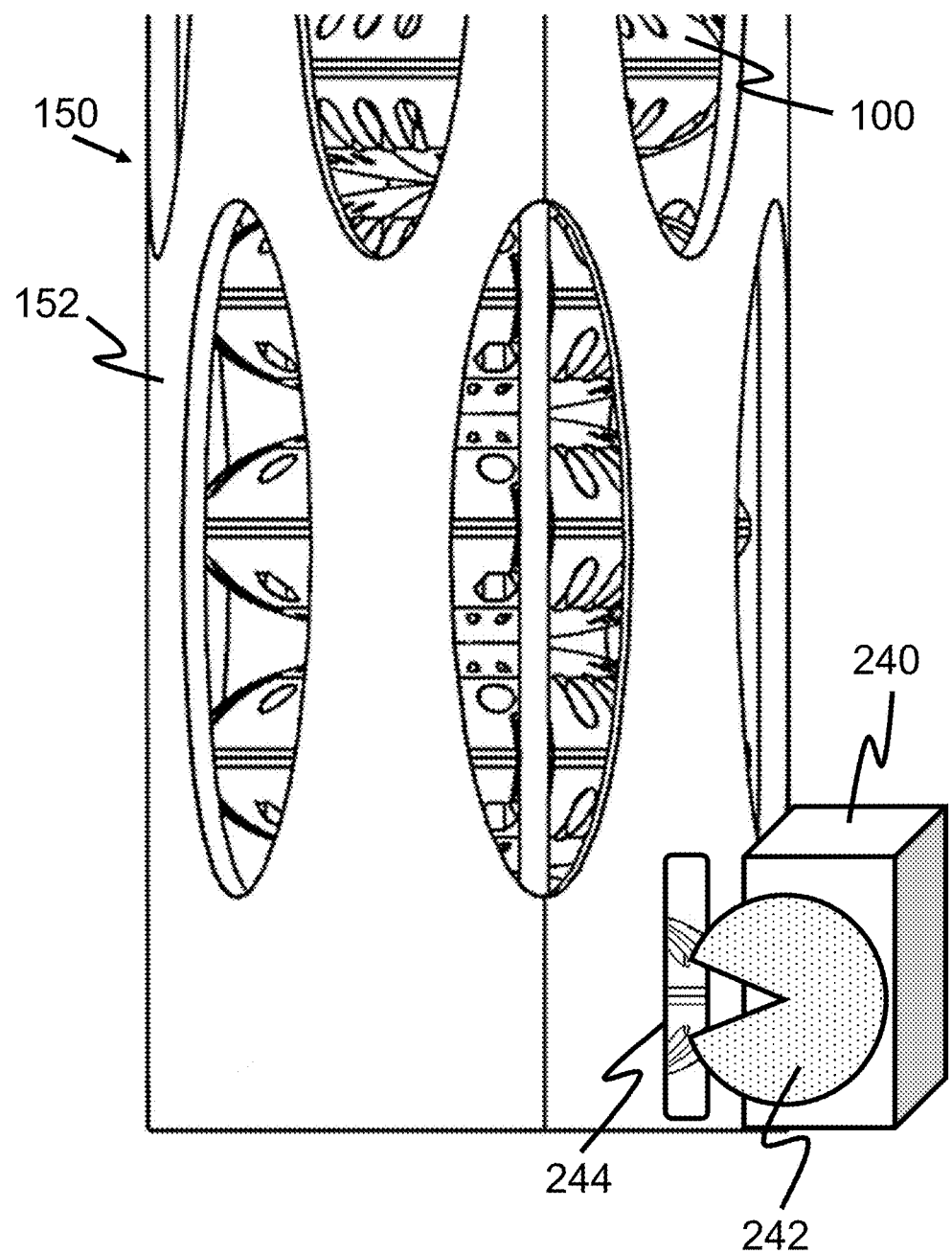
FIG. 43 is a view of a deployment assembly for a plurality of portable sensor devices according to one embodiment of the present invention.

Other deployment mechanisms are also possible according to the present invention. For example, each storage assembly 150 may be connected to a deployment mechanism on each of the storage assemblies 150 that are connected. For example, FIG. 43 illustrates a motor 240 that rotates a disc 242 that has a notch cut into it. The notch is positioned through an aperture or opening 244 in the tube 152 so that it engages a side of the sensor device 100. The disc 242 is rotated to move its notch downward which causes the sensor device 100 to fall. The disc 242 can be quickly moved back upward to engage the next sensor device 100, preventing it from also falling until being actuated by the user. The notch is further refined to match the shape of the sensor device 100 so as to provide better engagement.

The sensor device 100 has the capability of identify specific threats and can include algorithms that are configured to provide unique functionality based on the data received from a plurality of deployed sensor units 100. These algorithms can be executed on any one of the controllers or control systems described in this specification (e.g., the charging and control assembly 180, controller 210, a table, a phone, or within the sensor device 100 itself) or different control components of the system and perform part of the algorithms described herein.

Figure 47:
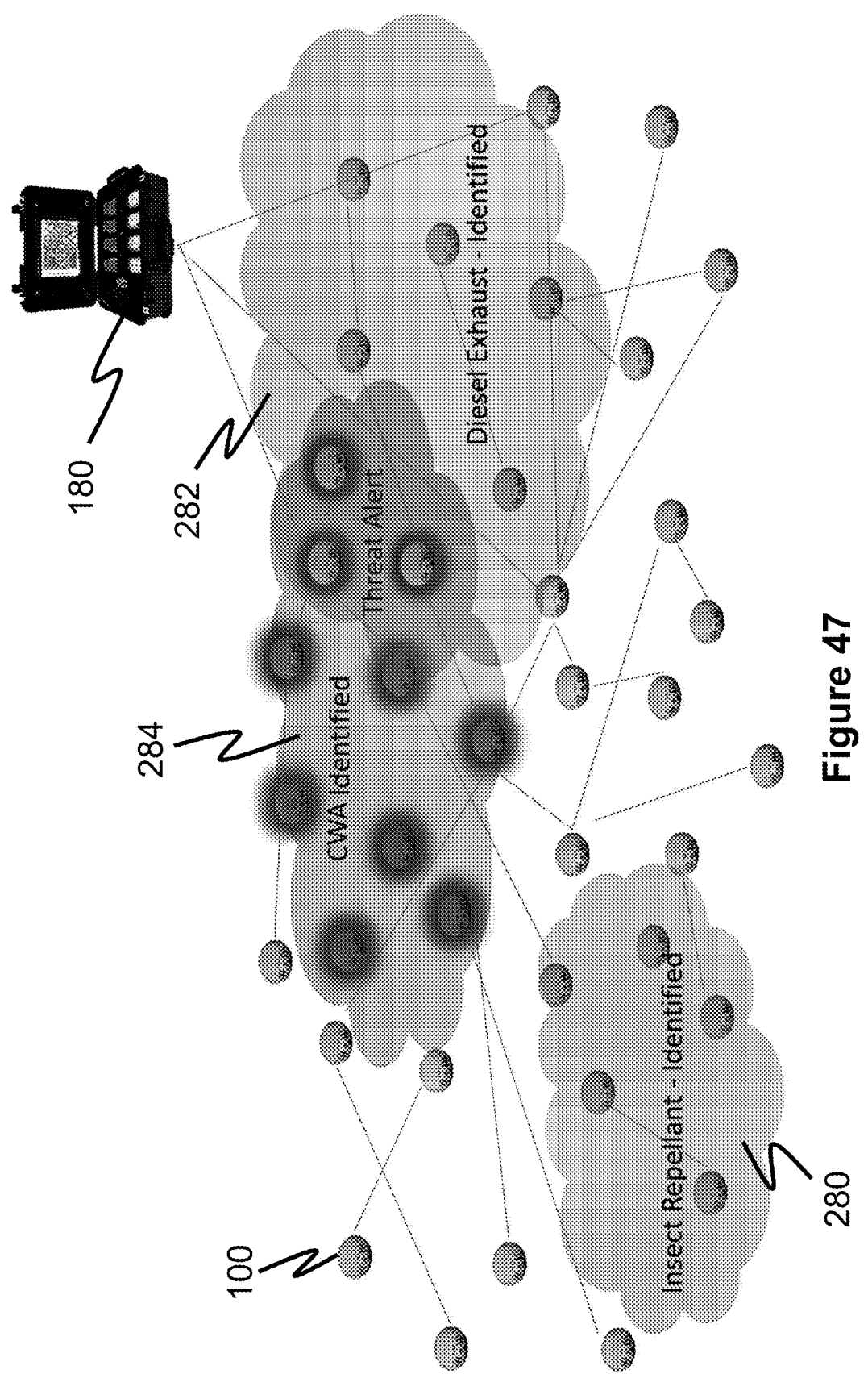
FIG. 47 illustrates a mesh network of a plurality of sensors according to one embodiment of the present invention.

One such algorithm is shown in FIG. 47 in which a plurality of sensor devices 100 are deployed over an area and are in communication (e.g., mesh communication) with the charging and control assembly 180. The sensor units 100 may identify several different airborne agents, such as an insect repellant 280, diesel exhaust 282, and a chemical warfare agent 284. In some situations, certain airborne chemicals or agents might interfere with the sensor readings of dangerous CBRNE agents. With only a single sensor device 100, detection of the CBRNE agent may be missed or have a low confidence level. However, data from multiple sensor devices 100 may detect the CBRNE agents in other portions of a monitored area, thereby confirming or otherwise increasing the confidence of detection on the CBRNE agent in an area with an interfering airborne chemical.

In one embodiment, this method includes deploying a plurality of sensor devices 100 and determining a position of each (e.g., Lat. and Long. coordinates), transmitting sensor data from the plurality of sensor devices 100 to a control system (e.g., the charging and control assembly 180), determining geographic areas containing airborne agents including an interfering airborne chemical and a CBRNE agent, determining a possible area of overlap between the interfering airborne agent and the CBRNE agent.

FIG. 47 may also be used to describe another technique according to the present invention for monitoring and warning about potential chemical reactions over a monitored target area. Since the location of each sensor unit 100 is generally known (e.g., through a GPS chip on each device 100 or via the previously described RFID method), a control system (e.g., the charging and control assembly 180) can determine if one or more agents that are sensed pose a potential risk due to their interaction with each other and alert the user as the agents come in proximity to each other and/or occupy the same space as each other. In this regard, airborne agents that might otherwise not be a threat to personnel individually can result in a user being alerted to the danger of multiple chemical reactions.

In one embodiment, this sensing method includes deploying a plurality of sensor devices 100 and determining a position of each (e.g., Lat. and Long. coordinates), transmitting sensor data from the plurality of sensor devices 100 to a control system (e.g., the charging and control assembly 180), determining geographic areas containing airborne agents, determining potential chemical interactions between at least two airborne agents, and alerting a user of a potentially harmful interaction between two or more airborne agents when these two or more airborne agents are determined to be either 1) located in close or adjacent geographic areas, or 2) at least partially overlapping geographically overlapping areas. The control system (e.g., the charging and control assembly 180) may include a database of known airborne agents and the possible chemical interactions that may take place with each other.

U.S. Pat. No. 9,804,109 is incorporated by reference and discloses some types of sensor arrays and their functionality, which may be helpful for the discussion that follows. Additional machine learning algorithms may also be used to enable base line correction of the sensor data, thus correction for sensor drift from the sensor devices 100 throughout shelf or service life. The algorithm may additionally inform the operator of the sensor drift when outside a threshold range and notify him/her of loss of functionality or reduced fidelity of the sensor. Every sensor device 100 can optionally be optimized for selected airborne agent threats (about 2 to 10 different analytes) but also can collect information with regard to threats outside of its primary analyte group (i.e., outside of what its sensors were specifically designed to sense). The output data from the sensor devices 100 can be therefore consist of 1) airborne agent identification (if the agent is part of the primary analyte group of the respective sensor device 100), 2) fused data from multiple individual sensors on a sensor array on the same sensor device 100, and 3) condensed data in the form of fingerprint or pattern information of the raw sensor data. Any direct airborne agent identification obtained by the sensor device 100 is shared with a central base station as is the characteristic signal pattern of the multi-sensor output that was used to identify the analyte.

Put another way, the sensor device 100 can transmit both a sensed airborne agent identification and the raw data or "fingerprint" behind the sensor reading in various forms. This allows for redundancy in signal transmission as well as for calculation of the fidelity in identification (percentage of signal matching library information at given condition, e.g. temperature and humidity). If the raw data analyzed by the sensor device 100 indicates an event (i.e., an agent) but specific identification is not achieved on the sensor device 100, only the pattern is sent to the base station (e.g., the charging and control assembly 180).

The combination of fingerprint data the base station receives from different sensor devices 100 can be used for threat identification even if threat identification was not possible on the sensor device level (i.e. because the specific combination of sensor elements did not match the required set for identification, whereas the combination exists on plurality of sensor devices or can be analyzed by the base station by combining the data received from plurality of sensors).

The base station compares information from multiple sensor devices 100 (particularly that are geographically nearby to the original sensor device 100) with various different sensor configurations to its larger and evolving library of patterns and events within the Machine Learning based algorithm. If the event is identified as known and a benign event/agent (such as an interferent like diesel exhaust) it informs the user but does not trigger an alarm. If the sensor information does not match any known threat nor any benign analyte, an alarm is triggered for Never-Seen-Before-Threat and the pattern is added to the library. This allows the accumulation of a library of data that can be referenced by the system in the future, forming intelligence on the reappearance of emerging threats and providing basic information on type of the analyte (e.g. corrosive, similar to a known analyte, etc).

Algorithms can further enhance the threat identification confidence (i.e., how sure the system is of the presence of an agent) with the data from multiple sensor devices 100. While sensor devices 100 can report threat identification for agents matching within their own threat library (i.e., stored in memory directly in their memory), additional identification confidence, information on false positive/negative, gas mixture, and pattern information for Never-Seen-Before Threats can be obtained through central analysis of complementary sensor data from nearby sensor devices 100.

FIGS. 48-51 illustrate examples for using additional information and to provide a confidence check from sensor devices 100 with different formulations or sensor combinations in their sensor arrays. In the present examples, the sensor devices may have different sensor elements (e.g., 4) that may be best configured to sense specific agents. In that regard, sensor devices 100 configured and optimized for sensing different agents may have at least some sensor elements in common. In that regard, a sensor device that is not configured to sense a particular type of agent may still result in signals from some of the sensor elements. In other words, a partial agent "fingerprint" may be provided for agents a sensor device is not optimized to detect. The algorithms of the present invention can use these partial "fingerprints" to estimate whether an agent is present, despite not being optimized to detect such an agent.

Figure 48:
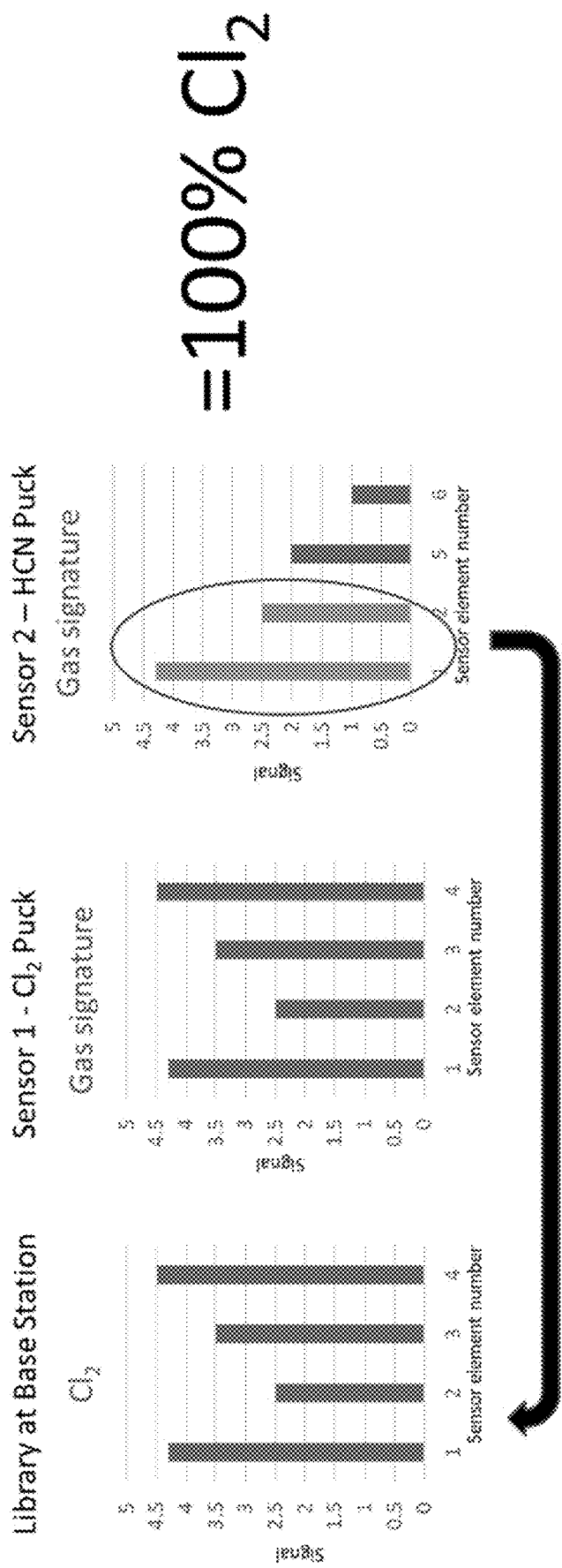
FIG. 48 illustrates a method of using sensor data according to one embodiment of the present invention.

For example, FIG. 48 illustrates data from a first sensor device that is configured to sense $Cl_2$ and a second sensor device that is configured to sense HCN. The algorithm according to the present invention can compare the positive sensor element readings of sensor elements 1 and 2 with those of a library database of such readings and corresponding agents at a base station. If the sensor elements 1 and 2 may match the $Cl_2$ fingerprint at the base station, the presence of $Cl_2$ may be determined or estimated with a relatively low confidence level. However, if a nearby first sensor device provides a matching signature for $Cl_2$, the confidence level of detection at the second sensor device may be increased (e.g., to 100%).

Figure 49:
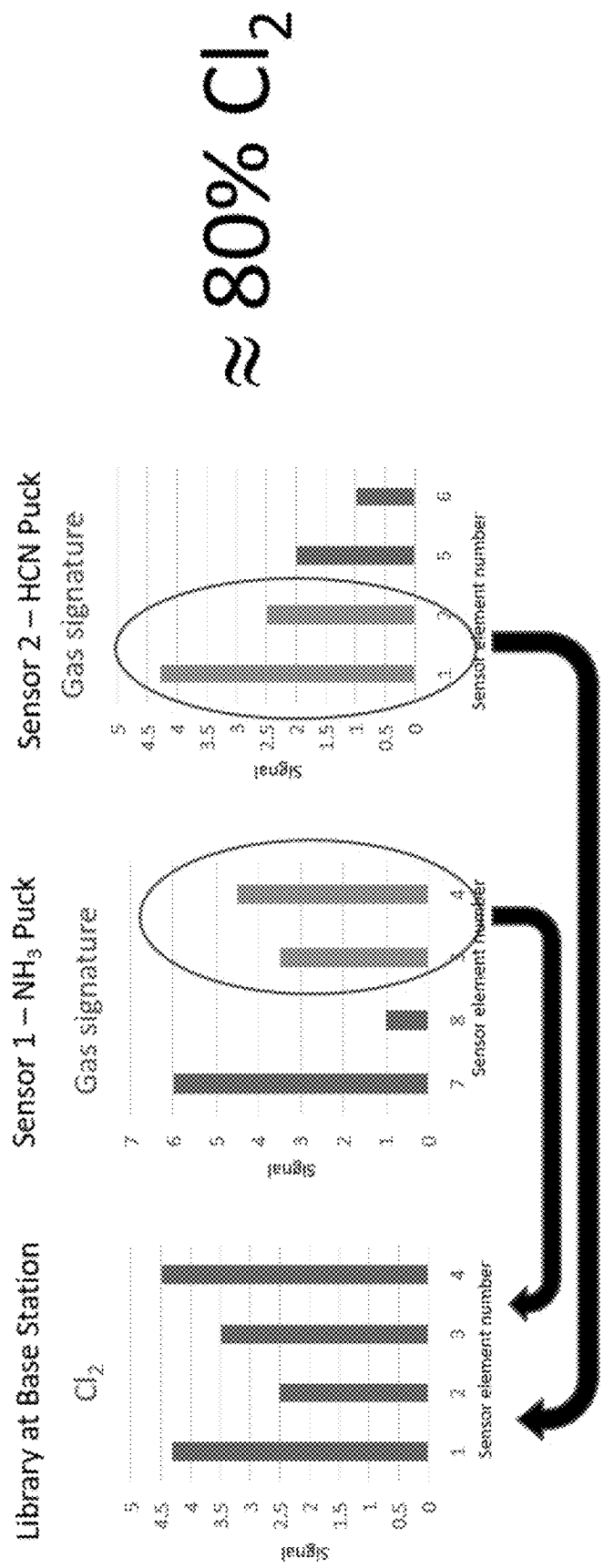
FIG. 49 illustrates a method of using sensor data according to one embodiment of the present invention.
Figure 50:
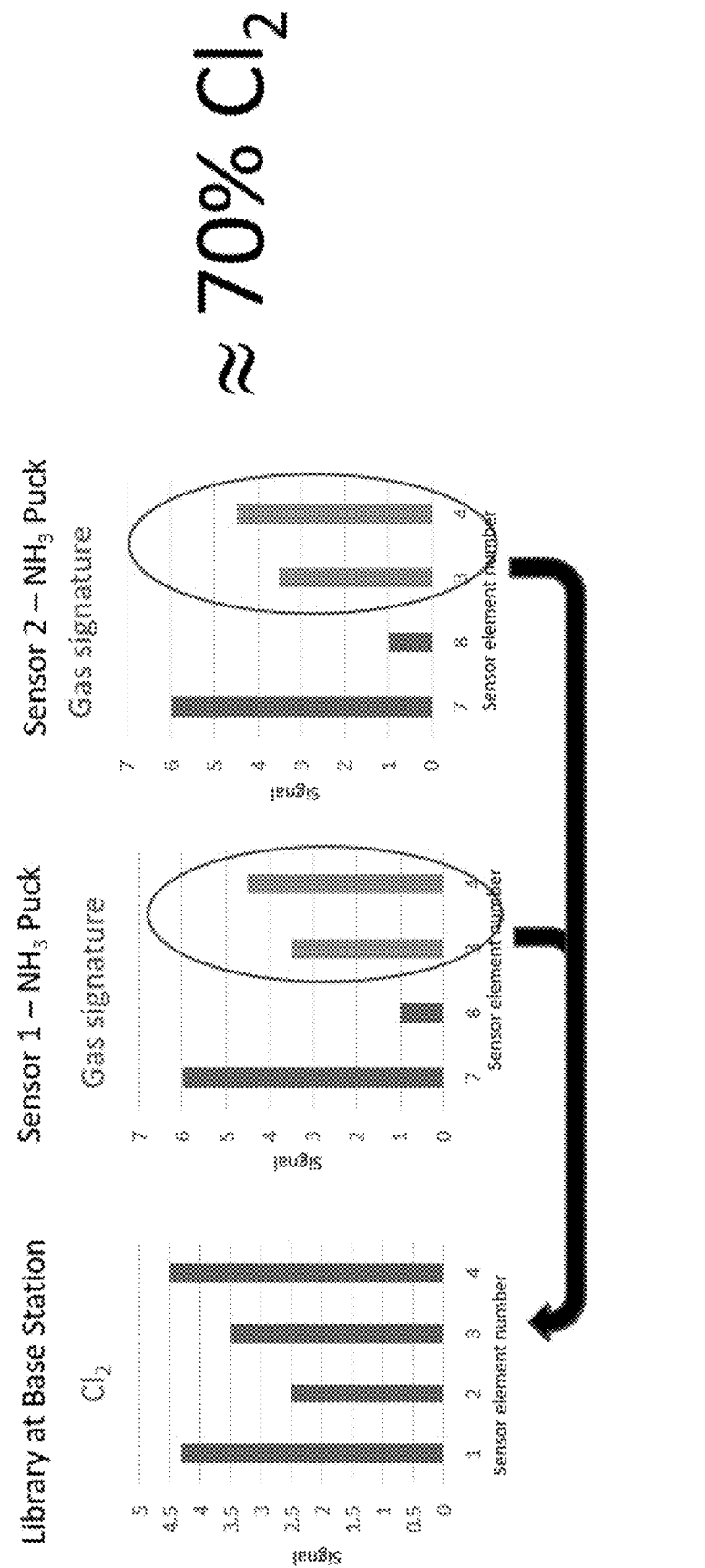
FIG. 50 illustrates a method of using sensor data according to one embodiment of the present invention.

FIG. 49 illustrates a similar example, except that two differently configured sensor devices can each provide partial fingerprint data used for a determination of the presence of an agent. For example, if sensor elements 1, 2, 3, and 4 are used for a fingerprint to determine the presence of $Cl_2$, data from elements 1 and 2 from a second sensor device configured for sensing HCN can be used with data from sensing elements 2 and 4 from a first sensor device configured for sensing NH3. Hence, multiple sensor devices with different types of sensor arrays can be used in a similar manner to a single sensor array in a single device. Additionally, as seen in FIG. 50, sensors with common types of sensor elements in their sensor arrays can be used to increase the confidence level of readings and rule out faulty readings from a single sensor device.

Figure 51:
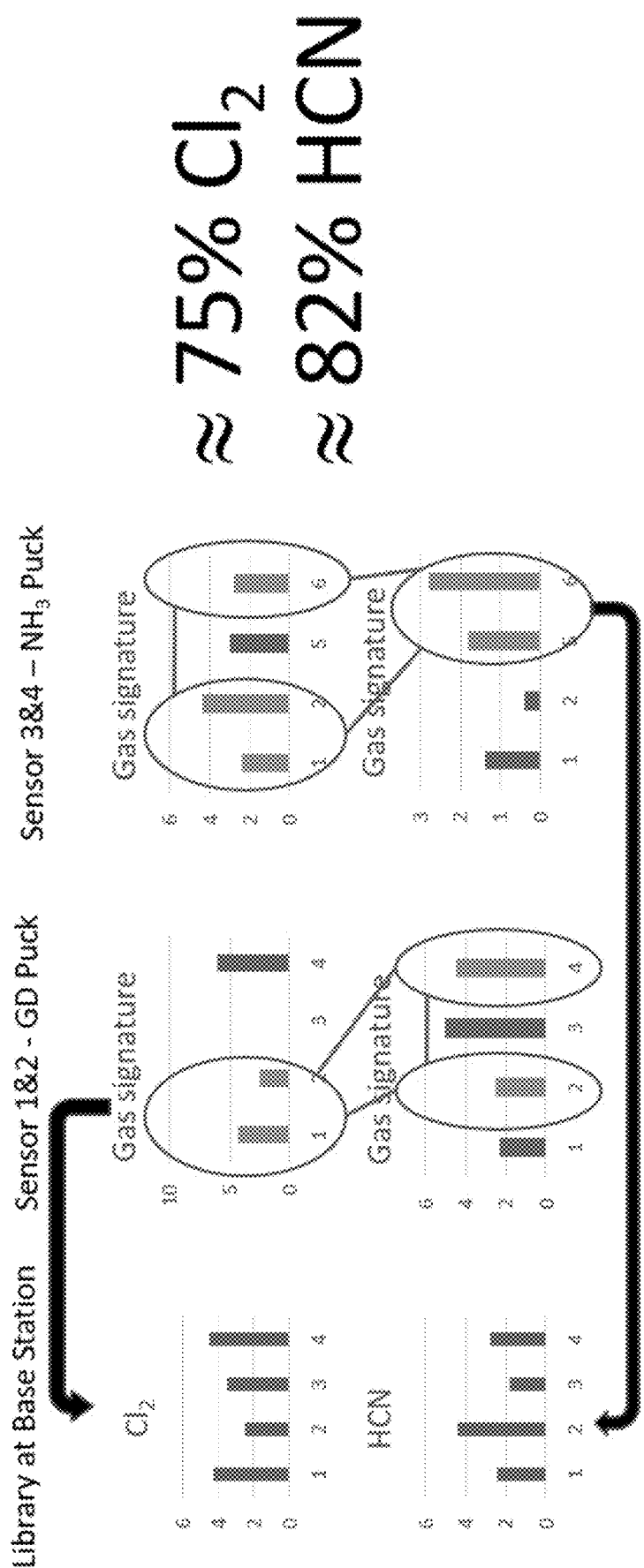
FIG. 51 illustrates a method of using sensor data according to one embodiment of the present invention.

FIG. 51 illustrates another example in which multiple airborne agents can be detected with several sensor devices, even though no single sensor device has all of the sensor elements necessary to provide a fingerprint for particular agent. For example, no specific sensor device includes sensor elements 1, 2, 3, and 4 that are needed to provide a fingerprint for $Cl_2$ and HCN. However, sensors configured for sensing other agents do have one or more of these sensor elements, allowing the base station to review the sensor data, compare the readings, and make a determination on the fingerprint for $Cl_2$ and HCN.

The sensor devices 100 can also help confirm negative responses for chemical agents. For example, a single sensor device 100 may not identify an airborne agent but may trigger an unknown threat warning as a threshold on one of its sensor elements is surpassed. In this case if no other sensor devices 100 respond, the base station will suggest possible false alarm to the user. If, however additional devices 100 show similar sensor element data in proximity, confidence of presence of a threat increases and alarms can be triggered. This can be further confirmed through sensor devices of different type, such as physiological sensors in addition to chemical, biological or RN sensors. For example signals showing increased stress biomarkers for individuals in proximity to a CBRN sensor event can be used to confirm an alarm. Location information of the sensor devices together with timestamp of the alarm, further allows for prediction of movement of a plume and can inform intelligence on immediate actions such as evacuations or area avoidance.

Figure 52:
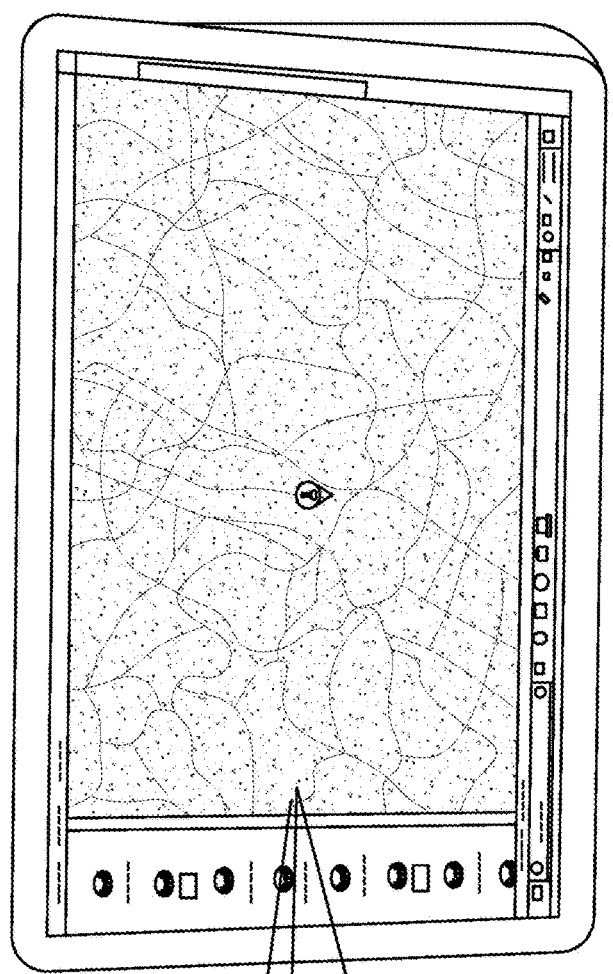
FIG. 52 illustrates a method of transmitting sensor data according to one embodiment of the present invention.
Figure 52:
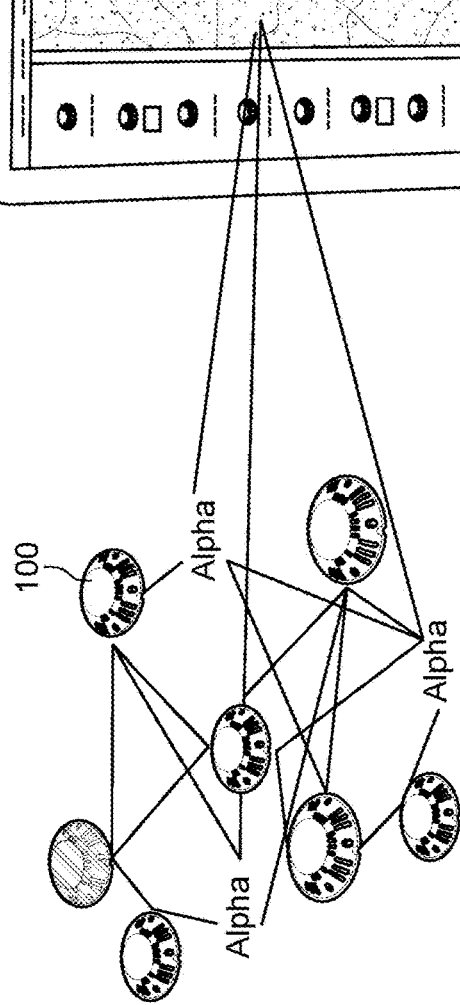
Figure 53:
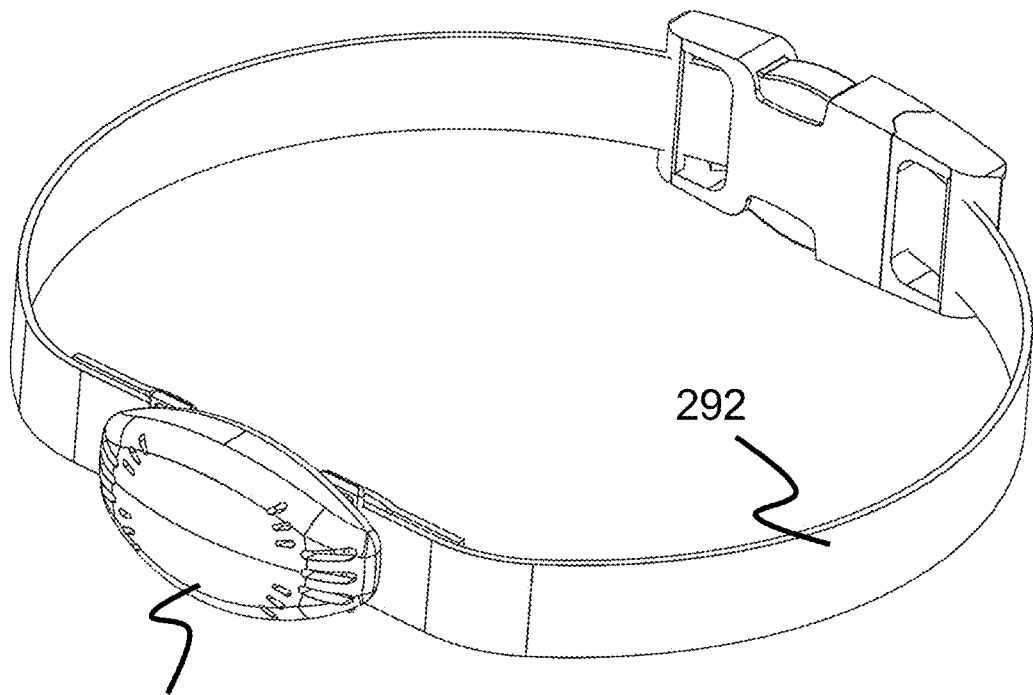
FIG. 53 is a view of a portable sensor devices for a dog according to one embodiment of the present invention.
Figure 54:
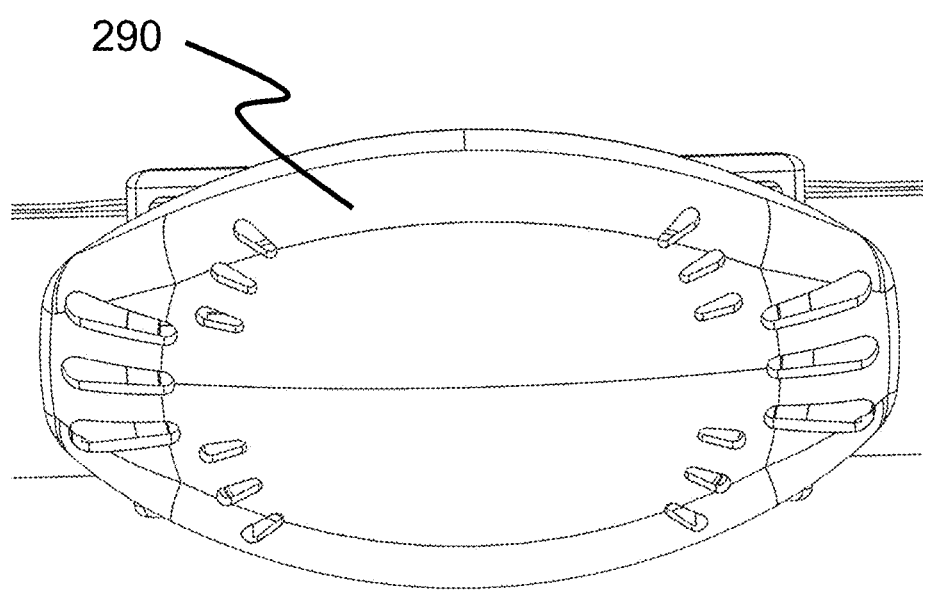
FIG. 54 is a view of a portable sensor devices for a dog according to one embodiment of the present invention.
Figure 55:
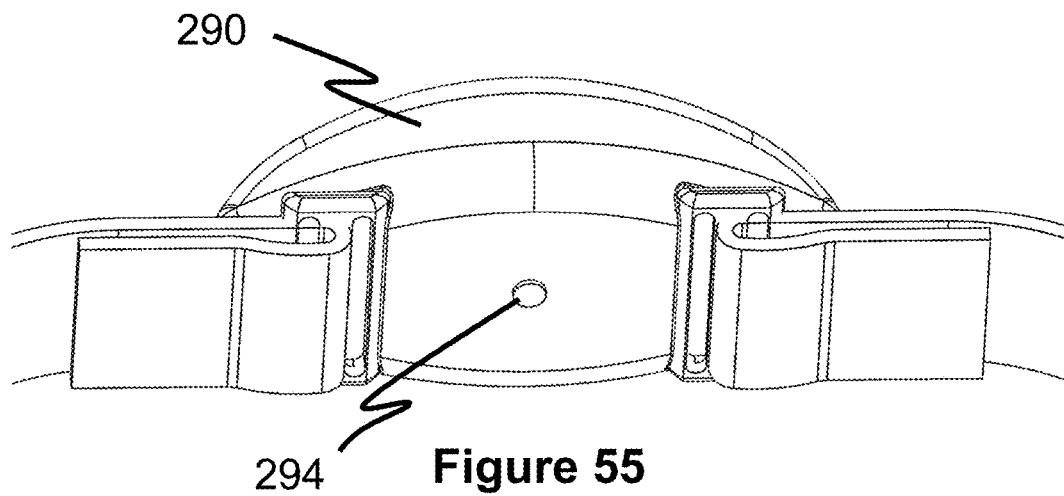
FIG. 55 is a view of a portable sensor devices for a dog according to one embodiment of the present invention.
Figure 56:
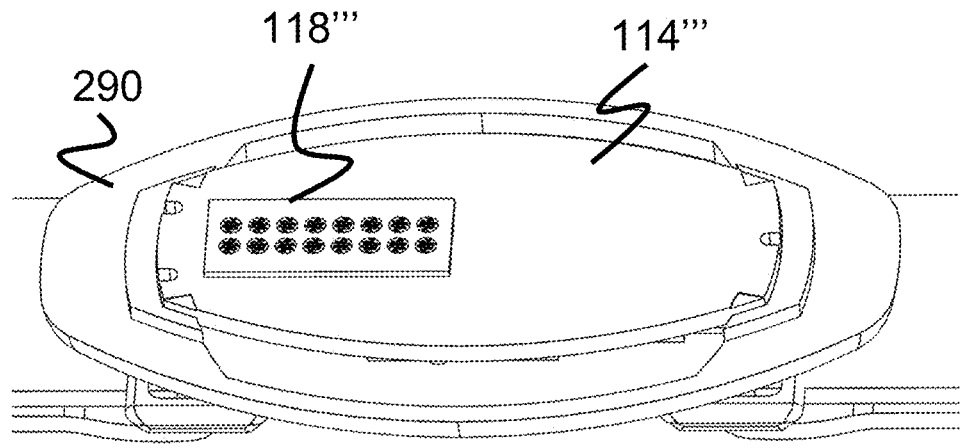
FIG. 56 is a view of a portable sensor devices for a dog according to one embodiment of the present invention.
Figure 57:
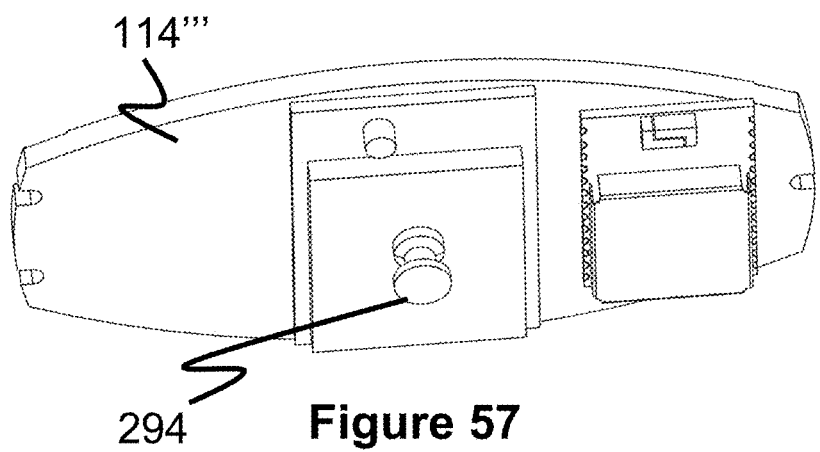
FIG. 57 is a view of a portable sensor devices for a dog according to one embodiment of the present invention.

As previously discussed, the sensor devices 100 can communicate with each other and with control systems via mesh networking, as seen in FIG. 52. However, in some circumstance, the sensor devices 100 may be located too far away for any of the sensor devices to communicate directly with the control systems. Since it may not be economically desirable to include every sensor device 100 with a cellular transceiver or a satellite phone transceiver, such more expensive and power-hungry components can be included with only a few of the plurality of sensor devices 100 that are deployed. The mesh networking data can be routed to these sensor devices 100 with additional transceivers which allow the data from all of the devices to then be transmitted back to a base/control station.

In one embodiment, one or more of the Sensor Device 100 can be configured to function with enhanced communication range (enhanced communication device). Alternately an independent communication device (i.e., a device without integrated CBRN sensors) can also be used. The shape and dimensions of the enhanced communication device is variable and scalable to permit larger battery pack and more powerful antenna to communicate to larger range, or to include satellite communication. The release mechanism 200 can be modified to carry and drop these enhanced communication devices on selected flight missions. Wherein one or more enhanced communication devices are attached to the release mechanism 200, such as using a mechanical hook. The hook mechanism can be pre-programmed to drop a enhanced communication device using a timer or can be triggered from the controller of the release mechanism or triggered from the base station as and when needed. The function of enhanced communication device can be extended to act a black box to store alarm information in the event of cyber attack to comprise the entire CBRN sensor system network.

In one embodiment we discuss how hazard prediction is made at individual level for each sensor device 100, local group of sensor devices 100 located nearby each other in vicinity (i.e. within device-to-device communication distance), non-local groups of sensor devices 100 located farther away from each other (i.e. beyond device-to-device communication distance) and ensemble of 40 sensor devices 100 in entirety located in the 2 square mile radius.

In one embodiment each sensor device 100 can have multiplicated sensor elements to build redundancy within a sensor device 100 for statistical decision making. Since the location of these redundant sensor elements is micro-level compared to the local group, non-local group and entire ensemble of 40 to 80 sensor devices 100 high accuracy can be expected on these redundant sensors. In an event of hazard detection, response between these sensor elements will be compared for decision making within the sensor device 100. Any discrepancies between the redundant sensor elements response are solved by comparing the responses, averaging them, amplifying one of them or rejecting low responding element based on multiple arguments for a meaningful decision and it will be rolled up to higher level.

In one embodiment the local group of sensor device 100 alarm reports are collected/analyzed for threat and how their decisions will be rolled up to an enhanced communication device, deployment controller, or base station. The location of these sensor devices 100 is within 300 to 500 feet between each other and considered as a block within a neighborhood. The probability of all the sensor devices 100 seeing a threat is higher in an event. Alarm response between these sensor device 100 are compared and any discrepancies between the sensor device 100 are resolved by comparing the alarm strength, % match to a chemical, reporting time stamp. The alarm information received from local sensor device 100 is used for averaging over a time, accepted or rejected after a set/variable time period from the first reported alarm from single sensor device 100. Based on multiple alarm reporting sensor device 100 vs. non reporting sensor device 100, a meaningful decision will be made and it will be rolled up to higher level non-local group decision making.

In one embodiment the non-local group sensor device 100 reports are collected/analyzed for a threat assessment and their decisions are rolled up to the enhanced communication device, release controller, or base station. The location of these sensor devices 100 away from each other can be at least more than 300 to 500 feet away each other. The probability of all the sensors seeing a threat is lower in an event depending on wind direction and size of an attack. Alarm reports from these non-local sensor devices 100 will be compared and any discrepancies between the sensor devices 100 are resolved by comparing the alarm strength, % match to a chemical, reporting time stamp. The distance between two reporting sensor devices 100 is critical with increasing time domain axis. In an event of two sensor devices 100 reporting but located 1 mile away from each other, a third sensor device 100 report is located within first two sensor device 100 location and an alarm is counted true positive or if it was from an unrelated to location then alarm can safely ignored. This decision tree continues to grow until all alarm information received from single sensor device 100, local group sensor devices 100, non-local group sensor device 100 within a certain period of time, acceptance or rejection of alarm decision will be will rolled up to higher level non-local group decision making. If the alarm reports are far apart from each other not matching a wind speed, i.e hours apart from each other reporting time then it can be safely ignored. Also, based on the alarm information received as function of time, GPS location and alarm strength a map can be displayed with safe or dander zone like cloud moving in weather map.

The previously described sensor devices 100 can also take different forms. For example, FIGS. 53-57 illustrate a sensor device 290 that is configured for a dog or for a human. The sensor device 290 is generally similar to the previously described device 100, including a housing containing a circuit board 114''', a sensor array 118''', and a battery. However, the sensor 290 may be configured to have a smaller size that is more suitable for mounting on the collar or strap 191 of a dog or human. Additionally, the sensor devices 290 may include a physiological sensor 294 to determine if the dog or human is under stress. For example, the sensor 294 may include a temperature sensor to monitor the body temperature of the dog or human. When the dog or human's body temperature is elevated, it may indicate the dog is under stress. Other sensors include a cortisol level sensor, oxygen level sensor, blood pressure sensor, pulse sensor, and similar biological sensors. When stress sensors from human/dog wearable send an alarm but sensor device 100 did not send an alarm, it will be considered as a threat as stress biomarkers override the decision by sensor device 100.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A portable sensor system comprising:
a plurality of portable airborne agent sensor devices configured to be dropped; wherein each of the plurality of portable airborne agent sensor devices comprises:
an outer housing comprised of an elastomeric material, the outer housing including a top surface and a bottom surface;
a circuit board fixed in an interior of the outer housing, the circuit board being electrically connected to one or more environmental sensors and further including a wireless transceiver configured to wirelessly transmit sensor data;
a first plurality of apertures extending through the top surface of the outer housing;
a second plurality of apertures extending through the bottom surface of the outer housing; wherein the first plurality of apertures are in communication with the second plurality of apertures allowing air to pass through the outer housing to reduce air drag when the plurality of portable airborne agent sensor devices are dropped; and
wherein each of the plurality of portable airborne agent sensor devices are free of a wing or parachute for reducing air drag during deployment.

2. The portable sensor system of claim 1, wherein the bottom surface of the outer housing has an outer region being curved upward toward the top surface of the outer housing and wherein the second plurality of apertures are positioned through the outer region of the bottom surface of the outer housing.

3. The portable sensor system of claim 1, wherein the first plurality of apertures are vertically aligned over the second plurality of apertures; and wherein the first plurality of apertures and the second plurality of apertures are symmetrically spaced so as to reduce uneven air drag when dropped.

4. The portable sensor system of claim 1, further comprising a battery located within the outer housing and mounted at a distance from the circuit board and at a bottom of the outer housing.

5. The portable sensor system of claim 1, wherein the circuit board is suspended along its edges by a gap in an interior of the outer housing.

6. The portable sensor system of claim 1, wherein the circuit board has a circular shape and an interior of the outer housing circumferentially engages an edge of the circuit board.

7. The portable sensor system of claim 1, wherein the outer housing has a circular disc shape and an oval side profile.

8. The portable sensor system of claim 1, wherein a bottom of the outer housing has a rounded shape and the second plurality of apertures are arranged along the rounded shape of the bottom of the outer housing.

9. The portable sensor system of claim 1, wherein an upper surface and a lower surface of the outer housing comprise a plurality of apertures arranged to cause each of the plurality of portable airborne agent sensor devices to spin when dropped.

10. The portable sensor system of claim 1, further comprising:
a sensor device container configured to store the plurality of portable airborne agent sensor devices; the container having a plurality of apertures positioned along the housing to at least partially expose each of the plurality of portable airborne agent sensor devices without releasing the plurality of portable airborne agent sensor devices from the housing container; and wherein each of the plurality of portable airborne agent sensor devices are configured to sense prior to being deployed from the sensor device container.

11. The portable sensor system of claim 1, further comprising:
a sensor device container comprising a tube configured to store the plurality of portable airborne agent sensor devices in a vertical stacked configuration.

12. The portable sensor system of claim 1, further comprising a sensor deployment assembly comprising a mounting bracket configured to mount to an unmanned arial vehicle; container mounting structures located below the mounting bracket and configured to releasably engage one or more sensor device containers having a tubular shape; and a release mechanism at least partially located under the container mounting structures and the one or more sensor device containers, wherein the release mechanism selectively releases one of the plurality of portable airborne agent sensor devices from within the one or more sensor device containers.

13. The portable sensor system of claim 12, further comprising an RFID sensor within the sensor deployment assembly; wherein the sensor deployment assembly is configured to sense an RFID tag in one of the plurality of portable airborne agent sensor devices, sense a GPS location of the sensor deployment assembly, and store the RFID tag and the GPS location in memory.

14. A portable sensor system comprising:
a portable airborne agent sensor device configured to be dropped; the portable airborne agent sensor device comprising:
an outer housing comprised of an elastomeric material; and,
a circuit board located in an interior of the outer housing, the circuit board being electrically connected to one or more environmental sensors and further including a wireless transceiver configured to wirelessly transmit sensor data;
a first plurality of apertures extending through a top surface of the outer housing;
a second plurality of apertures extending through a bottom surface of the outer housing, wherein the first plurality of apertures are in communication with the second plurality of apertures to allow air to pass directly through the outer housing to reduce air drag when the portable airborne agent sensor device is dropped; and
wherein each of the portable airborne agent sensor device lacks a wing or parachute for reducing air drag during deployment.

15. The portable sensor system of claim 14, wherein the bottom surface of the outer housing has an outer region being curved upward toward the top surface of the outer housing and wherein the second plurality of apertures are positioned through the outer region of the bottom surface of the outer housing.

16. The portable sensor system of claim 14, wherein the first plurality of apertures are vertically aligned over the second plurality of apertures; and wherein the first plurality of apertures and the second plurality of apertures are symmetrically spaced so as to reduce uneven air drag when dropped.

17. The portable sensor system of claim 14, further comprising a battery located within the outer housing and mounted at a distance from the circuit board and at a bottom of the outer housing.

18. The portable sensor system of claim 14, wherein the circuit board is suspended along its edges by a gap in an interior of the outer housing.

19. The portable sensor system of claim 14, wherein the circuit board has a circular shape and an interior of the outer housing circumferentially engages an edge of the circuit board.

20. The portable sensor system of claim 14, wherein the outer housing has a circular disc shape and an oval side profile.

21. The portable sensor system of claim 14, wherein an upper surface and a lower surface of the outer housing includes a plurality of apertures arranged to cause the portable airborne agent sensor device to spin when dropped.

\* \* \* \* \*